US012042268B2

(12) United States Patent
Baker et al.

(10) Patent No.: US 12,042,268 B2
(45) Date of Patent: Jul. 23, 2024

(54) PATIENT BODY MONITORING USING RADAR

(71) Applicant: Hill-Rom Services, Inc., Batesville, IN (US)

(72) Inventors: Steven D. Baker, Beaverton, OR (US); Douglas A. Seim, Okeana, OH (US); Frank E. Sauser, Cincinnati, OH (US); Theodore Corsaro, Charleston, SC (US); Michael Churilla, Harrison, OH (US); Kathryn R. Smith, Batesville, IN (US); Eric R. Meyer, Batesville, IN (US); Gregory J. Shannon, Indianapolis, IN (US); Michael S. Hood, Batesville, IN (US); Brandon P. Fisk, Batesville, IN (US); Rachel L. Williamson, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 500 days.

(21) Appl. No.: 17/189,537

(22) Filed: Mar. 2, 2021

(65) Prior Publication Data
US 2021/0298643 A1   Sep. 30, 2021

Related U.S. Application Data

(60) Provisional application No. 63/002,673, filed on Mar. 31, 2020.

(51) Int. Cl.
*A61B 5/11* (2006.01)
*A61B 5/00* (2006.01)
*A61G 7/057* (2006.01)

(52) U.S. Cl.
CPC .......... *A61B 5/1113* (2013.01); *A61B 5/0004* (2013.01); *A61B 5/0015* (2013.01);
(Continued)

(58) Field of Classification Search
CPC ... A61B 5/1113; A61B 5/0004; A61B 5/0015; A61B 5/447; A61G 7/05769;
(Continued)

(56) References Cited

U.S. PATENT DOCUMENTS 5,560,374 A  10/1996 Viard
5,625,914 A   5/1997 Schwab
(Continued)

FOREIGN PATENT DOCUMENTS

CN   106644030 A  *  5/2017  .............. G01H 9/00
CN   106644030 B      5/2020
(Continued)

OTHER PUBLICATIONS

English Translation of Chinese Patent No. CN106644030A (Year: 2017).*

(Continued)

*Primary Examiner* — Daniel L Cerioni
*Assistant Examiner* — Andrew E Hoffpauir
(74) *Attorney, Agent, or Firm* — Barnes & Thornburg LLP

(57) ABSTRACT

One or more radar sensors can be used to monitor patients in a variety of different environments and embodiments. In one embodiment, radar sensors can be used to monitor a patient's movement, including movement in a patient bed and around a room. In another embodiment, a patient position can be monitored in a patient bed, which can be used as feedback for control of bladders of a patient bed. Additional embodiments are described herein.

22 Claims, 29 Drawing Sheets

(52) U.S. Cl.
CPC .......... *A61B 5/447* (2013.01); *A61G 7/05769* (2013.01); *A61G 2203/30* (2013.01)

(58) Field of Classification Search
CPC .. A61G 7/05776; A61G 7/065; A61H 9/0078; A61H 2201/0142; A61H 2201/5058
See application file for complete search history.

(56) References Cited

U.S. PATENT DOCUMENTS

| | | | |
|---|---|---|---|
| 5,963,130 | A | 10/1999 | Schlager et al. |
| 6,009,580 | A | 1/2000 | Caminade et al. |
| 6,034,526 | A | 3/2000 | Montant et al. |
| 6,079,068 | A | 6/2000 | Viard |
| 6,244,272 | B1 | 6/2001 | Montant et al. |
| 6,518,889 | B2 | 2/2003 | Schlager et al. |
| 6,560,804 | B2 | 5/2003 | Wise et al. |
| 7,515,059 | B2 | 4/2009 | Price et al. |
| 7,676,872 | B2 | 3/2010 | Block et al. |
| 7,973,666 | B2 | 7/2011 | Petrosenko et al. |
| 8,026,840 | B2 | 9/2011 | Dwelly et al. |
| 8,281,433 | B2 | 10/2012 | Riley et al. |
| 8,352,015 | B2 | 1/2013 | Bernstein et al. |
| 8,428,696 | B2 | 4/2013 | Foo |
| 8,454,528 | B2 | 6/2013 | Yuen et al. |
| 8,525,679 | B2 | 9/2013 | Riley et al. |
| 8,740,793 | B2 | 6/2014 | Cuddihy et al. |
| 8,750,971 | B2 | 6/2014 | Tran |
| 8,781,563 | B2 | 7/2014 | Foo |
| 9,002,427 | B2 | 4/2015 | Tupin, Jr. et al. |
| 9,022,032 | B2 | 5/2015 | Holzrichter |
| 9,468,307 | B2 | 10/2016 | Lafleche et al. |
| 9,526,437 | B2 | 12/2016 | Tupin, Jr. et al. |
| 9,549,691 | B2 | 1/2017 | Tran |
| 9,775,758 | B2 | 10/2017 | Riley et al. |
| 9,993,166 | B1 | 6/2018 | Johnson et al. |
| 10,406,045 | B2 * | 9/2019 | Hayes .................. A61G 1/0275 |
| 10,548,476 | B2 | 2/2020 | Lane et al. |
| 10,813,809 | B2 | 10/2020 | Sauser et al. |
| 10,912,693 | B2 | 2/2021 | Baker et al. |
| 2008/0120780 | A1* | 5/2008 | Genaro .............. A61G 7/05776 5/600 |
| 2009/0013470 | A1* | 1/2009 | Richards ................. G16Z 99/00 5/613 |
| 2009/0270774 | A1* | 10/2009 | Gowda .............. A61H 23/0236 5/713 |
| 2010/0152600 | A1 | 6/2010 | Droitcour et al. |
| 2010/0240999 | A1 | 9/2010 | Droitcour et al. |
| 2010/0249630 | A1 | 9/2010 | Droitcour et al. |
| 2010/0249633 | A1 | 9/2010 | Droitcour et al. |
| 2010/0268121 | A1 | 10/2010 | Kilborn |
| 2010/0292568 | A1 | 11/2010 | Droitcour et al. |
| 2011/0285579 | A1 | 11/2011 | Bangera et al. |
| 2012/0023669 | A1* | 2/2012 | Graller ................. A47C 20/027 5/509.1 |
| 2012/0245479 | A1 | 9/2012 | Ganesh et al. |
| 2013/0061396 | A1* | 3/2013 | Lafleche ................ A61H 23/04 5/706 |
| 2013/0104312 | A1 | 5/2013 | O'Reagan |
| 2013/0123614 | A1 | 5/2013 | Bernstein et al. |
| 2013/0135137 | A1 | 5/2013 | Mulder et al. |
| 2015/0141794 | A1 | 5/2015 | Foo |
| 2015/0181840 | A1 | 7/2015 | Tupin, Jr. et al. |
| 2015/0208949 | A1 | 7/2015 | Tupin, Jr. et al. |
| 2015/0223733 | A1 | 8/2015 | Al-Alusi |
| 2015/0335310 | A1 | 11/2015 | Bernstein et al. |
| 2015/0369911 | A1 | 12/2015 | Mabrouk et al. |
| 2016/0022145 | A1 | 1/2016 | Mostov |
| 2016/0022204 | A1 | 1/2016 | Mostov |
| 2016/0047909 | A1 | 2/2016 | Pu et al. |
| 2016/0213321 | A1 | 7/2016 | Bernstein et al. |
| 2016/0317370 | A1 | 11/2016 | Evans et al. |
| 2017/0181409 | A1 | 6/2017 | Tupin, Jr. et al. |
| 2017/0258366 | A1 | 9/2017 | Tupin, Jr. et al. |
| 2018/0161225 | A1 | 6/2018 | Zerhusen et al. |
| 2019/0015277 | A1* | 1/2019 | Sauser ............... A61G 7/05769 |
| 2019/0053707 | A1 | 2/2019 | Lane et al. |
| 2019/0167500 | A1 | 6/2019 | Baker et al. |
| 2021/0338174 | A1* | 11/2021 | Weffers-Albu ...... A61B 5/0035 |

FOREIGN PATENT DOCUMENTS

| | | | |
|---|---|---|---|
| EP | 2298264 | A2 | 3/2011 |
| EP | 3335632 | A1 * | 6/2018 ........... A61B 5/0205 |
| EP | 3428675 | A1 | 1/2019 |
| JP | 2000118338 | | 4/2000 |
| JP | 2006226847 | | 8/2006 |
| JP | 2008536121 | | 9/2008 |
| JP | 2010508128 | | 3/2010 |
| JP | 2013538598 | | 10/2013 |
| JP | 2014209957 | | 11/2014 |
| JP | 2015528349 | | 9/2015 |

OTHER PUBLICATIONS

"Detection of Motion and Posture Change using an IR-UWB Radar," by Van Nguyen et al.; 2016 38th Annual International Conference of the IEEE Engineering in Medicine and Biology Society (EMBC), IEEE, Aug. 16, 2016, pp. 3650-3653 (4 pages).
Extended European Search Report for European Patent Application No. 21165524.6; dated Aug. 27, 2021 (9 pages).
Duraiswamy et al., "Build a UWB pulse generator on an FPGA," EDN Network, Jun. 23, 2011 (4 pages).
Spiral Antennas, "DAS and Public Safety Antennas—From Pulse Larsen-factory rep," http://www.antenna-theory.com/antennas/travelling/spiral.php; Jun. 12, 2017 (7 pages).
Tapered Baluns, Antenna Theory Home Antenna Definitions; http://www.antenna-theory.com/definitions/taperedbalun.php; Jun. 12, 2017 (2 pages).
The Infinite Balum; http://www.antenna-theory.com/definitions/infinite.php; Jun. 12, 2017 (3 pages).
Radar Basics—Minimal Measuring Range; http://www.radartutorial.eu/01.basics/Minimal%20Measuring%20Range.en.html; Jun. 12, 2017 (1 page).
Yilmaz et al, "Ultra-Wideband N-Bit Digitally Tunable Pulse Generator," published in 2005 IEEE International Conference on Ultra-Wideband; Date of Conference: Sep. 5-8, 2005; DOI: 10.1109/ICU.2005. 1570027 (8 pages).
Amir et al., "Validation of remote dielectric sensing (ReDS™) technology for quantification of lung fluid status: Comparison to high resolution chest computed tomography in patients with and without acute heart failure," International Journal of Cardiology 221 (2016) 841-846 (6 pages).
Kaneko et al, "New scale to assess breathing movements of the chest and abdominal wall" preliminary reliability testing, J. Phys. Ther. Sci. 27: 1987-1992, 2015 (6 pages).
First Chinese Office Action for Application No. 2021103367972, Dated Mar. 24, 2024, With English Translation (20 Pages).

* cited by examiner

PATIENT BODY MONITORING USING RADAR

The present application claims the benefit, under 35 U.S.C. § 119(e), of U.S. Provisional Application No. 63/002,673, filed Mar. 31, 2020, which is hereby incorporated by reference herein in its entirety.

BACKGROUND

Continuous or continual monitoring of a patient is often desirable in clinical settings. An amount of patient movement in bed can indicate risks such as pressure sores and pulmonary complications. Patient movement around a room can indicate mobility but can also lead to falls. Manual monitoring is time-intensive, prone to error, and cannot practically be done continuously for prolonged periods of time.

SUMMARY

An apparatus, system, or method may comprise one or more of the features recited in the appended claims and/or the following features which, alone or in any combination, may comprise patentable subject matter:

According to one aspect of the disclosure, a system for monitoring a patient comprises one or more radar sensors configured to transmit a radar signal towards the patient; and receive a reflection of the radar signal from the patient; and circuitry configured to receive data from the one or more radar sensors indicative of the reflection of the radar signal from the patient; and determine one or more parameters indicative of movement of the patient based on the data from the one or more radar sensors.

In some embodiments, to determine one or more parameters indicative of movement of the patient comprises to determine a body contour of the patient based on the data from the one or more radar sensors.

In some embodiments, the circuitry is further configured to determine a Braden score based on the data from the one or more radar sensors.

In some embodiments, the circuitry is further configured to determine a risk of a pressure ulcer for the patient based on the data from the one or more radar sensors.

In some embodiments, the circuitry is further configured to determine a trend of movement of the patient over a period of time of at least one week based on the data from the one or more radar sensors.

In some embodiments, the circuitry is further configured to determining a change in movement by at least a threshold amount based on the data from the one or more radar sensors; and provide an indication of the change in movement by at least the threshold amount to a caregiver.

In some embodiments, the circuitry is further configured to detect a seizure by the patient based on the data from the one or more radar sensors.

In some embodiments, the circuitry is further configured to determine, based on the data from the one or more radar sensors, whether the patient is exiting a bed.

According to one aspect of the disclosure, a system for monitoring movement of a patient comprises one or more radar sensors configured to transmit a radar signal towards a patient on a patient bed; and receive a reflection of the radar signal from the patient, and circuitry configured to receive data from the one or more radar sensors indicative of the reflection of the radar signal from the patient; and determine, based on the data from the one or more radar sensors, a position parameter of the patient, wherein the position parameter is indicative of a location or orientation of the patient on the patient bed.

In some embodiments, the circuitry is further configured to determine whether the patient should be rotated based on the position parameter of the patient.

In some embodiments, to determine whether the patient should be rotated comprises to determine whether the patient should be rotated to prevent a pressure ulcer.

In some embodiments, to determine whether the patient should be rotated comprises to determine whether the patient should be rotated to prevent laryngopharyngeal reflux.

In some embodiments, to determine whether the patient should be rotated comprises to determine whether the patient should be rotated to elevate a lung of the patient.

In some embodiments, to determine whether the patient should be rotated comprises to determine that the patient has not been rotated for at least a threshold amount of time.

In some embodiments, the circuitry is further configured to determine, based on the position parameter, a subset of a plurality of rotation bladders of the patient bed to inflate in order to rotate the patient; and send a signal to inflate the subset of the plurality of rotation bladders.

In some embodiments, the circuitry is further configured to determine, based on the position parameter, a subset of a plurality of rotation bladders of the patient bed to inflate in order to move the patient towards a center of the patient bed; and send a signal to inflate the subset of the plurality of rotation bladders.

In some embodiments, the circuitry is further configured to determine, based on the position parameter, a subset of a plurality of percussion and vibration (P & V) bladders of the patient bed to inflate in order to perform P & V therapy on the patient, wherein the selected subset of the plurality of P & V bladders are P &V bladders under a current position of the patient; and send a signal to inflate the subset of the plurality of P & V bladders.

In some embodiments, the circuitry is further configured to transmit, by the one or more radar sensors, an additional radar signal towards the patient during the P & V therapy; receive, by the one or more radar sensors, a reflection of the additional radar signal from the patient; receive additional data from the one or more radar sensors indicative of the reflection of the additional radar signal from the patient; determine, based on the additional data from the one or more radar sensors, an amplitude of vibration of the patient caused by the P & V therapy; and adjust a signal sent to inflate the subset of the plurality of P & V bladders based on the amplitude of vibration of the patient.

In some embodiments, the circuitry is further configured to determine, based on the position parameter, a subset of a plurality of rotation bladders of the patient bed to inflate in order to move the patient towards a center of the patient bed; and send a signal to inflate the subset of the plurality of rotation bladders to move the patient towards the center of the patient bed prior to sending the signal to inflate the subset of the plurality of P & V bladders.

According to one aspect of the disclosure, a system for monitoring a patient comprises one or more radar sensors configured to transmit a radar signal towards a patient on a patient bed; and receive a reflection of the radar signal from the patient, and circuitry configured to receive data from the one or more radar sensors indicative of the reflection of the radar signal from the patient; determine, based on the data from the one or more radar sensors, an area of the body of the patient that is in contact with a surface of the patient bed; determine, based on the data from the one or more radar sensors, one or more air bladders to control to relieve pressure from the area of the body that is in contact with the surface of the patient bed; and control the one or more air bladders to relieve pressure from the area of the body that is in contact with the surface of the patient bed.

In some embodiments, the area of the body that is in contact with the surface of the patient bed is a heel of the patient.

In some embodiments, the area of the body that is in contact with the surface of the patient bed is a sacrum of the patient.

According to one aspect of the disclosure, a system for managing a microclimate of a patient comprises one or more radar sensors configured to transmit a radar signal towards a patient on a patient bed; and receive a reflection of the radar signal from the patient, and circuitry configured to receive data from the one or more radar sensors indicative of the reflection of the radar signal from the patient; determine a targeted body part of the patient for microclimate management; determine, based on the data from the one or more radar sensors, a location of the targeted body part; and control, based on the determined location of the targeted body part, an airflow to the targeted body part.

In some embodiments, to control the airflow to the targeted body part comprises to control the airflow to the targeted body part based on a moisture level of the targeted body part.

In some embodiments, to control the airflow to the targeted body part comprises to control a humidity of airflow to the targeted body part.

In some embodiments, to control the airflow to the targeted body part comprises to control a temperature of airflow to the targeted body part.

According to one aspect of the disclosure, a system for monitoring a patient comprises one or more radar sensors configured to transmit a radar signal towards a patient in a room; and receive a reflection of the radar signal from the patient, and circuitry configured to receive data from the one or more radar sensors indicative of the reflection of the radar signal from the patient; and determine one or more parameters indicative of a position of the patient based on the data from the one or more radar sensors.

In some embodiments, to determine the one or more parameters indicative of the position of the patient based on the data from the one or more radar sensors comprises to determine an amount of time the patient is lying down in a patient bed; determine an amount of time the patient is sitting up in the patient bed; determine an amount of time the patient is sitting in a chair; and determine an amount of time the patient is standing or walking.

In some embodiments, the circuitry is further configured to determine, based on the data from the one or more radar sensors, whether the patient has an unsteady gait; and transmit, in response to a determination that the patient has an unsteady gait, an alert to a caregiver.

In some embodiments, the circuitry is further configured to determine, based on the data from the one or more radar sensors, whether the patient is leaving the room; and transmit, in response to a determination that the patient has left the room, an alert to a caregiver.

In some embodiments, the circuitry is further configured to determine, based on the data from the one or more radar sensors, whether the patient has fallen to the ground; and transmit, in response to a determination that the patient has fallen to the ground, an alert to a caregiver.

In some embodiments, to determine whether the patient has fallen to the ground comprises to determine whether the patient has fallen to the ground in a second room different from the room with the one or more radar sensors.

In some embodiments, the circuitry is further configured to determine one or more parameters indicative of an activity of a caregiver in the room.

In some embodiments, the one or more parameters indicative of an activity of the caregiver in the room indicate an amount of interaction of the caregiver with the patient.

In some embodiments, the one or more parameters indicative of an activity of the caregiver in the room indicate whether the caregiver washed the caregiver's hands.

In some embodiments, the one or more parameters indicative of an activity of the caregiver in the room indicate an amount of time the caregiver reviewed the medical records of the patient.

According to one aspect of the disclosure, a system for facilitating physical therapy exercises comprises circuitry configured to present a physical therapy instruction to a patient; and one or more radar sensors configured to transmit a radar signal towards the patient after presentation of the physical therapy instruction; and receive a reflection of the radar signal from the patient, wherein the circuitry is further configured to transmit, by one or more radar sensors, a radar signal towards the patient after presentation of the physical therapy instruction; receive, by the one or more radar sensors, a reflection of the radar signal from the patient; receive data from the one or more radar sensors indicative of the reflection of the radar signal from the patient; determine, based on the data from the one or more radar sensors, a movement parameter of the patient; and compare the movement parameter of the patient with the physical therapy instruction.

In some embodiments, to present the physical therapy instruction to the patient comprises to present the physical therapy instruction on a display, wherein the patient is in a patient bed, and wherein the display is attached to the patient bed.

In some embodiments, to present the physical therapy instruction to the patient comprises to present the physical therapy instruction on a display, and wherein the display is attached to a mobile physical therapy instruction exercise device.

In some embodiments, the circuitry is further configured to store performance data of the patient during an exercise session associated with the physical therapy instruction, wherein the performance data indicates a response of the patient to the physical therapy instruction.

In some embodiments, the circuitry is further configured to determine, based on the performance data, a second physical therapy instruction of a second exercise session different from the first.

According to one aspect of the disclosure, a system for monitoring a patient sleeping comprises one or more radar sensors configured to transmit a radar signal towards a patient on a patient bed; and receive a reflection of the radar signal from the patient, and circuitry configured to receive data from the one or more radar sensors indicative of the reflection of the radar signal from the patient; determine, based on the data from the one or more radar sensors, an indication of the patient pushing up in the bed; determine, based on the indication of the patient pushing up in the patient bed, a pressure parameter for one or more air bladders in the patient bed; and apply the pressure parameter to the one or more air bladders in the patient bed.

In some embodiments, to determine the pressure parameter for the one or more air bladders in the patient bed comprises to determine the pressure parameter for the one or more air bladders in the patient bed with use of a machine-learning-based algorithm.

In some embodiments, the circuitry is further configured to update a machine-learning-based algorithm based on the patient pushing up in the patient bed.

According to one aspect of the disclosure, a system for monitoring a patient comprises one or more radar sensors configured to transmit a radar signal towards a patient in a prone position on a patient bed; and receive a reflection of the radar signal from the patient, and circuitry configured to receive, by circuitry, data from the one or more radar sensors indicative of the reflection of the radar signal from the patient; determine, based on the data from the one or more radar sensors, whether there is a gap between a sternum of the patient and a surface of the patient bed while the patient is breathing in.

In some embodiments, the circuitry is further configured to deflate, in response to a determination that there is not a gap between a sternum of the patient and a surface of the patient bed while the patient is breathing in, one or more air bladders beneath the sternum of the patient.

In some embodiments, to determine whether there is a gap between a sternum of the patient and a surface of the patient bed while the patient is breathing in comprises to deflate one or more air bladders beneath the sternum of the patient while the patient is breathing in.

According to one aspect of the disclosure, a method for monitoring a patient comprises transmitting, by one or more radar sensors, a radar signal towards a patient; receiving, by the one or more radar sensors, a reflection of the radar signal from the patient; receiving, by circuitry, data from the one or more radar sensors indicative of the reflection of the radar signal from the patient; and determining, by the circuitry, one or more parameters indicative of movement of the patient based on the data from the one or more radar sensors.

In some embodiments, determining one or more parameters indicative of movement of the patient comprises determining a body contour of the patient based on the data from the one or more radar sensors.

In some embodiments, the method may further include determining a Braden score based on the data from the one or more radar sensors.

In some embodiments, the method may further include determining a risk of a pressure ulcer for the patient based on the data from the one or more radar sensors.

In some embodiments, the method may further include determining a trend of movement of the patient over a period of time of at least one week based on the data from the one or more radar sensors.

In some embodiments, the method may further include determining a change in movement by at least a threshold amount based on the data from the one or more radar sensors; and providing an indication of the change in movement by at least the threshold amount to a caregiver.

In some embodiments, the method may further include detecting a seizure by the patient based on the data from the one or more radar sensors.

In some embodiments, the method may further include determining, based on the data from the one or more radar sensors, whether the patient is exiting a bed.

According to one aspect of the disclosure, a method for monitoring movement of a patient comprises transmitting, by one or more radar sensors, a radar signal towards a patient on a patient bed; receiving, by the one or more radar sensors, a reflection of the radar signal from the patient; receiving, by circuitry, data from the one or more radar sensors indicative of the reflection of the radar signal from the patient; and determining, by the circuitry and based on the data from the one or more radar sensors, a position parameter of the patient, wherein the position parameter is indicative of a location or orientation of the patient on the patient bed.

In some embodiments, the method may further include determining, by the circuitry, whether the patient should be rotated based on the position parameter of the patient.

In some embodiments, determining whether the patient should be rotated comprises determining whether the patient should be rotated to prevent a pressure ulcer.

In some embodiments, determining whether the patient should be rotated comprises determining whether the patient should be rotated to prevent laryngopharyngeal reflux.

In some embodiments, determining whether the patient should be rotated comprises determining whether the patient should be rotated to elevate a lung of the patient.

In some embodiments, determining whether the patient should be rotated comprises determining that the patient has not been rotated for at least a threshold amount of time.

In some embodiments, the method may further include determining, by the circuitry and based on the position parameter, a subset of a plurality of rotation bladders of the patient bed to inflate in order to rotate the patient; and sending, by the circuitry, a signal to inflate the subset of the plurality of rotation bladders.

In some embodiments, the method may further include determining, by the circuitry and based on the position parameter, a subset of a plurality of rotation bladders of the patient bed to inflate in order to move the patient towards a center of the patient bed; and sending, by the circuitry, a signal to inflate the subset of the plurality of rotation bladders.

In some embodiments, the method may further include determining, by the circuitry and based on the position parameter, a subset of a plurality of percussion and vibration (P & V) bladders of the patient bed to inflate in order to perform P & V therapy on the patient, wherein the selected subset of the plurality of P & V bladders are P &V bladders under a current position of the patient; and sending, by the circuitry, a signal to inflate the subset of the plurality of P & V bladders.

In some embodiments, the method may further include transmitting, by the one or more radar sensors, an additional radar signal towards the patient during the P & V therapy; receiving, by the one or more radar sensors, a reflection of the additional radar signal from the patient; receiving, by the circuitry, additional data from the one or more radar sensors indicative of the reflection of the additional radar signal from the patient; determining, by the circuitry and based on the additional data from the one or more radar sensors, an amplitude of vibration of the patient caused by the P & V therapy; and adjusting, by the circuitry, a signal sent to inflate the subset of the plurality of P & V bladders based on the amplitude of vibration of the patient.

In some embodiments, the method may further include determining, by the circuitry and based on the position parameter, a subset of a plurality of rotation bladders of the patient bed to inflate in order to move the patient towards a center of the patient bed; and sending, by the circuitry, a signal to inflate the subset of the plurality of rotation bladders to move the patient towards the center of the patient bed prior to sending the signal to inflate the subset of the plurality of P & V bladders.

According to one aspect of the disclosure, a method for monitoring a patient comprises transmitting, by one or more radar sensors, a radar signal towards a patient on a patient bed; receiving, by the one or more radar sensors, a reflection of the radar signal from the patient; receiving, by circuitry, data from the one or more radar sensors indicative of the reflection of the radar signal from the patient; determining, by the circuitry and based on the data from the one or more radar sensors, an area of the body of the patient that is in contact with a surface of the patient bed; determining, by the circuitry and based on the data from the one or more radar sensors, one or more air bladders to control to relieve pressure from the area of the body that is in contact with the surface of the patient bed; and controlling, by the circuitry, the one or more air bladders to relieve pressure from the area of the body that is in contact with the surface of the patient bed.

In some embodiments, the area of the body that is in contact with the surface of the patient bed is a heel of the patient.

In some embodiments, the area of the body that is in contact with the surface of the patient bed is a sacrum of the patient.

According to one aspect of the disclosure, a method for managing a microclimate of a patient comprises transmitting, by one or more radar sensors, a radar signal towards a patient on a patient bed; receiving, by the one or more radar sensors, a reflection of the radar signal from the patient; receiving, by circuitry, data from the one or more radar sensors indicative of the reflection of the radar signal from the patient; determining, by the circuitry, a targeted body part of the patient for microclimate management; determining, by the circuitry and based on the data from the one or more radar sensors, a location of the targeted body part; and controlling, by the circuitry and based on the determined location of the targeted body part, an airflow to the targeted body part.

In some embodiments, controlling the airflow to the targeted body part comprises controlling the airflow to the targeted body part based on a moisture level of the targeted body part.

In some embodiments, controlling the airflow to the targeted body part comprises controlling a humidity of airflow to the targeted body part.

In some embodiments, controlling the airflow to the targeted body part comprises controlling a temperature of airflow to the targeted body part.

According to one aspect of the disclosure, a method for monitoring a patient comprises transmitting, by one or more radar sensors, a radar signal towards a patient in a room; receiving, by the one or more radar sensors, a reflection of the radar signal from the patient; receiving, by circuitry, data from the one or more radar sensors indicative of the reflection of the radar signal from the patient; and determining, by the circuitry, one or more parameters indicative of a position of the patient based on the data from the one or more radar sensors.

In some embodiments, determining, by the circuitry, the one or more parameters indicative of the position of the patient based on the data from the one or more radar sensors comprises determining, by the circuitry, an amount of time the patient is lying down in a patient bed; determining, by the circuitry, an amount of time the patient is sitting up in the patient bed; determining, by the circuitry, an amount of time the patient is sitting in a chair; and determining, by the circuitry, an amount of time the patient is standing or walking.

In some embodiments, the method may further include determining, by the circuitry and based on the data from the one or more radar sensors, whether the patient has an unsteady gait; and transmitting, by the circuitry and in response to a determination that the patient has an unsteady gait, an alert to a caregiver.

In some embodiments, the method may further include determining, by the circuitry and based on the data from the one or more radar sensors, whether the patient is leaving the room; and transmitting, by the circuitry and in response to a determination that the patient has left the room, an alert to a caregiver.

In some embodiments, the method may further include determining, by the circuitry and based on the data from the one or more radar sensors, whether the patient has fallen to the ground; and transmitting, by the circuitry and in response to a determination that the patient has fallen to the ground, an alert to a caregiver.

In some embodiments, determining whether the patient has fallen to the ground comprises determining whether the patient has fallen to the ground in a second room different from the room with the one or more radar sensors.

In some embodiments, the method may further include determining, by the circuitry, one or more parameters indicative of an activity of a caregiver in the room.

In some embodiments, the one or more parameters indicative of an activity of the caregiver in the room indicate an amount of interaction of the caregiver with the patient.

In some embodiments, the one or more parameters indicative of an activity of the caregiver in the room indicate whether the caregiver washed the caregiver's hands.

In some embodiments, the one or more parameters indicative of an activity of the caregiver in the room indicate an amount of time the caregiver reviewed the medical records of the patient.

According to one aspect of the disclosure, a method for facilitating physical therapy exercises comprises presenting, by circuitry, a physical therapy instruction to a patient; transmitting, by one or more radar sensors, a radar signal towards the patient after presentation of the physical therapy instruction; receiving, by the one or more radar sensors, a reflection of the radar signal from the patient; receiving, by the circuitry, data from the one or more radar sensors indicative of the reflection of the radar signal from the patient; determining, by the circuitry and based on the data from the one or more radar sensors, a movement parameter of the patient; and comparing, by the circuitry, the movement parameter of the patient with the physical therapy instruction.

In some embodiments, presenting the physical therapy instruction to the patient comprises presenting the physical therapy instruction on a display, wherein the patient is in a patient bed, and wherein the display is attached to the patient bed.

In some embodiments, presenting the physical therapy instruction to the patient comprises presenting the physical therapy instruction on a display, and wherein the display is attached to a mobile physical therapy instruction exercise device.

In some embodiments, the method may further include storing, by the circuitry, performance data of the patient during an exercise session associated with the physical therapy instruction, wherein the performance data indicates a response of the patient to the physical therapy instruction.

In some embodiments, the method may further include determining, by the circuitry and based on the performance data, a second physical therapy instruction of a second exercise session different from the first.

According to one aspect of the disclosure, a method for monitoring a patient sleeping comprises transmitting, by one or more radar sensors, a radar signal towards a patient on a patient bed; receiving, by the one or more radar sensors, a reflection of the radar signal from the patient; receiving, by circuitry, data from the one or more radar sensors indicative of the reflection of the radar signal from the patient; determining, by the circuitry and based on the data from the one or more radar sensors, an indication of the patient pushing up in the bed; determining, by the circuitry and based on the indication of the patient pushing up in the patient bed, a pressure parameter for one or more air bladders in the patient bed; and applying, by the circuitry, the pressure parameter to the one or more air bladders in the patient bed.

In some embodiments, determining the pressure parameter for the one or more air bladders in the patient bed comprises determining the pressure parameter for the one or more air bladders in the patient bed with use of a machine-learning-based algorithm.

In some embodiments, the method may further include updating a machine-learning-based algorithm based on the patient pushing up in the patient bed.

According to one aspect of the disclosure, a method for monitoring a patient comprises transmitting, by one or more radar sensors, a radar signal towards a patient in a prone position on a patient bed; receiving, by the one or more radar sensors, a reflection of the radar signal from the patient; receiving, by circuitry, data from the one or more radar sensors indicative of the reflection of the radar signal from the patient; determining, by the circuitry and based on the data from the one or more radar sensors, whether there is a gap between a sternum of the patient and a surface of the patient bed while the patient is breathing in.

In some embodiments, the method may further include deflating, by the circuitry and in response to a determination that there is not a gap between a sternum of the patient and a surface of the patient bed while the patient is breathing in, one or more air bladders beneath the sternum of the patient.

In some embodiments, determining whether there is a gap between a sternum of the patient and a surface of the patient bed while the patient is breathing in comprises deflating, by the circuitry, one or more air bladders beneath the sternum of the patient while the patient is breathing in.

According to one aspect of the disclosure, one or more computer-readable media comprising a plurality of instructions stored thereon that, when executed, causes a compute device to transmit, by one or more radar sensors, a radar signal towards a patient; receive, by the one or more radar sensors, a reflection of the radar signal from the patient; receive data from the one or more radar sensors indicative of the reflection of the radar signal from the patient; and determine one or more parameters indicative of movement of the patient based on the data from the one or more radar sensors.

In some embodiments, to determine one or more parameters indicative of movement of the patient comprises to determine a body contour of the patient based on the data from the one or more radar sensors.

In some embodiments, the plurality of instructions further cause the compute device to determine a Braden score based on the data from the one or more radar sensors.

In some embodiments, the plurality of instructions further cause the compute device to determine a risk of a pressure ulcer for the patient based on the data from the one or more radar sensors.

In some embodiments, the plurality of instructions further cause the compute device to determine a trend of movement of the patient over a period of time of at least one week based on the data from the one or more radar sensors.

In some embodiments, the plurality of instructions further cause the compute device to determining a change in movement by at least a threshold amount based on the data from the one or more radar sensors; and provide an indication of the change in movement by at least the threshold amount to a caregiver.

In some embodiments, the plurality of instructions further cause the compute device to detect a seizure by the patient based on the data from the one or more radar sensors.

In some embodiments, the plurality of instructions further cause the compute device to determine, based on the data from the one or more radar sensors, whether the patient is exiting a bed.

According to one aspect of the disclosure, one or more computer-readable media comprising a plurality of instructions stored thereon that, when executed, causes a compute device to transmit, by one or more radar sensors, a radar signal towards a patient on a patient bed; receive, by the one or more radar sensors, a reflection of the radar signal from the patient; receive data from the one or more radar sensors indicative of the reflection of the radar signal from the patient; and determine, based on the data from the one or more radar sensors, a position parameter of the patient, wherein the position parameter is indicative of a location or orientation of the patient on the patient bed.

In some embodiments, the plurality of instructions further cause the compute device to determine whether the patient should be rotated based on the position parameter of the patient.

In some embodiments, to determine whether the patient should be rotated comprises to determine whether the patient should be rotated to prevent a pressure ulcer.

In some embodiments, to determine whether the patient should be rotated comprises to determine whether the patient should be rotated to prevent laryngopharyngeal reflux.

In some embodiments, to determine whether the patient should be rotated comprises to determine whether the patient should be rotated to elevate a lung of the patient.

In some embodiments, to determine whether the patient should be rotated comprises to determine that the patient has not been rotated for at least a threshold amount of time.

In some embodiments, the plurality of instructions further cause the compute device to determine, based on the position parameter, a subset of a plurality of rotation bladders of the patient bed to inflate in order to rotate the patient; and send a signal to inflate the subset of the plurality of rotation bladders.

In some embodiments, the plurality of instructions further cause the compute device to determine, based on the position parameter, a subset of a plurality of rotation bladders of the patient bed to inflate in order to move the patient towards a center of the patient bed; and send a signal to inflate the subset of the plurality of rotation bladders.

In some embodiments, the plurality of instructions further cause the compute device to determine, based on the position parameter, a subset of a plurality of percussion and vibration (P & V) bladders of the patient bed to inflate in order to perform P & V therapy on the patient, wherein the selected subset of the plurality of P & V bladders are P &V bladders under a current position of the patient; and send a signal to inflate the subset of the plurality of P & V bladders.

In some embodiments, the plurality of instructions further cause the compute device to transmit, by the one or more radar sensors, an additional radar signal towards the patient during the P & V therapy; receive, by the one or more radar sensors, a reflection of the additional radar signal from the patient; receive additional data from the one or more radar sensors indicative of the reflection of the additional radar signal from the patient; determine, based on the additional data from the one or more radar sensors, an amplitude of vibration of the patient caused by the P & V therapy; and adjust a signal sent to inflate the subset of the plurality of P & V bladders based on the amplitude of vibration of the patient.

In some embodiments, the plurality of instructions further cause the compute device to determine, based on the position parameter, a subset of a plurality of rotation bladders of the patient bed to inflate in order to move the patient towards a center of the patient bed; and send a signal to inflate the subset of the plurality of rotation bladders to move the patient towards the center of the patient bed prior to sending the signal to inflate the subset of the plurality of P & V bladders.

According to one aspect of the disclosure, one or more computer-readable media comprising a plurality of instructions stored thereon that, when executed, causes a compute device to transmit, by one or more radar sensors, a radar signal towards a patient on a patient bed; receive, by the one or more radar sensors, a reflection of the radar signal from the patient; receive data from the one or more radar sensors indicative of the reflection of the radar signal from the patient; determine, based on the data from the one or more radar sensors, an area of the body of the patient that is in contact with a surface of the patient bed; determine, based on the data from the one or more radar sensors, one or more air bladders to control to relieve pressure from the area of the body that is in contact with the surface of the patient bed; and control the one or more air bladders to relieve pressure from the area of the body that is in contact with the surface of the patient bed.

In some embodiments, the area of the body that is in contact with the surface of the patient bed is a heel of the patient.

In some embodiments, the area of the body that is in contact with the surface of the patient bed is a sacrum of the patient.

According to one aspect of the disclosure, one or more computer-readable media comprising a plurality of instructions stored thereon that, when executed, causes a compute device to transmit, by one or more radar sensors, a radar signal towards a patient on a patient bed; receive, by the one or more radar sensors, a reflection of the radar signal from the patient; receive data from the one or more radar sensors indicative of the reflection of the radar signal from the patient; determine a targeted body part of the patient for microclimate management; determine, based on the data from the one or more radar sensors, a location of the targeted body part; and control, based on the determined location of the targeted body part, an airflow to the targeted body part.

In some embodiments, to control the airflow to the targeted body part comprises to control the airflow to the targeted body part based on a moisture level of the targeted body part.

In some embodiments, to control the airflow to the targeted body part comprises to control a humidity of airflow to the targeted body part.

In some embodiments, to control the airflow to the targeted body part comprises to control a temperature of airflow to the targeted body part.

According to one aspect of the disclosure, one or more computer-readable media comprising a plurality of instructions stored thereon that, when executed, causes a compute device to transmit, by one or more radar sensors, a radar signal towards a patient in a room; receive a reflection of the radar signal from the patient; receive data from the one or more radar sensors indicative of the reflection of the radar signal from the patient; and determine one or more parameters indicative of a position of the patient based on the data from the one or more radar sensors.

In some embodiments, to determine the one or more parameters indicative of the position of the patient based on the data from the one or more radar sensors comprises to determine an amount of time the patient is lying down in a patient bed; determine an amount of time the patient is sitting up in the patient bed; determine an amount of time the patient is sitting in a chair; and determine an amount of time the patient is standing or walking.

In some embodiments, the plurality of instructions further cause the compute device to determine, based on the data from the one or more radar sensors, whether the patient has an unsteady gait; and transmit, in response to a determination that the patient has an unsteady gait, an alert to a caregiver.

In some embodiments, the plurality of instructions further cause the compute device to determine, based on the data from the one or more radar sensors, whether the patient is leaving the room; and transmit, in response to a determination that the patient has left the room, an alert to a caregiver.

In some embodiments, the plurality of instructions further cause the compute device to determine, based on the data from the one or more radar sensors, whether the patient has fallen to the ground; and transmit, in response to a determination that the patient has fallen to the ground, an alert to a caregiver.

In some embodiments, to determine whether the patient has fallen to the ground comprises to determine whether the patient has fallen to the ground in a second room different from the room with the one or more radar sensors.

In some embodiments, the plurality of instructions further cause the compute device to determine one or more parameters indicative of an activity of a caregiver in the room.

In some embodiments, the one or more parameters indicative of an activity of the caregiver in the room indicate an amount of interaction of the caregiver with the patient.

In some embodiments, the one or more parameters indicative of an activity of the caregiver in the room indicate whether the caregiver washed the caregiver's hands.

In some embodiments, the one or more parameters indicative of an activity of the caregiver in the room indicate an amount of time the caregiver reviewed the medical records of the patient.

According to one aspect of the disclosure, one or more computer-readable media comprising a plurality of instructions stored thereon that, when executed, causes a compute device to present a physical therapy instruction to a patient; transmit, by one or more radar sensors, a radar signal towards the patient after presentation of the physical therapy instruction; receive a reflection of the radar signal from the patient; transmit, by one or more radar sensors, a radar signal towards the patient after presentation of the physical therapy instruction; receive, by the one or more radar sensors, a reflection of the radar signal from the patient; receive data from the one or more radar sensors indicative of the reflection of the radar signal from the patient; determine, based on the data from the one or more radar sensors, a movement parameter of the patient; and compare the movement parameter of the patient with the physical therapy instruction.

In some embodiments, to present the physical therapy instruction to the patient comprises to present the physical therapy instruction on a display, wherein the patient is in a patient bed, and wherein the display is attached to the patient bed.

In some embodiments, to present the physical therapy instruction to the patient comprises to present the physical therapy instruction on a display, and wherein the display is attached to a mobile physical therapy instruction exercise device.

In some embodiments, the plurality of instructions further cause the compute device to store performance data of the patient during an exercise session associated with the physical therapy instruction, wherein the performance data indicates a response of the patient to the physical therapy instruction.

In some embodiments, the plurality of instructions further cause the compute device to determine, based on the performance data, a second physical therapy instruction of a second exercise session different from the first.

According to one aspect of the disclosure, one or more computer-readable media comprising a plurality of instructions stored thereon that, when executed, causes a compute device to transmit, by one or more radar sensors, a radar signal towards a patient on a patient bed; receive, by the one or more radar sensors, a reflection of the radar signal from the patient; receive data from the one or more radar sensors indicative of the reflection of the radar signal from the patient; determine, based on the data from the one or more radar sensors, an indication of the patient pushing up in the bed; determine, based on the indication of the patient pushing up in the patient bed, a pressure parameter for one or more air bladders in the patient bed; and apply the pressure parameter to the one or more air bladders in the patient bed.

In some embodiments, to determine the pressure parameter for the one or more air bladders in the patient bed comprises to determine the pressure parameter for the one or more air bladders in the patient bed with use of a machine-learning-based algorithm.

In some embodiments, the plurality of instructions further cause the compute device to update a machine-learning-based algorithm based on the patient pushing up in the patient bed.

According to one aspect of the disclosure, one or more computer-readable media comprising a plurality of instructions stored thereon that, when executed, causes a compute device to transmit, by one or more radar sensors, a radar signal towards a patient in a prone position on a patient bed; receive, by the one or more radar sensors, a reflection of the radar signal from the patient; receive, by circuitry, data from the one or more radar sensors indicative of the reflection of the radar signal from the patient; determine, based on the data from the one or more radar sensors, whether there is a gap between a sternum of the patient and a surface of the patient bed while the patient is breathing in.

In some embodiments, the plurality of instructions further cause the compute device to deflate, in response to a determination that there is not a gap between a sternum of the patient and a surface of the patient bed while the patient is breathing in, one or more air bladders beneath the sternum of the patient.

In some embodiments, to determine whether there is a gap between a sternum of the patient and a surface of the patient bed while the patient is breathing in comprises to deflate one or more air bladders beneath the sternum of the patient while the patient is breathing in.

BRIEF DESCRIPTION OF THE DRAWINGS

The detailed description particularly refers to the accompanying figures, in which.

DETAILED DESCRIPTION

Figure 1:
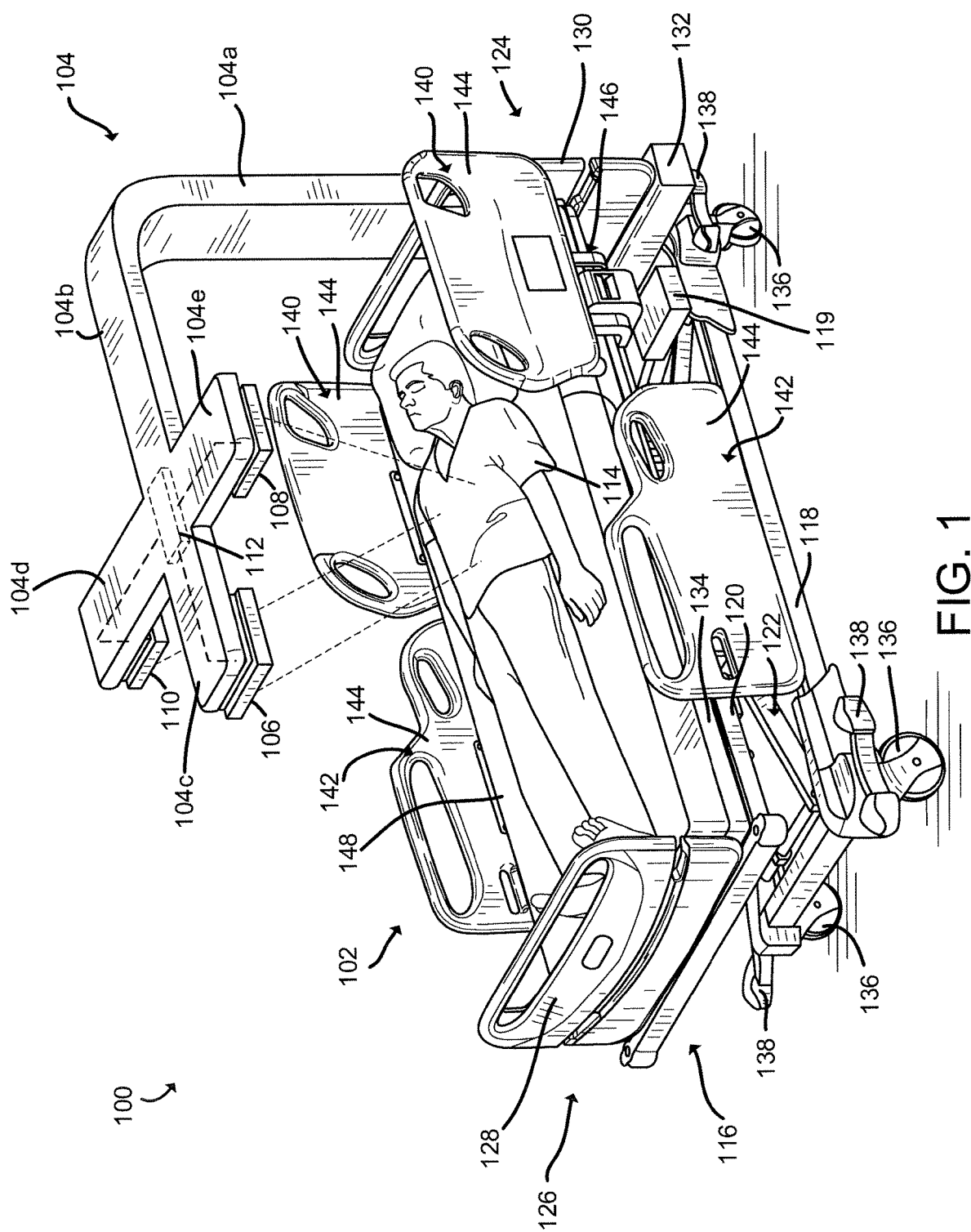
FIG. 1 is a perspective view of a system for monitoring a patient using one or more radio detection and ranging (radar) sensors.

According to some embodiments of the present disclosure, one or more radio detection and ranging (radar) apparatuses are integrated into systems such as patient support systems, hospital rooms, and physical therapy systems. The radar apparatuses are used to monitor patients, such as by monitoring position, orientation, and movement.

While all types of systems implementing the disclosed technology are contemplated herein, some examples of a patient support system include a standalone mattress system, a mattress overlay, a patient bed, a patient bed with an integrated mattress system, a surgical table, an examination table, an imaging table, a stretcher, a chair, a wheelchair, and a patient lift, just to name a few. Patient support surfaces contemplated herein include air mattresses, foam mattresses, combination air and foam mattresses, mattress overlays, surgical table pads and mattresses, stretcher pads and mattresses, chair pads, wheelchair pads, and patient lift slings and pads, just to name a few.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C): (A and B); (B and C); (A and C); or (A, B, and C). Similarly, items listed in the form of "at least one of A, B, or C" can mean (A); (B); (C): (A and B); (B and C); (A and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features Referring now to FIG. 1, a patient support system 100 includes a patient bed 102, a radar support mount 104, an abdominal radar sensor 106, a left radar sensor 108, a right radar sensor 110, and control circuitry 112. The radar sensors 106, 108, 110 monitor a patient 114 on the patient bed 102. As discussed in more detail below, the radar sensors 106, 108, 110 may monitor a patient's position, orientation, movement, etc.

Each radar sensor 106, 108, 110 may be any suitable radar sensor. In the illustrative embodiment, each radar sensor 106, 108, 110 is a millimeter-wave sensor that operates at 30-300 gigahertz (GHz). Each radar sensor 106, 108, 110 may operate over a range of frequencies, such as 60-64 GHz or 76-81 GHz. Each radar sensor 106, 108, 110 has one or more transmitter and one or more receiver. For example, each of the radar sensors 106, 108, 110 may include one or more of an AWR1843, AWR1642, AWR1443, AWR1243, IWR6843AoP, IWR6843, IWR1843, IWR1642, and/or IWR1443 chip by Texas Instruments. In some embodiments, the radar sensors 106, 108, 110 may include two or more radar chips that are cascaded together such that they operate synchronously, giving improved target detection and resolution. Additionally or alternatively, the radar sensors 106, 108, 110 may be cascaded together.

In use, each radar sensor 106, 108, 110 emits radio waves, such as millimeter waves. The radar sensors 106, 108, 110 may emit a single frequency, a series of pulses, a shaped pulse, a chirped pulse, or any other suitable wave. The waves propagate from the radar sensors 106, 108, 110 and are reflected from the patient 114 back to the radar sensors 106, 108, 110. As used herein, a reflected radar signal or reflection of a radar signal refers to a radar signal that is scattered, coherently reflected, incoherently reflected, partially reflected, etc. The reflected signals can be processed to determine a distance from the radar sensors 106, 108, 110 to one or more areas of the patient 114, such as by determining a time-of-flight or phase of the reflected signals. Multiple areas of the patient 114 can be detected as multiple reflected signals. The location of the areas reflecting the waves can be determined by the difference in reflected signals in different receivers. Additionally or alternatively, the velocity of certain areas of the patient 114 that are reflecting waves may be determined based on a Doppler shift of the reflected waves. In this way, the radar sensors 106, 108, 110 can be used to map the position and contour of the patient 114. In the illustrative embodiment, the abdominal radar sensor 106 maps the contour of the area of the patient 114 located in the center of the patient bed 102, and the left radar sensor 110 and right radar sensor 110 maps the area of the patient 114 located in the right and left parts of the patient bed 102, respectively. Additionally or alternatively, any of the radar sensors 106, 108, 110 may be used to map any area of the patient 114 in any part of the patient bed 102 or used to monitor movement or positioning of the patient or other persons in the area of the patient bed 102.

In some embodiments, multiple transmitting antennae from some or all of the radar sensors 106, 108, 110 may be operating with a controlled phase difference, allowing for beamforming. Beamforming may be used to probe a particular area of a patient 114, patient bed 102, or room.

It should be appreciated that, in some embodiments, the radio waves may penetrate some materials such as clothes, blankets, sheets, allowing for a patient 114 to be monitored under a blanket without contact.

In the illustrative embodiment, the radar support mount 104 extends over a patient bed 102. The radar support mount 104 may be attached to the patient bed 102 or may form part of a free-standing radar monitoring unit. It should be appreciated that, in some embodiments, the radar sensors 106, 108, 110 may be positioned differently from the configuration shown in FIG. 1. For example, some or all of the radar sensors 106, 108, 110 may be positioned to the side of the patient 114, on a wall of a room, embedded in the patient bed 102, and/or in any other suitable location relative to the patient 114.

The radar sensors 106, 108, 110 may be connected to the control circuitry 112 in any suitable manner. In the illustrative embodiment, one or more wires connect the radar sensors 106, 108, 110 to the control circuitry 112. Additionally or alternatively, the radar sensors 106, 108, 110 may be connected to the control circuitry 112 using fiber optics or a wireless signal. In some embodiments, the control circuitry 112 may be located next to one or more of the radar sensors 106, 108, 110 and/or may be integrated into the radar sensors 106, 108, 110. In some embodiments, some or all of the control circuitry 112 may be located in the radar support mount 104, as shown in FIG. 1. Additionally or alternatively, some or all of the control circuitry 112 may be located in any suitable location, such as in the base of the patient bed 102, in a separate component near the patient bed 102, in a remote location, etc.

The control circuitry 112 may be embodied as any circuitry capable of performing the functions described herein. For example, the control circuitry 112 may be embodied as or otherwise be included in, without limitation, an embedded computing system, a System-on-a-Chip (SoC), a multiprocessor system, a processor-based system, a consumer electronic device, a smartphone, a cellular phone, a desktop computer, a server computer, a tablet computer, a notebook computer, a laptop computer, a network device, a router, a switch, a networked computer, a wearable computer, a handset, a messaging device, a camera device, an application specific integrated circuit (ASIC), a field programmable gate array (FPGA), and/or any other computing device. The control circuitry 112 may include one or more processors, memory, one or more data storage devices, communication circuitry, and/or any other suitable component. In some embodiments, one or more of the components of the control circuitry 112 may be incorporated in, or otherwise form a portion of, another component. For example, memory, or portions thereof, may be incorporated in the processor in some embodiments. Although the control circuitry 112 is depicted as being integrated into the patient bed 102, it should be appreciated that some or all of the hardware and/or functionality of the control circuitry 112 may be embodied in a different location, such as in a computing device or circuitry in a different room or building from the patient bed 102. For example, in some embodiments, some or all of the hardware and/or functionality of the control circuitry 112 may be in a local server, a remote server, a cloud server, etc.

Still referring to FIG. 1, bed 102 includes a frame 116 that, in turn, includes a lower frame or base 118, an upper frame assembly 120, and a lift system 122 coupling upper frame assembly 120 to base 118. Lift system 122 is operable to raise, lower, and tilt upper frame assembly 120 relative to base 118. Bed 102 has a head end 124 and a foot end 126. Bed 10 further includes a footboard 128 at the foot end 126 and a headboard 130 at the head end 124. Headboard 130 is coupled to a raised portion 132 of base 28. Footboard 128 is coupled to foot end 126 of upper frame assembly 120 in the illustrative example. In other embodiments, footboard 128 is coupled to an extendable and retractable portion of a foot section of a mattress support deck 134 of upper frame assembly 120. Base 118 includes wheels or casters 136 that roll along a floor as bed 102 is moved from one location to another. A set of foot pedals 138 are coupled to base 118 and are used to brake and release casters 136 as is known in the art. Base 118 also supports a housing 119 in which portions of control circuitry, such as some or all of control circuitry 112 described herein, resides.

Illustrative hospital bed 102 has four siderail assemblies coupled to upper frame assembly 120 as shown in FIG. 1. The four siderail assemblies include a pair of head siderail assemblies 140 (sometimes referred to as head rails) and a pair of foot siderail assemblies 142 (sometimes referred to as foot rails). Each of the siderail assemblies 140, 142 is movable between a raised position, as shown in FIG. 1 with regard to both head rails 140 and the right foot rail 142, and a lowered position, as shown in FIG. 1 with regard to the left foot rail 142. Siderail assemblies 140, 142 are sometimes referred to herein as just siderails 140, 142. Each siderail 140, 142 includes a barrier panel 144 and a linkage 146. Each linkage 56 is coupled to the upper frame assembly 120 and is configured to guide the barrier panel 144 during movement of siderails 140, 142 between the respective raised and lowered positions.

Mattress support deck 134 of upper frame assembly 120 supports a mattress 148 which, in turn, supports the patient 114. Mattress support deck 134 is situated over an upper frame of upper frame assembly 120. In some embodiments, mattress support deck 134 includes articulated deck sections such as a head section that supports the head and torso regions of the patient 114, a seat section that supports the buttocks and sacral regions of the patient 114, a thigh section that supports the patient's thighs, and a foot section that supports the calves and feet of the patient 114. One or more of the deck sections are movable relative to the upper frame of upper frame assembly 120. For example, the head section pivotably raises and lowers relative to the seat section whereas foot section pivotably raises and lowers relative to the thigh section. Additionally, the thigh section articulates relative to the seat section. Also, in some embodiments, the foot section is extendable and retractable to change the overall length of the foot section and therefore, to change the overall length of mattress support deck 134. Additional details of suitable embodiments of bed 102 is found, for example, in U.S. Patent Application Publication No. 2018/0161225 A1 which is hereby incorporated by reference herein for all that teaches to the extent not inconsistent with the present disclosure which shall control as to any inconsistencies.

As noted above, bed 102 includes radar support mount 104 that, in turn, supports radar sensors 106, 108, 110. In the illustrative example, radar support mount 104 includes a generally vertically oriented column or mast 104a and a generally horizontally oriented arm 104b extending in a cantilevered manner from an upper end of mast 104a so as to overlie mattress 148 of bed 102 and the patient 114 supported thereon. Arm 104b has a distal end region 104c to which radar sensor 106 is coupled. Arm 104b is situated generally vertically above a longitudinal centerline of bed 102. Radar support mount 104 further includes right and left arms 104d, 104e that extend in a cantilevered manner from right and left sides, respectively, of arm 104b. When viewed from above, arm 104b including its distal end region 104c and arms 104d, 104e resemble a cross.

In some embodiments, radar sensors 106, 108, 110 are movable along respective arms 104b, 104d, 104e so that the trajectory of the radar beams from sensors 106, 108, 110 can be adjusted by a large or gross amount as compared to the amount of adjustment possible using beam forming techniques. For example, clamps or locks associated with each of sensors 106, 108, 110 may be manually locked and released to permit sensors 106, 108, 110 to be manually repositioned along tracks, guides, rods, bars, or the like included in respective arms 104b, 104d, 104e in some contemplated embodiments. Alternatively, sensors 106, 108, 110 may be mounted to nuts that travel along lead screws which are manually rotated by hand cranks or knobs and which are included in arms 104b, 104d, 104e. Automated or motorized control of such lead screws using motors are also contemplated by the present disclosure with regard to the manner of adjusting the positions of sensors 106, 108, 110 relative to arms 104b, 104d, 104e. Other automated adjustment mechanisms for repositioning sensors 106, 108, 110 on mount 104, such as linear actuators, motorized sprocket and chain arrangements, motorized belt and pulley arrangements, and the like are also contemplated by the present disclosure. Embodiments in which arms 104d, 104e are repositionable along arm 104b in the longitudinal dimension thereof so as to move arms 104d, 104e closer to and further from distal end region 104c of arm 104b are also within the scope of the present disclosure. Similar manual and/or automated repositioning mechanisms as those described above may be used for that purpose.

In some embodiments, a lower end of mast 104a of mount 104 is coupled to the head end 124 of the upper frame of upper frame assembly 120 of bed 102. In such embodiments, therefore, radar support mount 104 and the radar sensors 106, 108, 110 supported thereby raise, lower, and tilt relative to base 118 as upper frame assembly 120 is raised, lowered, and tilted, respectively, by lift system 122. In other embodiments, the lower end of mast 104a is coupled to the head end of base 118 of bed 102. In such embodiments, mount 104 and sensors 106, 108, 110 remain stationary as upper frame assembly 120 is raised, lowered, and tilted by lift system 122 relative to base 118. As mentioned above, in still other embodiments, mount 104 comprises a freestanding frame, such as one having casters for mobility, that is moved into position over bed 102, for example.

In some embodiments, mast 104a of mount 104 is telescopic so as to lengthen and shorten in the generally vertical direction. Thus, extending mast 104a telescopically raises arms 104b, 104d, 104e and the associated radar sensors 106, 108, 110 relative to mattress 148 and the patient 114 thereon, whereas retracting mast 104a telescopically lowers arms 104b, 104d, 104e and the associated radar sensors 106, 108, 110 relative to mattress 148 and the patient 114 thereon. In such embodiments, mast 104a includes at least first and second mast segments, if not more, that are extendable and retractable relative to each other such as with the use of one or more linear actuators, lead screw drives (manual or automatic), and the like. Optionally, arm 104b of mount 104 is telescopic to move distal end region 104c and arms 104d, 104e as a unit over the mattress 148 and patient 114 in a generally horizontal direction defined by the longitudinal dimension of arm 104b. In such embodiments, arm 104b includes at least first and second arm segments, if not more, that are extendable and retractable relative to each other such as with the use of one or more linear actuators, lead screw drives (manual or automatic), and the like. The adjustability of the locations of sensors 106, 108, 110, both generally vertically and generally horizontally, as discussed above allows the disclosed patient monitoring system using radar sensors 106, 108, 110 to account for patients of different sizes and to account for the particular position of the patient 114 on bed 102 between the head end 124 and foot end 126.

It is contemplated by the present disclosure that, in some embodiments, the portions of control circuitry 112 that control movement of portions of bed 102 communicate with the portions of circuitry 112 that controls operation of radar sensors 106, 108, 110 to alter the operation of radar sensors 106, 108, 110 under certain conditions. For example, if the head section of mattress support deck 134 is pivotably raised at a head of bed (HOB) angle that exceeds a threshold amount, say about 15 to about 30 degrees just to give an arbitrary threshold range, then use of radar sensors 106, 108, 110 may become disabled by circuitry 112 in some embodiments. This is because the inclination of the patient's torso at such steep angles may negatively affect the ability of sensors 106, 108, 110 and circuitry 112 to accurately sense the heart rate, respiration rate, and/or position of the patient. In this regard, it will be appreciated that bed 102 includes an angle sensor such as an accelerometer, inclinometer, rotary potentiometer, string potentiometer, ball switch, mercury switch, and the like that is coupled to circuitry 112 and that is used to sense the HOB angle of the head section of mattress support deck 134 of bed 102. To give another example, if circuitry 112 analyzes image intensity (e.g., lightness or darkness) of various zones of an image generated by radar sensors 106, 108, 110 and compares the light intensity to various threshold intensity values for determining the patient's position, orientation, movement, health condition, etc., it may be desirable to use different light intensity threshold values depending upon on how close the patient is to radar sensors 106, 108, 110. Thus, in some embodiments, circuitry 112 analyzes the height and/or tilt of upper frame assembly 120 relative to base 118 and/or the amount of extension or retraction of mast 104a and then adjusts the image intensity threshold values accordingly.

Figure 2:
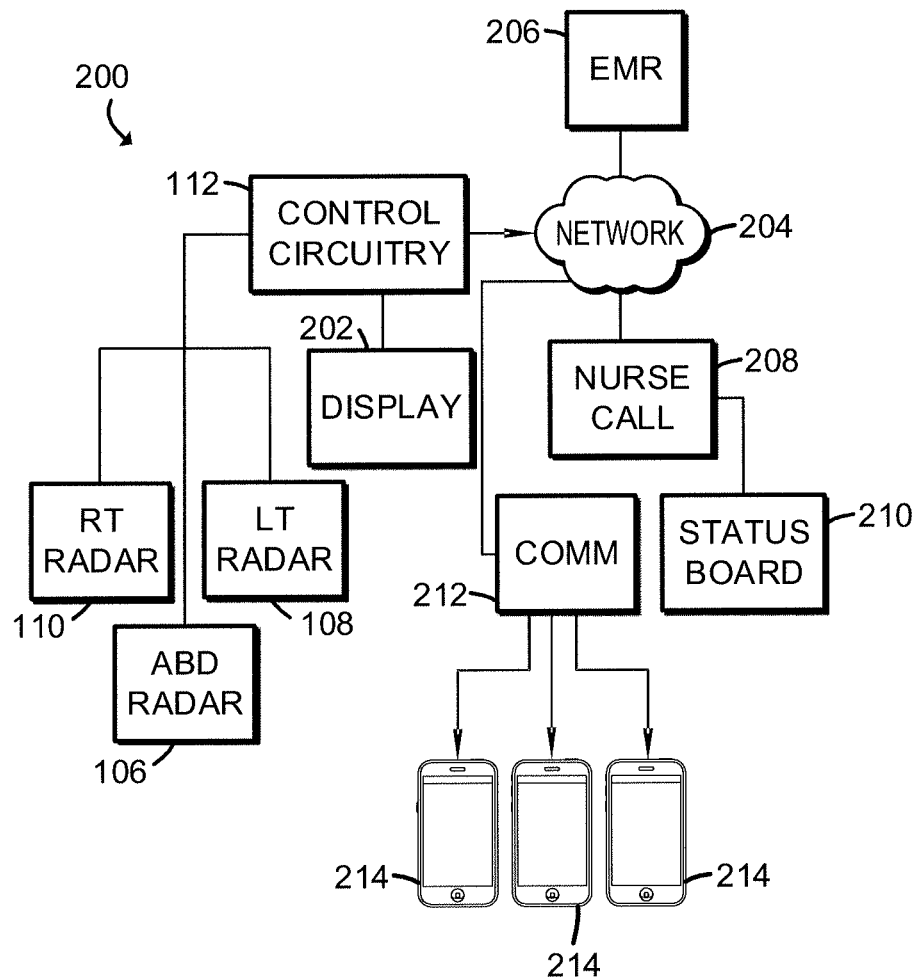
FIG. 2 is a block diagram showing one embodiment of circuitry associated with the system of FIG. 1.

Referring now to FIG. 2, a system 200 for monitoring a patient using radar sensors includes the radar sensors 106, 108, 110, the control circuitry 112, and a display 202. The control circuitry 112 may be connected over a network 204 to additional components, such as an electronic medical records server 206, a nurse call system 208, a status board 210, a communication system 212, and one or more mobile compute devices 214. In use, the control circuitry 112 may communicate monitoring information of the patient to other components of the system 200. For example, the control circuitry 112 may monitor the position of a patient 114 and send the position of the patient 114 to the electronic medical records server 206 to be stored as part of the medical record of the patient 114. The control circuitry 112 may also send the position of the patient 114 to the nurse call system 208, allowing the position to be presented on a status board 210 and/or sent to mobile compute devices 214 carried by nurses.

The display 202 may be local to the control circuitry 112, such as a display on one or more of the siderails 140, 142 of the patient bed 102. The display 202 may be any suitable display, such as an LCD display, an LED display, a laser display, and/or the like. The display 202 is operable under the control of circuitry 112 to show information, including image data, sensed by radar sensors 106, 108, 110 in some embodiments. Moreover, in some embodiments, display 202 comprises a graphical user interface (GUI) that is also operable to display user inputs for control of various features and functions of bed 102 including control of components associated with mattress 148 and control of movable portions of frame 116.

The network 204 may be any suitable network. In the illustrative embodiment, the network 204 is an Ethernet network. Additionally or alternatively, the network 204 may be embodied as a Wi-Fi® network, a Bluetooth® network, a WiMAX network, a near field communication (NFC) network, etc.

Figure 3:
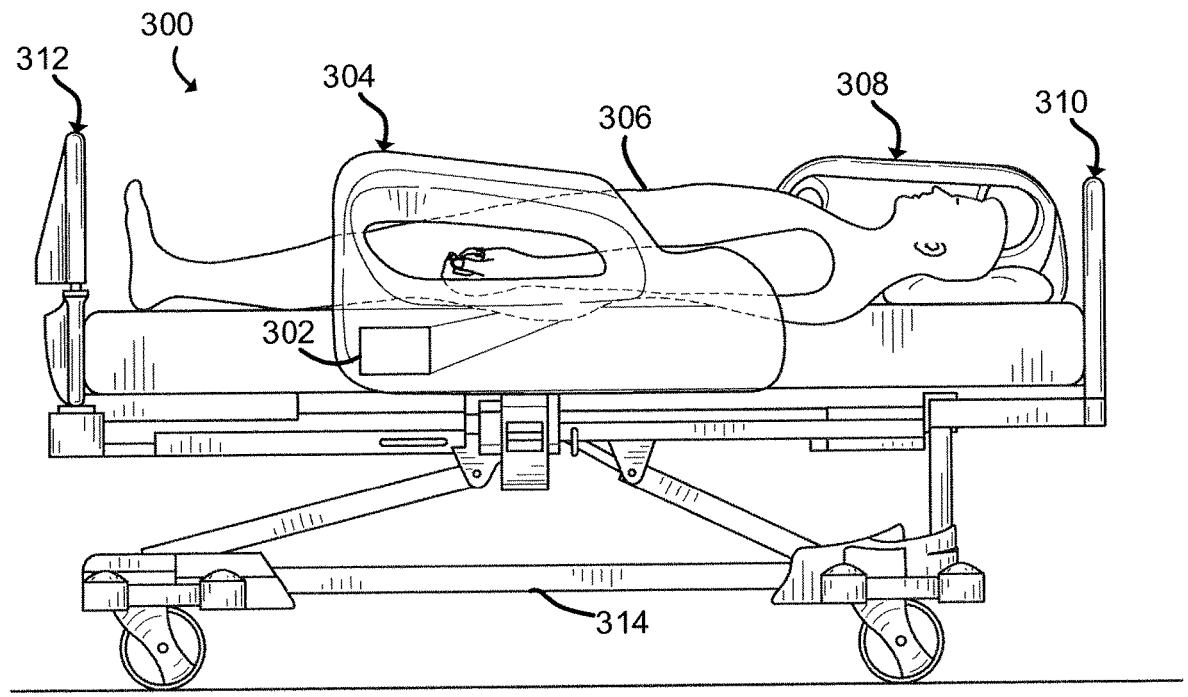
FIG. 3 is a side view of a system for monitoring a patient using one or more radar sensors.

It should be appreciated that the radar sensors 106, 108, 110 may be configured in different locations than over the patient 114 in the patient bed 102. For example, in FIG. 3, a patient bed 300 includes a radar sensor 302 positioned in or attached to a left siderail 304 of the patient bed 300 to monitor the patient 306. Additionally or alternatively, the patient bed may include a radar sensor 302 located in or attached to a right siderail 308, a headboard 310, a footboard 312, etc. The radar sensor 302 is connected to control circuitry, which may be located in any suitable position, such as in the left siderail 304, below the patient 306, such as on the lower frame or base 314 of bed 300. The radar sensor 302 (and other radar sensors discussed throughout the present disclosure) may be similar to the radar sensors 106, 108, 110, and the control circuitry associated with the radar sensor 302 (and other circuitry discussed throughout the present disclosure) may be similar to the control circuitry 112. The description of those components, and similar components described throughout the present disclosure, will not be repeated in the interest of clarity. It should be appreciated that, instead of a top-down view, the radar sensor 302 provide a side view of the patient 306. This view provides different measurement data compared to the radar sensors 106, 108, 110. It should be appreciated that any combination of radar sensor 302 and radar sensors 106, 108, and 110 may be used in various embodiments. In some embodiments, the radar sensors 302 may be used in conjunction with some or all of radar sensors 106, 108, 110, such as by measuring the same parameter such as patient contour from two different perspectives.

Figure 4:
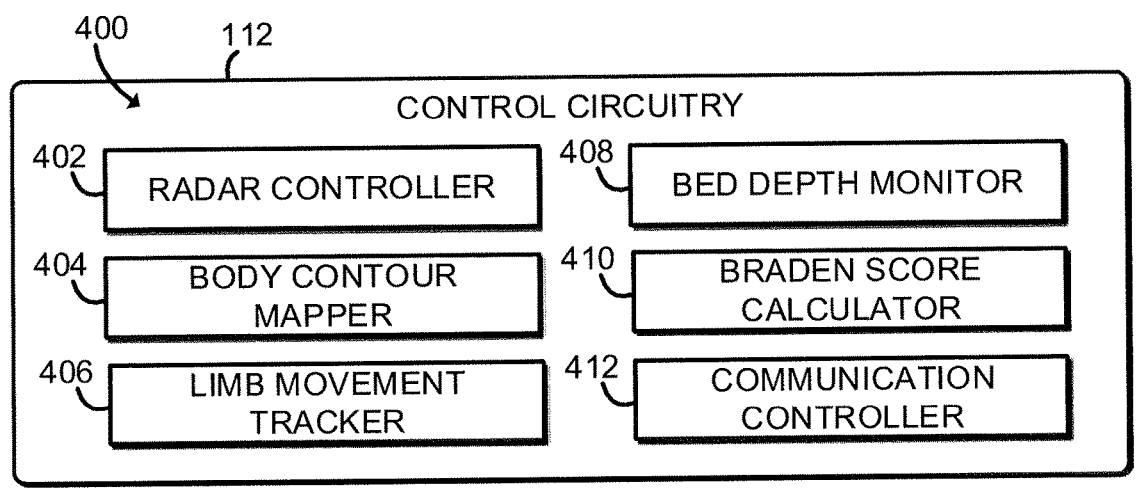
FIG. 4 is a block diagram of an environment that may be established by some or all of the circuitry of FIG. 1.

Referring now to FIG. 4, in an illustrative embodiment, the control circuitry 112 establishes an environment 400 during operation. The illustrative environment 400 includes a radar controller 402, a body contour mapper 404, a limb movement tracker 406, a bed depth monitor 408, a Braden score calculator 410, and a communication controller 412. The various modules of the environment 400 may be embodied as hardware, software, firmware, or a combination thereof. For example, the various modules, logic, and other components of the environment 400 may form a portion of, or otherwise be established by, a processor, memory, or other hardware components of the control circuitry 112. As such, in some embodiments, one or more of the modules of the environment 400 may be embodied as circuitry or collection of electrical devices (e.g., radar controller circuitry 402, body contour mapper circuitry 404, bed depth monitor circuitry 406, etc.). It should be appreciated that, in such embodiments, one or more of the circuits (e.g., the radar controller circuitry 402, the body contour mapper circuitry 404, the bed depth monitor circuitry 406, etc.) may form a portion of one or more of the processor, the memory, the data storage, and/or other components of the control circuitry 112. Additionally, in some embodiments, one or more of the illustrative modules may form a portion of another module and/or one or more of the illustrative modules may be independent of one another. Further, in some embodiments, one or more of the modules of the environment 400 may be embodied as virtualized hardware components or emulated architecture, which may be established and maintained by the processor or other components of the control circuitry 112.

The radar controller 402, which may be embodied as hardware, firmware, software, virtualized hardware, emulated architecture, and/or a combination thereof as discussed above, is configured to interface with the radar sensors 106, 108, 110, 302. The radar controller 402 may send commands to the radar sensors 106, 108, 110, 302, configure the radar sensors 106, 108, 110, 302, and receive data from the radar sensors 106, 108, 110, 302. In the illustrative embodiment, the radar controller 402 receives indications of the signals received by the radar sensors 106, 108, 110, 302, such as the intensity, phase, electric field, etc., received at each receiver of the radar sensors 106, 108, 110, 302. In some embodiments, the radar sensors 106, 108, 110, 302 may perform some pre-processing before sending data to the radar controller 402, such as by processing data received to determine the location and/or velocity of objects that reflected waves to the radar sensors 106, 108, 110, 302.

The body contour mapper 404, which may be embodied as hardware, firmware, software, virtualized hardware, emulated architecture, and/or a combination thereof as discussed above, is configured to map the contour of the body of the patient. The body contour mapper 404 may generate a 2D or 3D map of the body of the patient, which can be used to determine a patient's position, orientation, and movement.

The limb movement tracker 406, which may be embodied as hardware, firmware, software, virtualized hardware, emulated architecture, and/or a combination thereof as discussed above, is configured to track the movement of the limbs of the patient. The limb movement tracker 406 may track arms, legs, and head of the patient. In some embodiments, the limb movement tracker 406 may track the movement of individual fingers of the patient.

The limb movement tracker 406 may monitor a patient for a lack of motion as well as motion over a time frame. The movement of the limbs of the patient as well as the movement of the patient overall can be compared to a baseline of a "normal" person and/or compared to the "normal" behavior of that patient. If the movement is above or below baseline by a certain percentage, an alert may be sent to a caregiver. Lack of movement could potentially indicate a higher risk for skin wounds, urinary tract infection, pneumonia, etc. Excessive movement can be indicative of periodic limb movements disorder (PLMD) or other conditions that could require treatment. In some embodiments, the limb movement tracker 406 may detect a seizure of the patient and may alert a caregiver accordingly. The limb movement tracker 406 may monitor a patient over a long period of time, such as over several days or months in a long-term care facility. The limb movement tracker 406 may determine a baseline amount of movement for the patient and may track trends in changes in movement over a period of days, weeks or months. Changes in the trend of patient movement may indicate a change in the condition of the patient.

The bed depth monitor 408, which may be embodied as hardware, firmware, software, virtualized hardware, emulated architecture, and/or a combination thereof as discussed above, is configured to monitor the bed depth of the patient. In the illustrative embodiment, the bed depth monitor 408 may determine a bed depth of several areas of the patient, such as back, sacrum, legs, and heel. Additionally or alternatively, the bed depth monitor 408 may determine an overall or average bed depth.

The Braden score calculator 410, which may be embodied as hardware, firmware, software, virtualized hardware, emulated architecture, and/or a combination thereof as discussed above, is configured to determine a Braden score of the patient. The Braden score can be based at least partially on data from the radar sensors 106, 108, 110, 302. For example, the Braden score calculator 410 can determine the degree of physical activity of the patient, the mobility of the patient, and friction and shear forces experienced by the patient based on data from the radar sensors 106, 108, 110, 302. In some embodiments, the Braden score calculator 410 may determine a Braden score at least partially based on input from a caregiver, such as the ability of the patient to respond to pressure-related discomfort, the degree to which skin is exposed to moisture and food intake pattern. As used herein, the phrase "based on" includes both "partially based on" and "entirely based on."

The communication controller 412 is configured to communicate with other devices, such as the electronic medical records server 206 or the nurse call system 208. As discussed above, the communication controller 412 may communicate with other devices directly or indirectly through, for example, Ethernet, Bluetooth®, Wi-Fi®, WiMAX, near field communication (NFC), etc.

Figure 5:
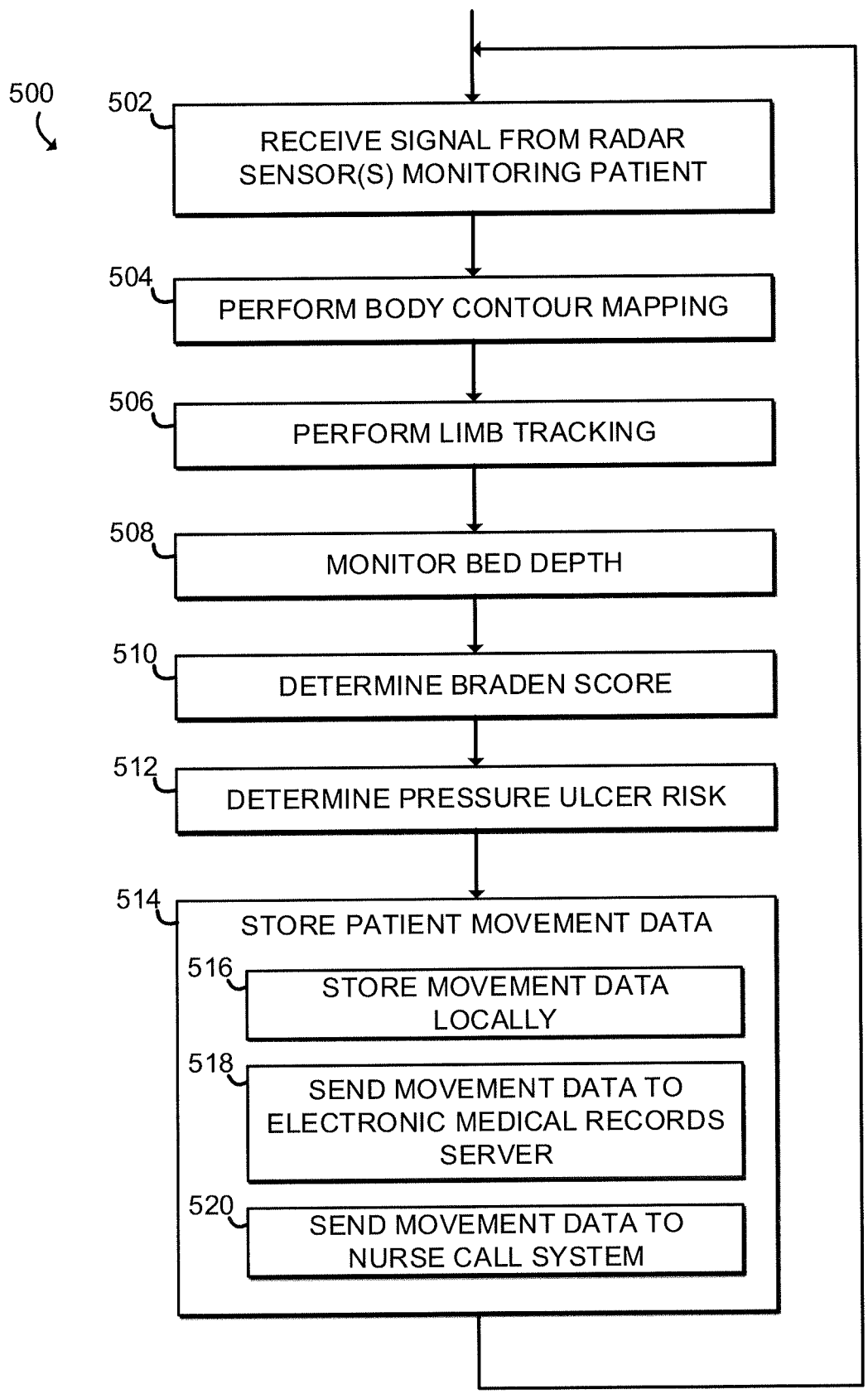
FIG. 5 is a flow chart of one embodiment of a method to monitor patient movement in one of the systems of FIGS. 1-3.

Referring now to FIG. 5, in use, a method 500 for monitoring a patient with radar may be performed. In some embodiments, some or all of the method 500 may be performed by the control circuitry 112. Additionally or alternatively, in some embodiments, the control circuitry 112 may provide data such as a patient movement frequency, and a caregiver may monitor the data from the control circuitry 112 to determine, e.g., a Braden score for the patient. The method 500 begins in block 502, in which the control circuitry 112 receives a signal from one or more radar sensors 106, 108, 110 monitoring a patient's position, orientation, and/or movement. The control circuitry 112 may receive the raw signal received by an antenna of a radar sensor 106, 108, 110. In some embodiments, the radar sensors 106, 108, 110 may perform some pre-processing before sending data to the control circuitry 112, such as by processing data received to determine the location and/or velocity of objects that reflected waves to the radar sensors 106, 108, 110.

In block 504, the control circuitry 112 analyzes the radar signal to perform a body contour mapping of the patient. The control circuitry 112 may generate a 2D or 3D map of the body of the patient, which can be used to determine a patient's position, orientation, and movement.

In block 506, the control circuitry 112 performs limb tracking and may track the arms, legs, and head of the patient. In some embodiments, the control circuitry 112 may track the movement of individual fingers of the patient.

In block 508, the control circuitry 112 monitors the bed depth of the patient. In the illustrative embodiment, the control circuit 112 may determine a bed depth of several areas of the patient, such as back, sacrum, legs, and heel. Additionally or alternatively, the control circuit 112 may determine an overall or average bed depth.

In block 510, the control circuitry 112 determines a Braden score of the patient. The Braden score can be based at least partially on data from the radar sensors 106, 108, 110, 302. For example, the control circuitry 112 can determine the degree of physical activity of the patient, the mobility of the patient, and friction and shear forces experienced by the patient based on data from the radar sensors 106, 108, 110, 302. In some embodiments, the control circuitry 112 may determine a Braden score at least partially based on input from a caregiver, such as the ability of the patient to respond to pressure-related discomfort, the degree to which skin is exposed to moisture and food intake pattern.

In block 512, the control circuitry 112 determines a pressure ulcer risk. The control circuitry 112 may determine a pressure ulcer risk based on various factors such as the Braden score, the bed depth of a particular area of the patient's body, how long a particular area of the patient's body has been under pressure, etc. In some embodiments, the control circuitry 112 may use a machine-learning-based algorithm to determine a pressure ulcer risk based on some or all of those factors. Such a machine-learning-based algorithm can be trained based on data of past patients from radar sensors similar to radar sensors 106, 108, 110, 302. Data from a patient in combination with a label of the presence or absence of a pressure sore based on a caregiver's assessment can be used as labeled training data for a machine-learningbased algorithm. The machine-learning-based algorithm may be trained by the control circuitry 112 or any other suitable computing device.

In block 514, the control circuitry 112 stores patient movement data and/or additional data such as Braden score and pressure ulcer risk. The control circuitry 112 may store the patient data locally in block 516, which can then be used to determine, e.g., if there is a change in a rate of a patient's movement. Additionally or alternatively, in some embodiments, the control circuitry 112 may send patient data to an electronic medical records server in block 518 and/or send patient data to a nurse call system in block 520. The method 500 then loops back to block 502 to receive additional data from radar sensors 106, 108, 110.

Figure 6:
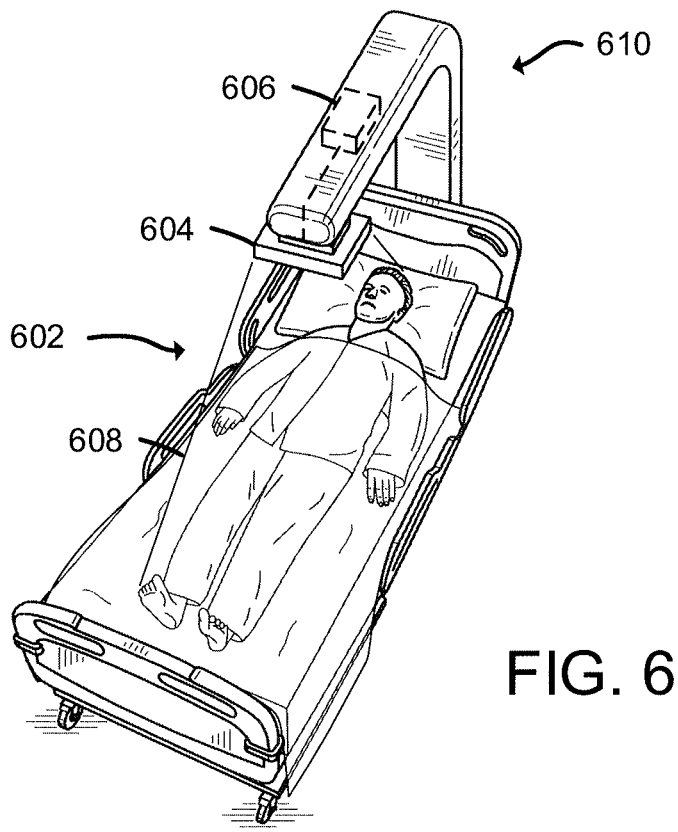
FIG. 6 is a perspective view of a system for monitoring a patient using one or more radar sensors.

In another configuration, as shown in FIG. 6, a patient bed 602 may have one or more radar sensors 604 connected to control circuitry 608 located over the center of the patient 608 without any radar sensors on the sides. Bed 602 of FIG. 6 is substantially the same as bed 102 of FIG. 1 and so the discussion above of bed 102 is equally applicable to bed 602. Furthermore, a radar support mount 610 is used in connection with bed 602 in the same manner as discussed above in connection with mount 104 used with bed 102. Thus, the discussion above of mount 104, including all of the variants thereof, is equally applicable to mount 610. Thus, for example, mount 610 includes a generally vertically oriented column or mast 610a and a generally horizontal arm 610b having a distal end region 610c to which radar sensor 604 is coupled. The discussion above of mast 104a is equally applicable to mast 604a and the discussion above of arm 104b is equally applicable to arm 604b. It should be appreciated that, in some embodiments, the frequency used by the radar sensor 604 may pass through certain materials such as blankets, allowing clear monitoring of a patient's movement even when the patient is covered by blankets.

Figure 7:
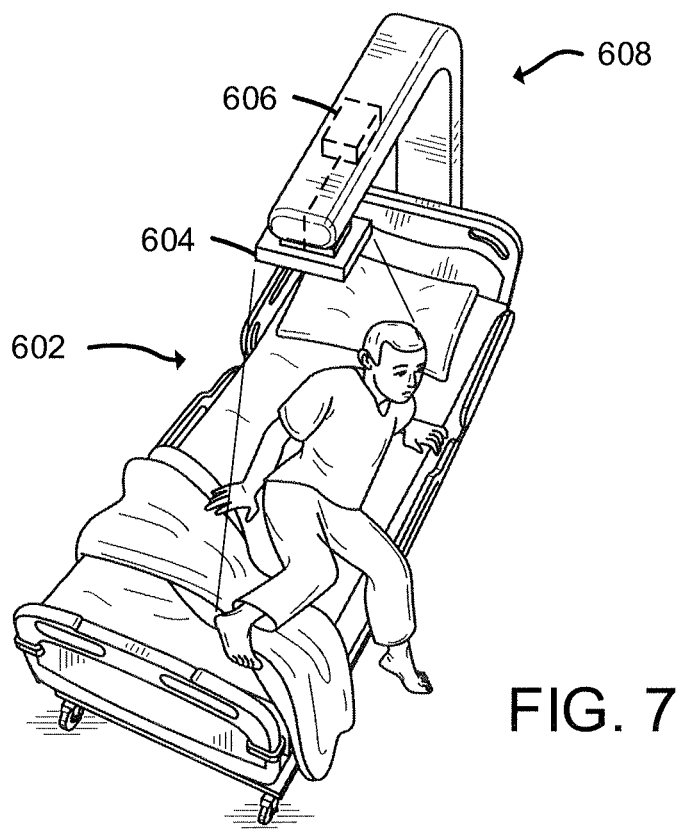
FIG. 7 is a perspective view of a system for monitoring a patient exiting a bed using one or more radar sensors.

As shown in FIG. 7, the radar sensor 604 can monitor a patient who is exiting the bed 602. The control circuitry 608 can be used to monitor the patient before and during a bed exit, and can predict that a bed exit may be happening and alert a caregiver, as described in more detail below.

Figure 8:
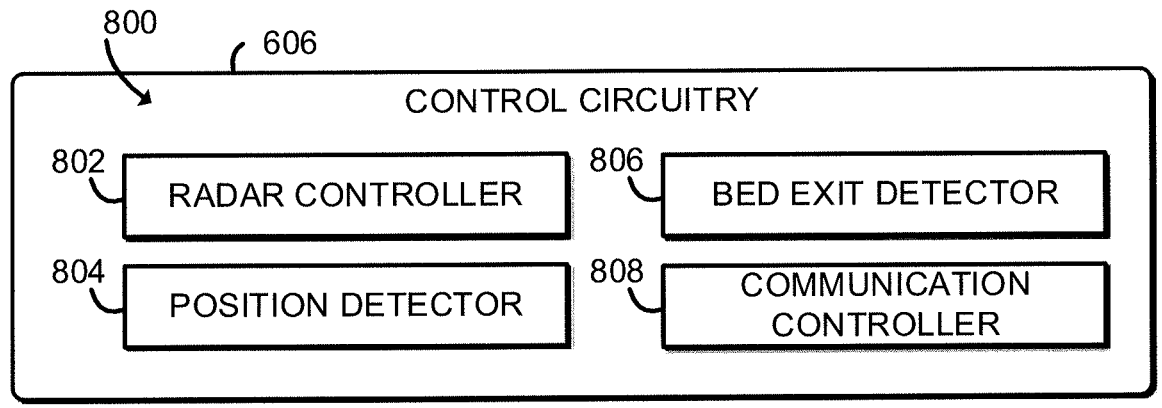
FIG. 8 is a block diagram of an environment that may be established by some or all of the circuitry of FIG. 6 or 7.

Referring now to FIG. 8, in an illustrative embodiment, the control circuitry 606 establishes an environment 800 during operation. The illustrative environment 800 includes a radar controller 802, a position detector 804, a bed exit detector 806, and a communication controller 808. The various modules of the environment 800 may be embodied as hardware, software, firmware, or a combination thereof. For example, the various modules, logic, and other components of the environment 800 may form a portion of, or otherwise be established by, a processor, memory, or other hardware components of the control circuitry 606. As such, in some embodiments, one or more of the modules of the environment 800 may be embodied as circuitry or collection of electrical devices (e.g., radar controller circuitry 802, position detector circuitry 804, bed exit detector circuitry 806, etc.). It should be appreciated that, in such embodiments, one or more of the circuits (e.g., the radar controller circuitry 802, the position detector circuitry 804, the bed exit detector circuitry 806, etc.) may form a portion of one or more of the processor, the memory, the data storage, and/or other components of the control circuitry 606. Additionally, in some embodiments, one or more of the illustrative modules may form a portion of another module and/or one or more of the illustrative modules may be independent of one another. Further, in some embodiments, one or more of the modules of the environment 800 may be embodied as virtualized hardware components or emulated architecture, which may be established and maintained by the processor or other components of the control circuitry 606.

The radar controller 802, which may be embodied as hardware, firmware, software, virtualized hardware, emulated architecture, and/or a combination thereof as discussed above, is configured to interface with the radar sensor 604. The radar controller 802 may send commands to the radar sensor 604, configure the radar sensor 604, and receive data from the radar sensor 604. In the illustrative embodiment, the radar controller 802 receives indications of the signals received by the radar sensor 604 such as the intensity, phase, electric field, etc., received at each receiver of the radar sensor 604. In some embodiments, the radar sensor 604 may perform some pre-processing before sending data to the radar controller 802, such as by processing data received to provide an indication of the position or movement of the patient.

The position detector 804, which may be embodied as hardware, firmware, software, virtualized hardware, emulated architecture, and/or a combination thereof as discussed above, is configured to determine a position of the patient. The position detector 804 may determine a 2D or 3D position of various parts of the patient, such as torso, arms, legs, head, etc.

The bed exit detector 806, which may be embodied as hardware, firmware, software, virtualized hardware, emulated architecture, and/or a combination thereof as discussed above, is configured to detect a bed exit or predict a future bed exit by the patient. For example, in some embodiments, the bed exit detector 806 may determine that a patient is moving in such a manner that is consistent with attempting to get out of bed soon, such as by drawing the patient's knees towards the patient's chest and turning towards a side of the bed. Detection of a patient exiting the bed may be useful in several cases, such as to alert caregivers to assist the patient, to alert caregivers to monitor the patient out of bed, to alert caregivers if the patient is out of bed too long, etc.

The communication controller 808 is configured to communicate with other devices, such as the electronic medical records server 206 or the nurse call system 208. The communication controller 808 may communicate with other devices directly or indirectly through, for example, Ethernet, Bluetooth®, Wi-Fi®, WiMAX, near field communication (NFC), etc. The communication controller 808 may transmit data indicating the patient's position. The communication controller 808 may send an alert or notification to, e.g., the electronic medical records server 206 or the nurse call system 208 that a patient is or is predicted to exit the bed.

Figure 9:
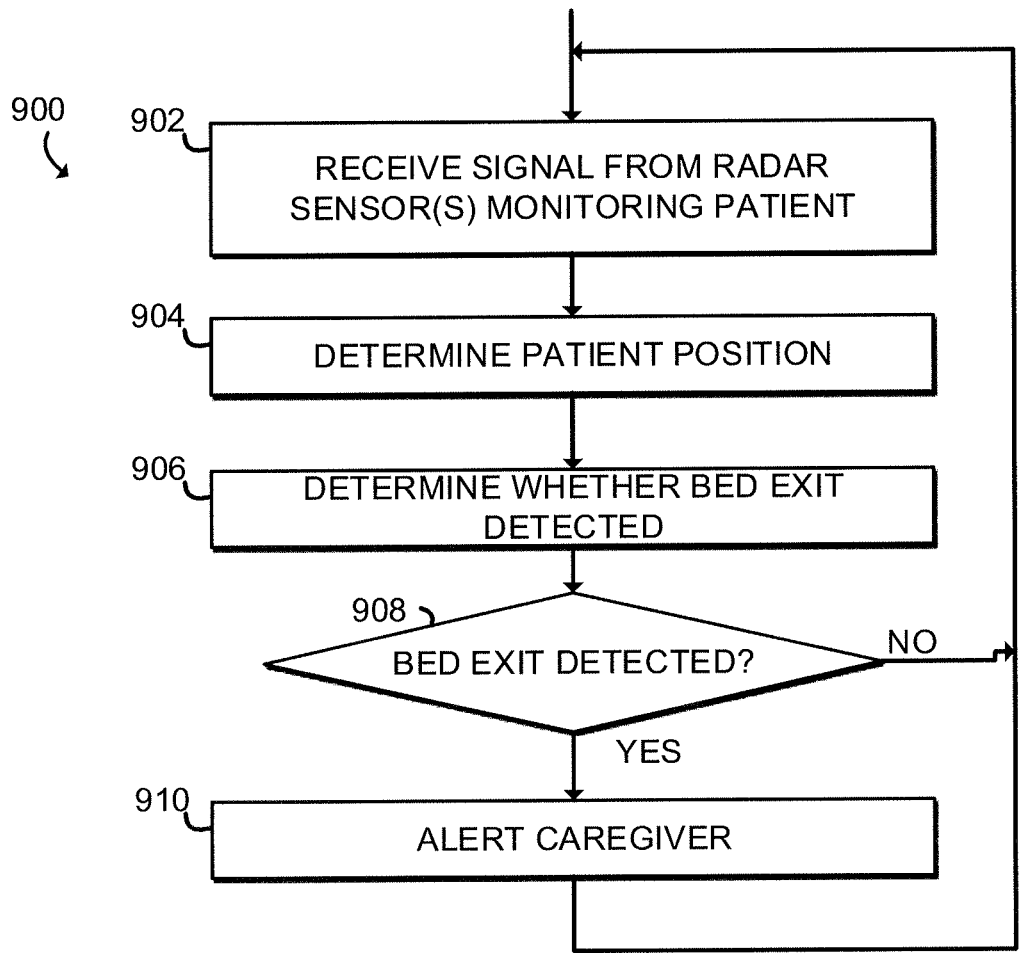
FIG. 9 is a flow chart of one embodiment of a method to monitor a patient for bed exit in one of the systems of FIG. 6 or 7.

Referring now to FIG. 9, in use, a method 900 for monitoring a patient with radar may be performed. In some embodiments, some or all of the method 900 may be performed by the control circuitry 606. The method 900 begins in block 902, in which the control circuitry 606 receives a signal from one or more radar sensors 604 monitoring a patient's position. The control circuitry 606 may receive the raw signal received by an antenna of a radar sensor 640. In some embodiments, the radar sensors 604 may perform some pre-processing before sending data to the control circuitry 606.

In block 904, the control circuitry 606 determines a position of the patient. The control circuitry 606 may determine a 2D or 3D position of various parts of the patient, such as torso, arms, legs, head, etc.

In block 906, the control circuitry 606 determines whether a bed exit is detected and/or whether a future bed exit is predicted. For example, in some embodiments, the control circuitry 606 may determine that a patient is moving in such a manner that is consistent with attempting to get out of bed soon, such as by drawing the patient's knees towards the patient's chest and turning towards a side of the bed.

In block 906, if a bed exit is not detected, the method 900 loops back to block 902 to continue monitoring of the patient. If a bed exit is detected, the method 900 continues to block 910, in which the control circuitry 606 alerts a caregiver, such as by sending a message to a nurse call station 208 or a status board 210. Detection of a patient exiting the bed may be useful in several cases, such as to alert caregivers to assist the patient, to alert caregivers to monitor the patient out of bed, to alert caregivers if the patient is out of bed too long, etc. The method 900 then loops back to block 902 to continue monitoring the patient.

Referring now to FIGS. 10-13, in one embodiment, a patient bed 1002 includes one or more radar sensors 1004 connected to control circuitry 1006. In the illustrative example, radar support mount 1008 is used to support the one or more radar sensors 1004 and circuitry 1006. Mount 610 was discussed above in connection with FIG. 6 and the discussion is equally applicable to the use of mount 1008 with bed 1002 of FIGS. 10-13.

Figure 10:
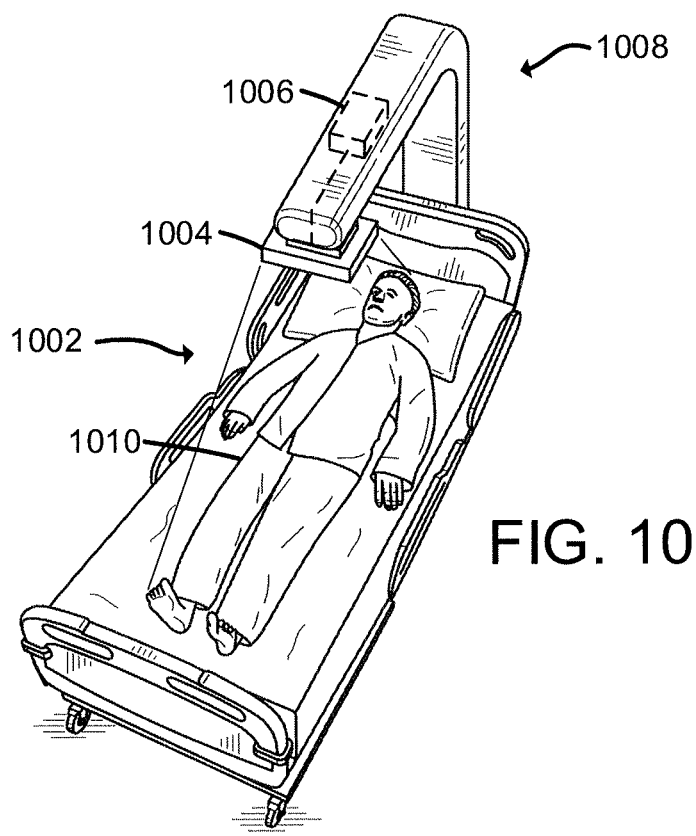
FIG. 10 is a perspective view of a system for monitoring a patient using one or more radar sensors.
Figure 11:
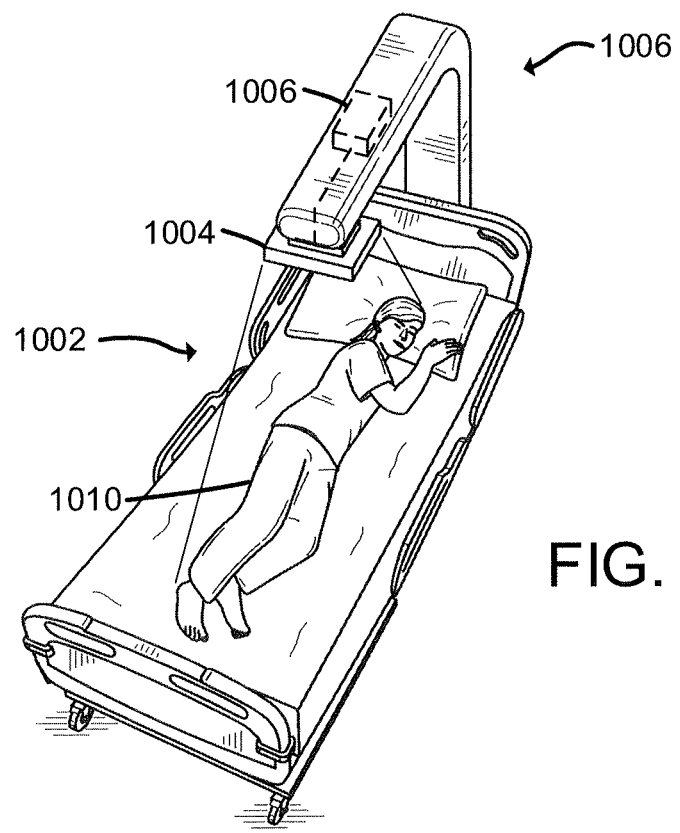
FIG. 11 is a perspective view of a system for monitoring a patient using one or more radar sensors.

In use, the control circuitry 1006 may be configured to monitor a position of the patient using the radar sensor 1004 and determine when a turning of the patient may be necessary. The radar sensor 1004 can be used to both determine when the patient moves and to determine where a patient is. For example, the radar sensor 1004 may be used to determine that a patient 1010 is lying on his back, as shown in FIG. 10, and may be used to determine that a patient 1010 is lying on her side, as shown in FIG. 11.

Figure 12:
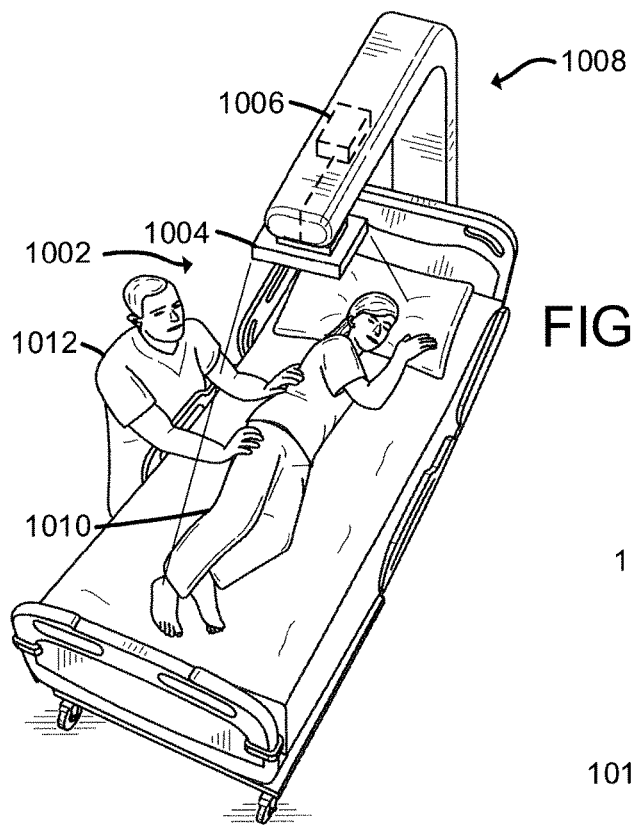
FIG. 12 is a perspective view of a system for monitoring a rotation of patient by a caregiver using one or more radar sensors.
Figure 13:
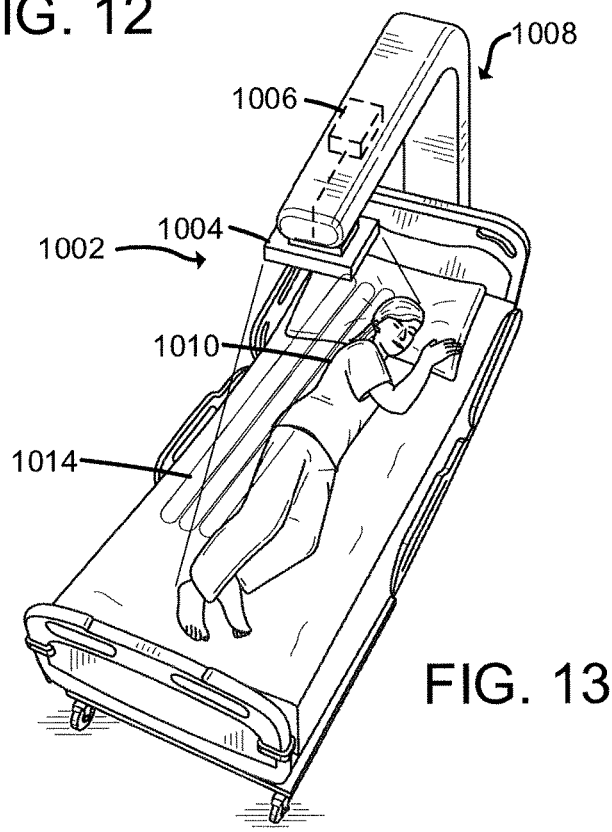
FIG. 13 is a perspective view of a system for monitoring a rotation of patient by a bladders of a hospital bed using one or more radar sensors.

If a patient 1010 has not rotated within a certain amount of time, such as the past two hours, the control circuitry 1006 may alert a caregiver 1012, who can then manually turn the patient, as shown in FIG. 12. The turn of the patient can be detected by the control circuitry 1006 using the radar sensor 1004, restarting a timer for when the patient should be turned. In some embodiments, as shown in FIG. 13, the control circuitry 1006 may inflate air rotation bladders 1014 to cause the patient to rotate from a supine position to the patient's side (or deflate the rotation bladders 1014 to rotate the patient back to a supine position). In some embodiments, the control circuitry 1006 may be configured to determine a position of the patient on the bed using the radar sensor 1004, and then inflate the rotation bladders 1014 that would cause the most rotation, such as the rotation bladders 1014 that are under the patient's right side if the patient is to be rotated on her left side, as shown in FIG. 13. Additionally or alternatively, the rotation bladders 1014 can be used to reposition a patient to a desired position.

Figure 14:
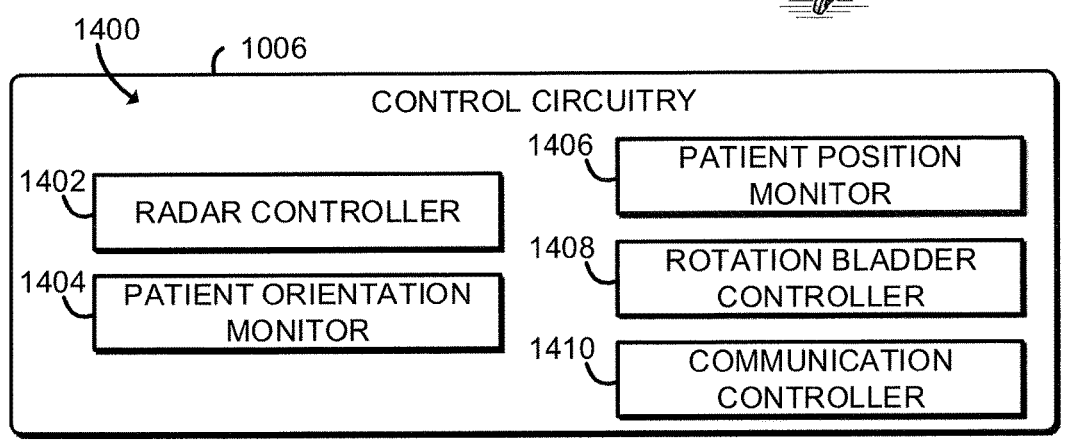
FIG. 14 is a block diagram of an environment that may be established by some or all of the circuitry of FIGS. 10-13.

Referring now to FIG. 14, in an illustrative embodiment, control circuitry 1006 establishes an environment 1400 during operation. The illustrative environment 1400 includes a radar controller 1402, a patient orientation monitor 1404, a patient position monitor 1406, a rotation bladder controller 1408, and a communication controller 1410. The various modules of the environment 1400 may be embodied as hardware, software, firmware, or a combination thereof. For example, the various modules, logic, and other components of the environment 1400 may form a portion of, or otherwise be established by, a processor, memory, or other hardware components of the control circuitry 1400. As such, in some embodiments, one or more of the modules of the environment 1400 may be embodied as circuitry or collection of electrical devices (e.g., radar controller circuitry 1402, patient orientation monitor circuitry 1404, patient position monitor circuitry 1406, etc.). It should be appreciated that, in such embodiments, one or more of the circuits (e.g., the radar controller circuitry 1402, the patient orientation monitor circuitry 1404, the patient position monitor circuitry 1406, etc.) may form a portion of one or more of the processor, the memory, the data storage, and/or other components of the control circuitry 1006. Additionally, in some embodiments, one or more of the illustrative modules may form a portion of another module and/or one or more of the illustrative modules may be independent of one another. Further, in some embodiments, one or more of the modules of the environment 1400 may be embodied as virtualized hardware components or emulated architecture, which may be established and maintained by the processor or other components of the control circuitry 1006.

The radar controller 1402, which may be embodied as hardware, firmware, software, virtualized hardware, emulated architecture, and/or a combination thereof as discussed above, is configured to interface with the radar sensor 1004. The radar controller 1402 may send commands to the radar sensor 1004, configure the radar sensor 1004, and receive data from the radar sensor 1004. In the illustrative embodiment, the radar controller 1402 receives indications of the signals received by the radar sensor 1004 such as the intensity, phase, electric field, etc., received at each receiver of the radar sensor 1004. In some embodiments, the radar sensor 1004 may perform some pre-processing before sending data to the radar controller 1402, such as by processing data received to provide an indication of the position or movement of the patient.

The patient orientation monitor 1404, which may be embodied as hardware, firmware, software, virtualized hardware, emulated architecture, and/or a combination thereof as discussed above, is configured to monitor the orientation of the patient on a patient bed with use of one or more radar sensors. The patient orientation monitor 1404 may monitor whether the patient is supine, prone, on the patient's side, etc. The patient orientation monitor 1404 saves the patient orientation data over time, allowing for determination of how long a patient has been lying in the same orientation. The orientation determined by the patient orientation monitor 1404 may be used as feedback for controlling the rotation bladders 1014.

The patient position monitor 1406, which may be embodied as hardware, firmware, software, virtualized hardware, emulated architecture, and/or a combination thereof as discussed above, is configured to monitor the position of the patient on a patient bed with use of one or more radar sensors. The patient position monitor 1406 may monitor the position of the patient, such as where the patient is on the patient bed and where the patient is relative to the rotation bladders 1014. The position determined by the patient position monitor 1406 may be used as feedback for controlling the rotation bladders 1014.

The rotation bladder controller 1408, which may be embodied as hardware, firmware, software, virtualized hardware, emulated architecture, and/or a combination thereof as discussed above, is configured to control the rotation bladders 1014. The rotation bladder controller 1408 may determine when a rotation is necessary, such as by determining that the patient has been lying on the same side for an amount of time that is past a threshold amount of time. The threshold may be any suitable value, such as any time between 30 minutes and 5 hours, for example. In the illustrative embodiment, the threshold is 2 hours. Additionally or alternatively, in some embodiments, the rotation bladder controller 1408 may determine whether the patient should be rotated to prevent laryngopharyngeal reflux and/or determine whether the patient should be rotated to prevent pulmonary complications. For example, in some embodiments, the rotation bladder controller 1408 may control the rotation bladders 1014 to alternately elevate one lung relative to the other.

In some embodiments, the rotation bladder controller 1408 may determine where the patient is on the patient bed, and control the rotation bladders 1014 that will cause the patient to rotate from their current position. For example, the rotation bladder controller 1408 may cause the rotation bladders that are under the right side of the patient to inflate. In some embodiments, the rotation bladder controller 1408 may control the rotation bladders 1014 to cause the patient to move position, which may be done to, e.g., position the patient over a desired portion of the rotation bladders 1014.

The communication controller 1410 is configured to communicate with other devices, such as the electronic medical records server 206 or the nurse call system 208. The communication controller 140 may communicate with other devices directly or indirectly through, for example, Ethernet, Bluetooth®, Wi-Fi®, WiMAX, near field communication (NFC), etc. The communication controller 1410 may be used to transmit data of the patient's position and orientation. The communication controller 1410 may send an alert or notification to, e.g., the electronic medical records server 206 or the nurse call system 208 that a patient needs to be rotated or has been rotated.

Figure 15:
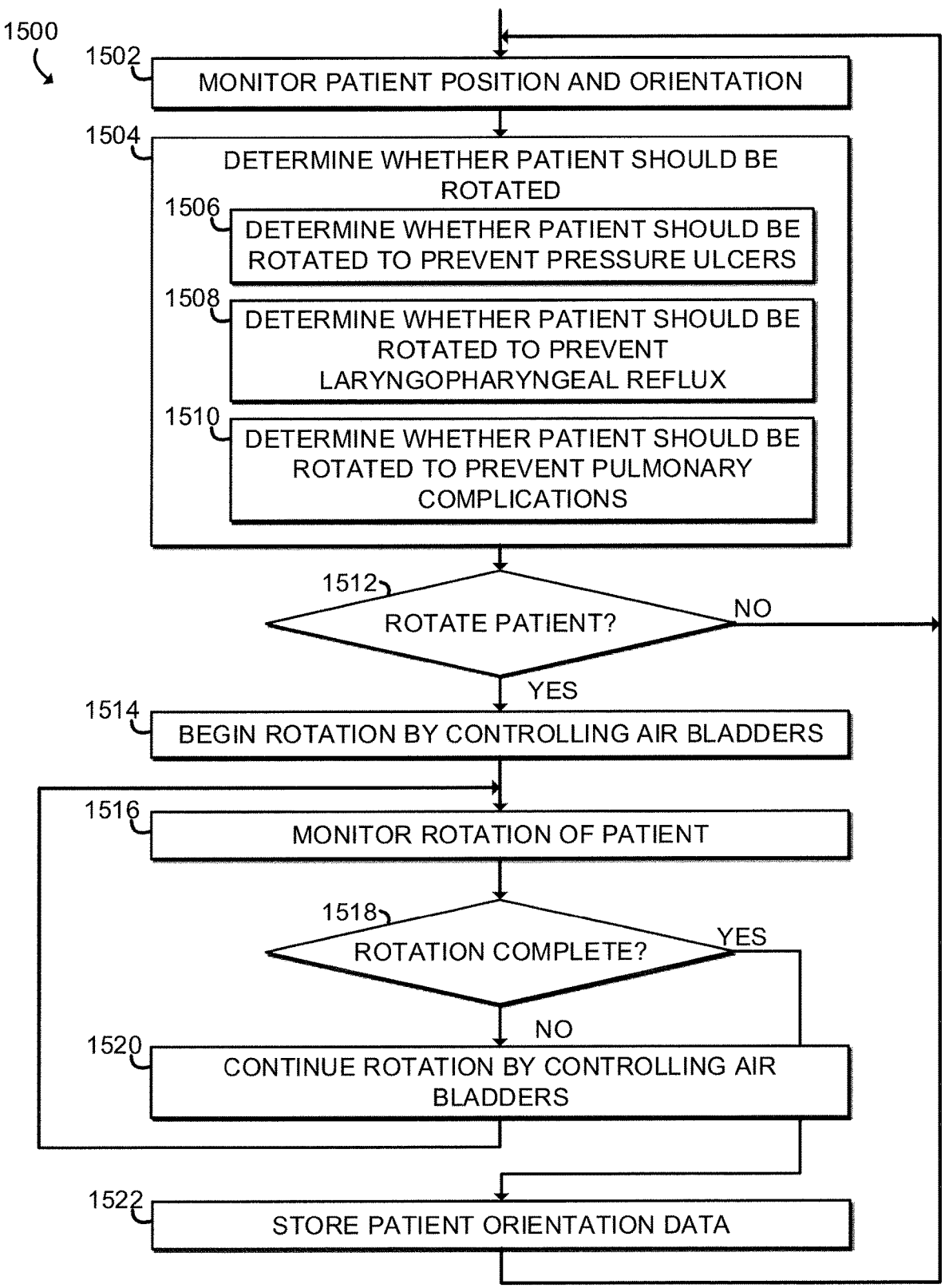
FIG. 15 is a flow chart of one embodiment of a method to monitor rotation of a patient in one of the systems of FIGS. 10-13.
Figure 16:
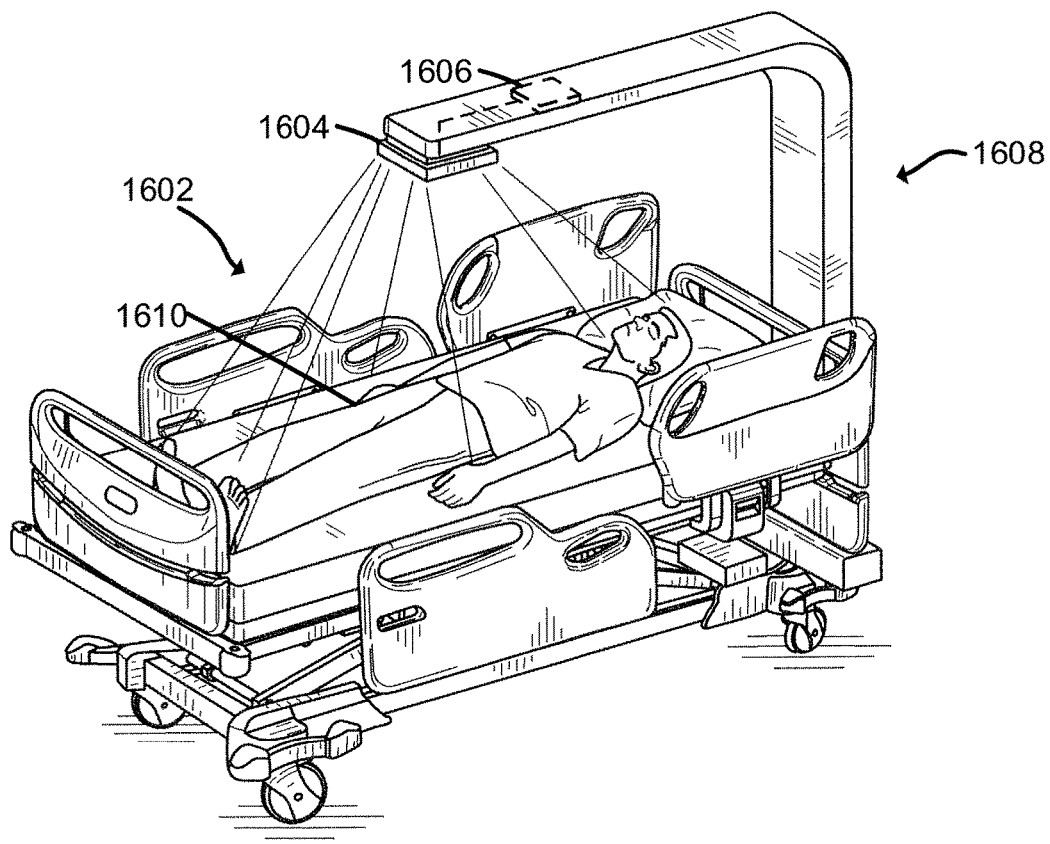
FIG. 16 is a perspective view of a system for monitoring a patient using one or more radar sensors.

Referring now to FIG. 15, in use, a method 1500 for rotating a patient may be performed. In some embodiments, some or all of the method 1500 may be performed by the control circuitry 1006. Additionally or alternatively, in some embodiments, certain portions of the method 1500 may be performed a person, such as a caregiver of the patient. For example, the control circuitry 1006 may indicate that a patient has changed orientation for a certain period of time, and a caregiver may rotate the patient in response to that indication. In another example, a caregiver may determine that a patient needs to be rotated and may initiate the rotation by the control circuitry 1006. The method 1500 begins in block 1502, in which the control circuitry 1006 monitors the patient position and orientation. The control circuitry 1006 may monitor whether the patient is supine, prone, on the patient's side, etc. The control circuitry 1006 may monitor the position of the patient, such as where the patient is on the patient bed and where the patient is relative to the rotation bladders 1014.

In block 1504, the control circuitry 1006 determines whether the patient should be rotated. In block 1506, the control circuitry 1006 determines whether the patient should be rotated to prevent pressure ulcers based on whether the patient has changed orientation in a predetermined period of time, such as the last two hours. In block 1508, the control circuitry 1006 may determine whether the patient should be rotated to prevent laryngopharyngeal reflux. In block 1510, the control circuitry 1006 may determine whether the patient should be rotated to prevent pulmonary complications. For example, in some embodiments, control circuitry 1006 may control the rotation bladders 1014 to alternately elevate one lung relative to the other.

In block 1512, if the patient is not to be rotated, the method 1500 loops back to block 1502 to continue monitoring the patient position and orientation. If the patient is to be rotated, the method proceeds to block 1514, in which the rotation bladders 1014 under one side of the patient are inflated. The rotation bladders 1014 to be inflated may be selected based on a position of the patient that can be determined based on one or more radar sensors. It should be appreciated that, in some embodiments, the patient may be rotated by deflating the rotation bladders 1014, such as when the patient has already been rotated by inflation of the rotation bladders 1014.

In block 1516, the rotation of the patient is monitored. In some embodiments, the rotation of the patient is monitored with use of one or more radar sensors. In block 1518, if the rotation is not complete, the method 1500 proceeds to block 1520 to continue the rotation by controlling the rotation bladders 1014. If the rotation is complete, the method 1500 proceeds to block 1522, in which the patient orientation data is stored. The method 1500 then loops back to block 1502 to determine whether the patient should be rotated.

Referring now to FIGS. 16-19, in one embodiment, a patient bed 1602 includes one or more radar sensors 1604 connected to control circuitry 1606. In the illustrative example, radar support mount 1608 is used to support the one or more radar sensors 1604 and circuitry 1606. Mount 610 was discussed above in connection with FIG. 6 and the discussion is equally applicable to the use of mount 1608 with bed 1602 of FIGS. 16-19.

Figure 17:
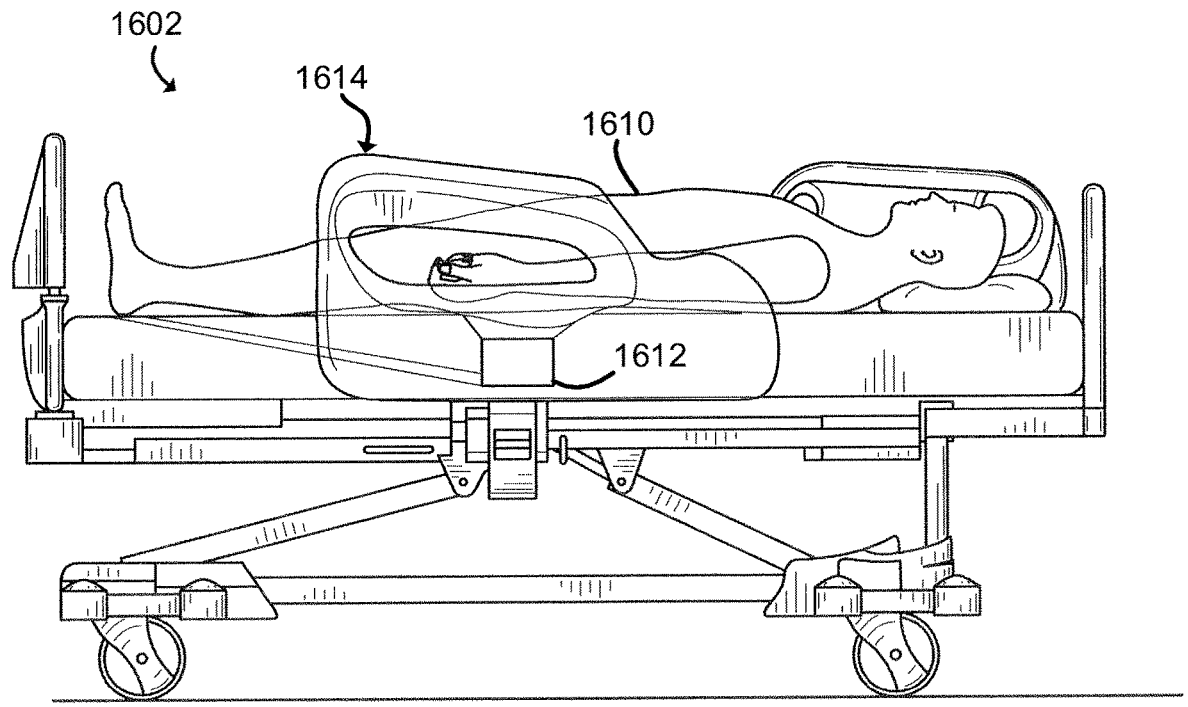
FIG. 17 is a side view of a system for monitoring a patient using one or more radar sensors.
Figure 18:
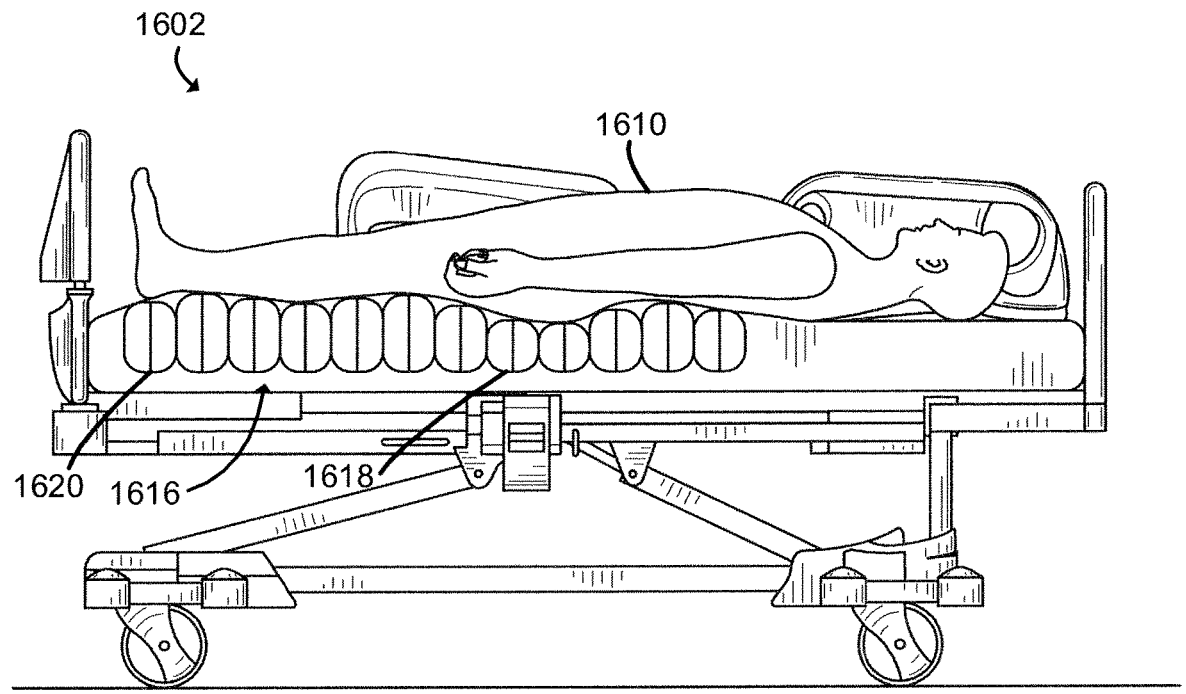
FIG. 18 is a side view of a system for monitoring a patient and controlling air bladders on a surface of a hospital bed using one or more radar sensors.

In use, the control circuitry 1606 may be configured to monitor a position of the patient using the radar sensor 1604 and, in particular, may monitor a depth of certain areas of the body of the patient 1610 in the mattress. In some embodiments, the patient bed 1602 may include a radar sensor 1612 in a side rail 1614, as shown in FIG. 17. The control circuitry 1606 may control air bladders 1616 to relieve pressure from certain parts of the body of the patient 1610, as shown in FIG. 18. For example, the control circuitry 1606 may deflate air bladders 1618 under the sacrum of the patient and deflate air bladders 1620 under the heel of the patient. It should be appreciated that the control circuitry 1606 can determine which air bladders are under the heel, sacrum, or other area of the patient with use of the radar sensors 1604, 1612.

In some embodiments, the patient bed includes one or more airflow controllers, such as airflow controller 1622 to control airflow to the sacrum of the patient 1610 and an airflow controller 1624 to control airflow to the heel of the patient, providing microclimate management of those areas. The airflow controllers 1622, 1624 may include fans and pumps to cause air to flow, humidity controls, and air temperature controls. The airflow controllers 1622, 1624 can control the air flow rate, humidity, and temperature of the targeted areas to reduce skin moisture and improve patient comfort. The location of the airflow being provided can be targeted to certain areas of the patient's body, which can be located using radar sensors 1604, 1612.

Figure 19:
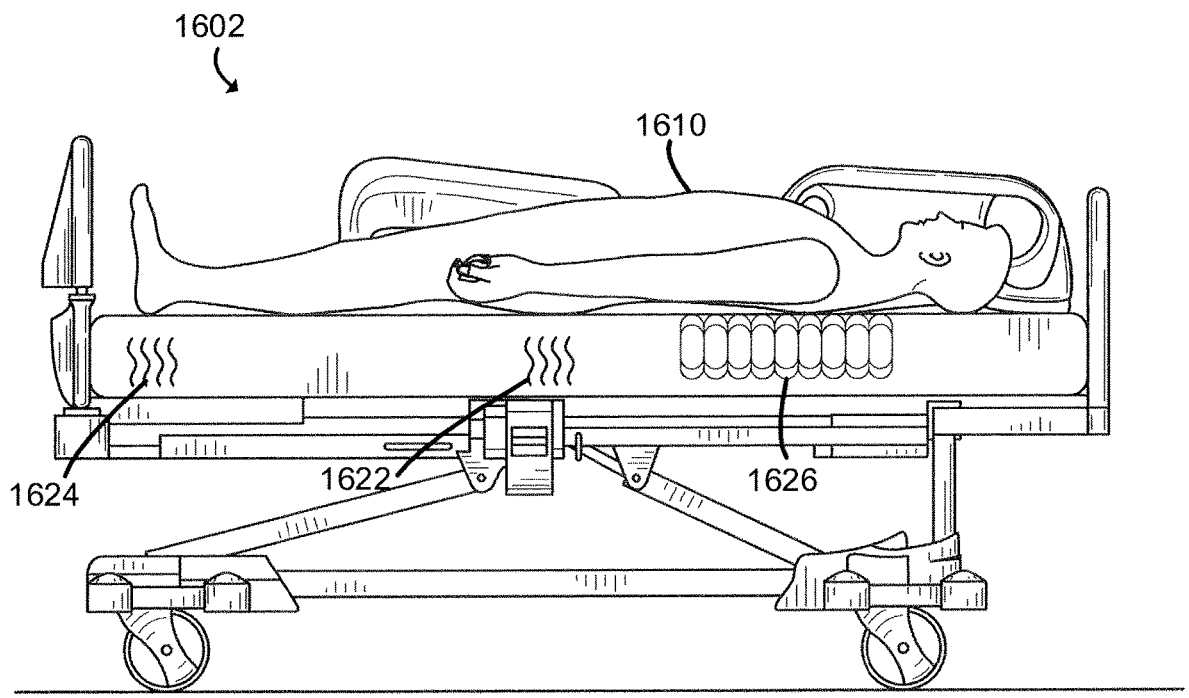
FIG. 19 is a side view of a system for microclimate management of a surface of a hospital bed and percussion and vibration (P & V) therapy using one or more radar sensors.

Additionally or alternatively, in some embodiments, the patient bed 1602 can include percussion and vibration (P & V) bladders 1626, as shown in FIG. 19. The P & V bladders 1626 can rapidly inflate and deflate, causing P & V on the area of the patient above the P & V bladders 1626. P & V treatment may be used to loosen and expel secretions that collect in the lungs of pulmonary patients. The radar sensor 1604 can be used to monitor the position of the patient, and the P & V bladders 1626 that are under the patient's chest can be selected for the P & V therapy. Additionally or alternatively, in some embodiments, the radar sensor 1604 may monitor the magnitude of the vibration of the patient's chest caused by the P & V bladders 1626. The magnitude of the vibrations of the P & V bladders 1626 can be tuned to cause an optimized vibration level of the patient's chest. In some embodiments, the patient bed 1602 may include P & V bladders 1626 and rotation bladders 1014 (see FIG. 13). The rotation bladders 1014 may be used to properly position the patient over the P & V bladders 1626 for P & V therapy.

Figure 20:
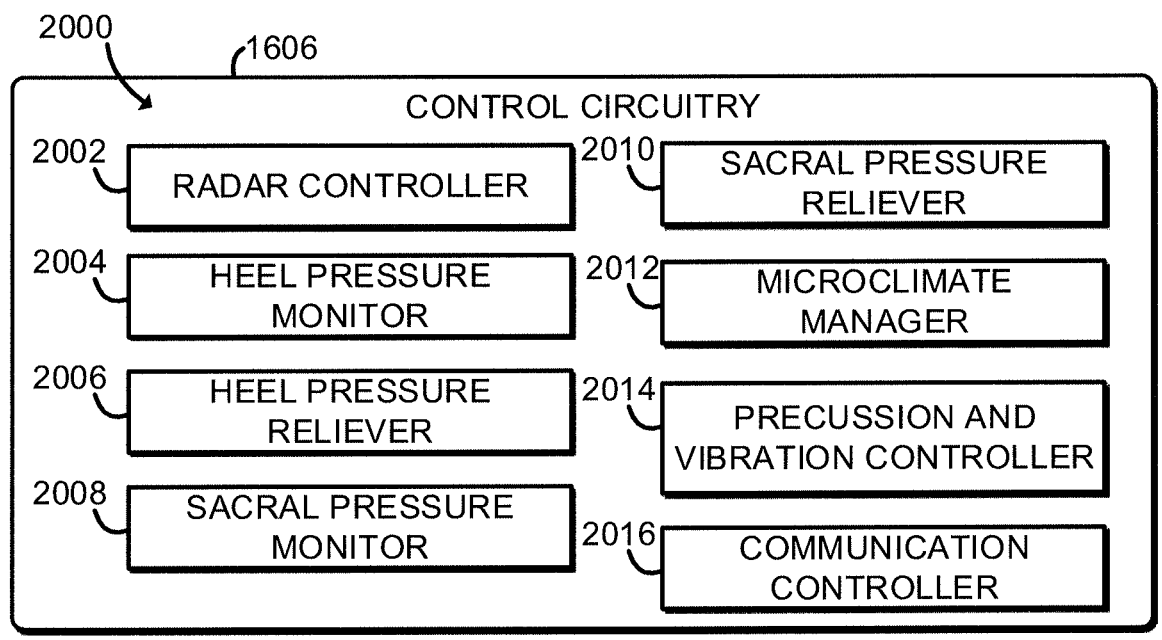
FIG. 20 is a block diagram of an environment that may be established by some or all of the circuitry of FIGS. 16-19.

Referring now to FIG. 20, in an illustrative embodiment, control circuitry 1606 establishes an environment 2000 during operation. The illustrative environment 2000 includes a radar controller 2002, a heel pressure monitor 2004, a heel pressure reliever 2006, a sacral pressure monitor 2008, a sacral pressure reliever 2010, a microclimate manager 2012, a P & V controller 2014, and a communication controller 2016. The various modules of the environment 2000 may be embodied as hardware, software, firmware, or a combination thereof. For example, the various modules, logic, and other components of the environment 2000 may form a portion of, or otherwise be established by, a processor, memory, or other hardware components of the control circuitry 2000. As such, in some embodiments, one or more of the modules of the environment 2000 may be embodied as circuitry or collection of electrical devices (e.g., radar controller circuitry 2002, heel pressure monitor circuitry 2004, heel pressure reliever circuitry 2006, etc.). It should be appreciated that, in such embodiments, one or more of the circuits (e.g., the radar controller circuitry 2002, the heel pressure monitor circuitry 2004, the heel pressure reliever circuitry 2006, etc.) may form a portion of one or more of the processor, the memory, the data storage, and/or other components of the control circuitry 1606. Additionally, in some embodiments, one or more of the illustrative modules may form a portion of another module and/or one or more of the illustrative modules may be independent of one another. Further, in some embodiments, one or more of the modules of the environment 2000 may be embodied as virtualized hardware components or emulated architecture, which may be established and maintained by the processor or other components of the control circuitry 1606.

The radar controller 2002, which may be embodied as hardware, firmware, software, virtualized hardware, emulated architecture, and/or a combination thereof as discussed above, is configured to interface with the radar sensor 1604, 1612. The radar controller 2002 may send commands to the radar sensor 1604, configure the radar sensor 1604, and receive data from the radar sensor 1604. In the illustrative embodiment, the radar controller 2002 receives indications of the signals received by the radar sensor 1604 such as the intensity, phase, electric field, etc., received at each receiver of the radar sensor 1604. In some embodiments, the radar sensor 1604 may perform some pre-processing before sending data to the radar controller 2002, such as by processing data received to provide an indication of the position or movement of the patient.

The heel pressure monitor 2004, which may be embodied as hardware, firmware, software, virtualized hardware, emulated architecture, and/or a combination thereof as discussed above, is configured to monitor pressure on the heels of the patient The heel pressure monitor 2004 may monitor the heel pressure based on the depth of the heels in the patient bed 1602 or based on any other suitable parameter.

The heel pressure reliever 2006, which may be embodied as hardware, firmware, software, virtualized hardware, emulated architecture, and/or a combination thereof as discussed above, is configured to relieve pressure from the heels of the patient. In some embodiments, the heel pressure reliever 2006 may relive pressure from the heels if the patient has not moved the patient's heels for at least a threshold amount of time, such as anywhere from 30 minutes to four hours. The heel pressure reliever 2006 may relieve pressure from the patient's heels by inflating an air bladder under the calves or ankles of the patient, by deflating the air bladders under the heel, or both. The heel pressure reliever 2006 may locate the appropriate air bladder to inflate or deflate using the radar sensors 1604, 1612. In some embodiments, the heel pressure reliever 2006 may alternate pressure on the heel, relieving pressure from other parts of the patient such as the calves.

The sacral pressure monitor 2008, which may be embodied as hardware, firmware, software, virtualized hardware, emulated architecture, and/or a combination thereof as discussed above, is configured to monitor pressure on the sacrum of the patient The sacral pressure monitor 2008 may monitor the sacral pressure based on the depth of the sacrum in the patient bed 1602 or based on any other suitable parameter. In some embodiments, the sacral pressure monitor 2008 may identify the ischial tuberosities of the patient and use the location of the ischial tuberosities of the patient to determine a sacral pressure of the patient.

The sacral pressure reliever 2010, which may be embodied as hardware, firmware, software, virtualized hardware, emulated architecture, and/or a combination thereof as discussed above, is configured to relieve pressure from the sacrum of the patient. In some embodiments, the sacral pressure reliever 2010 may relive pressure from the sacrum if the patient has not moved the patient's sacrum for at least a threshold amount of time, such as anywhere from 30 minutes to four hours. The sacral pressure reliever 2010 may relieve pressure from the patient's sacrum by inflating an air bladder under the back or thighs of the patient, by deflating the air bladders under the sacrum, or both. The sacral pressure reliever 2010 may locate the appropriate air bladder to inflate or deflate using the radar sensors 1604, 1612. In some embodiments, the sacral pressure reliever 2010 may alternate pressure on the sacrum, relieving pressure from other parts of the patient such as the thighs.

The microclimate manager 2012, which may be embodied as hardware, firmware, software, virtualized hardware, emulated architecture, and/or a combination thereof as discussed above, is configured to control airflow to one or more areas of the body of the patient, such as the heels, the sacrum, and/or the back. The microclimate manager 2012 interfaces with airflow controllers such as the airflow controllers 1622, 1624 to control fans and/or pumps, humidity controllers, and/or temperature controllers. In this way, the microclimate manager 2012 can controller the air flow rate, humidity, and temperature of the targeted areas to reduce skin moisture and improve patient comfort. The location of the airflow being provided can be targeted to certain areas of the patient's body, which can be located using radar sensors 1604, 1612.

The P & V controller 2014, which may be embodied as hardware, firmware, software, virtualized hardware, emulated architecture, and/or a combination thereof as discussed above, is configured to control the P & V bladders 1626. The P & V controller 2014 may determine when P & V therapy is necessary, such as by determining that the patient has not had P & V therapy for an amount of time that is past a threshold amount of time. The threshold may be any suitable value, such as any time between 30 minutes and 24 hours. In the illustrative embodiment, the threshold is 2 hours. In some embodiments, the time threshold may be determined based on a patient's symptoms. In some embodiments, P & V therapy may be determined to be necessary based on the symptoms of the patient. The P & V therapy may be initiated based on the patient's symptoms and/or the threshold time for performing P & V therapy may be set based on the symptoms of the patient.

To perform P & V therapy, the P & V controller 2014 monitors the position of the patient. If necessary, the P & V controller 2014 can move the patient to be located over the P & V bladders 1626. Additionally or alternatively, in some embodiments, the P & V controller 2014 may select the P &

V bladders 1626 that are under the current position of the patient. The P & V controller 2014 may then perform P & V therapy by inflating and deflating the selected P & V bladders 1626. In some embodiments, the P & V controller 2014 may monitor the amplitude of the vibrations of the patient, such as by using radar sensors. The amplitude of the inflation and deflation of the P & V bladders 1626 may be controlled based on the measured amplitude of the vibrations of the patient, forming a "closed loop" for the P & V therapy.

The communication controller 2016 is configured to communicate with other devices, such as the electronic medical records server 206 or the nurse call system 208. The communication controller 2016 may communicate with other devices directly or indirectly through, for example, Ethernet, Bluetooth®, Wi-Fi®, WiMAX, near field communication (NFC), etc. The communication controller 2016 may transmit data indicating heel pressure, data indicating, sacral pressure, microclimate data, and data related to P & V. The communication controller 2016 may send an alert or notification to, e.g., the electronic medical records server 206 or the nurse call system 208 that a patient needs to have pressure offloaded from the patient's heels, that the patient needs to have pressure offloaded from the patient's sacrum, that a microclimate of the patient needs adjusting, and/or that P & V therapy is required.

Figure 21:
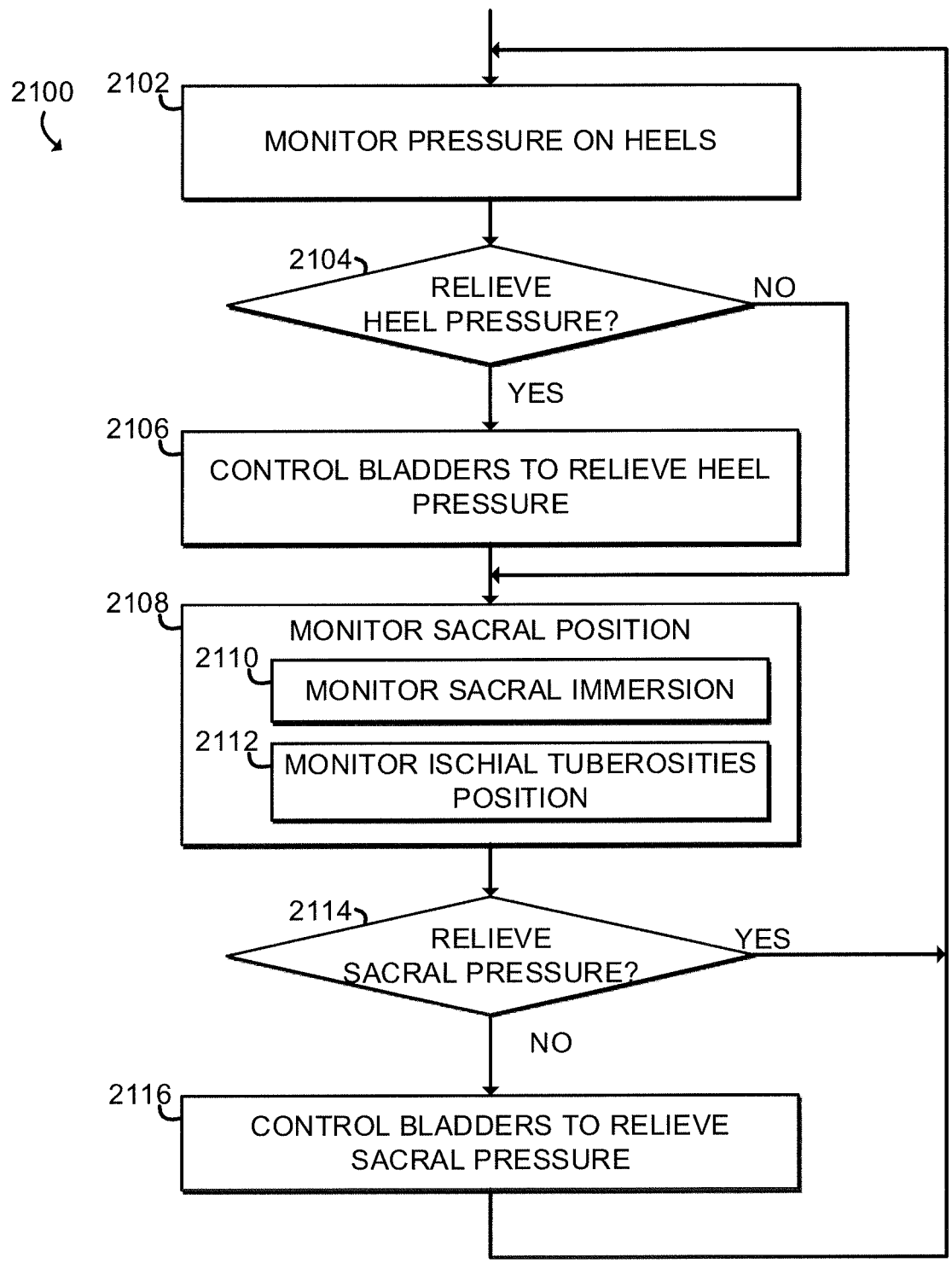
FIG. 21 is a flow chart of one embodiment of a method to relieve pressure on certain areas of a patient in one of the systems of FIGS. 16 and 17.

Referring now to FIG. 21, in use, a method 2100 for rotating a patient may be performed. In some embodiments, some or all of the method 2100 may be performed by the control circuitry 1606. Additionally or alternatively, in some embodiments, certain portions of the method 2100 may be performed a person, such as a caregiver of the patient. For example, the control circuitry 1606 may indicate that sacral pressure of the patient should be relieved, and a caregiver may relieve sacral pressure by causing air bladders to be inflated or rotating the patient. The method 2100 begins in block 2102, in which the control circuitry 1606 monitors pressure on the heels of the patient. The control circuitry 1606 may monitor the heel pressure based on the depth of the heels in the patient bed 1602 or based on any other suitable parameter.

In block 2104, if the control circuitry 1606 is to relieve heel pressure, the method 2100 proceeds to block 2106, in which the control circuitry 1606 signals one or more air bladders to inflate or deflate to relieve pressure from the patient's heels. In some embodiments, the control circuitry 1606 may determine that pressure should be relieved from the heels if the patient has not moved the patient's heels for at least a threshold amount of time, such as anywhere from 30 minutes to four hours. The control circuitry 1606 may relieve pressure from the patient's heels by inflating an air bladder under the calves or ankles of the patient, by deflating the air bladders under the heel, or both. The heel control circuitry 1606 may locate the appropriate air bladder to inflate or deflate using the radar sensors 1604, 1612.

Referring back to block 2104, if the control circuitry 1606 is not to relieve heel pressure, the method proceeds to block 2108, in which the control circuitry 1606 monitors the sacral pressure of the patient. The control circuitry 1606 may monitor the sacral immersion in the patient bed 1602 in block 2110. The control circuitry 1606 monitor the ischial tuberosities of the patient and use the location of the ischial tuberosities of the patient to determine a sacral pressure of the patient in block 2112.

In block 2114, if the control circuitry 1606 is not to relieve sacral pressure, the method 2100 loops back to block 2102 to monitor pressure on the patient's heels. If the control circuitry 1606 is to relieve sacral pressure, the method 2100 proceeds to block 2116, in which control circuitry 1606 signals one or more air bladders to inflate or deflate to relieve pressure from the patient's sacrum. In some embodiments, the control circuitry 1606 may determine that pressure should be relieved from the sacrum if the patient has not moved the patient's sacrum for at least a threshold amount of time, such as anywhere from 30 minutes to four hours. The control circuitry 1606 may relieve pressure from the patient's sacrum by inflating an air bladder under the back or thighs of the patient, by deflating the air bladders under the sacrum, or both. The control circuitry 1606 may locate the appropriate air bladder to inflate or deflate using the radar sensors 1604, 1612. The method 2100 then loops back to block 2102 to monitor pressure on the patient's heels.

Figure 22:
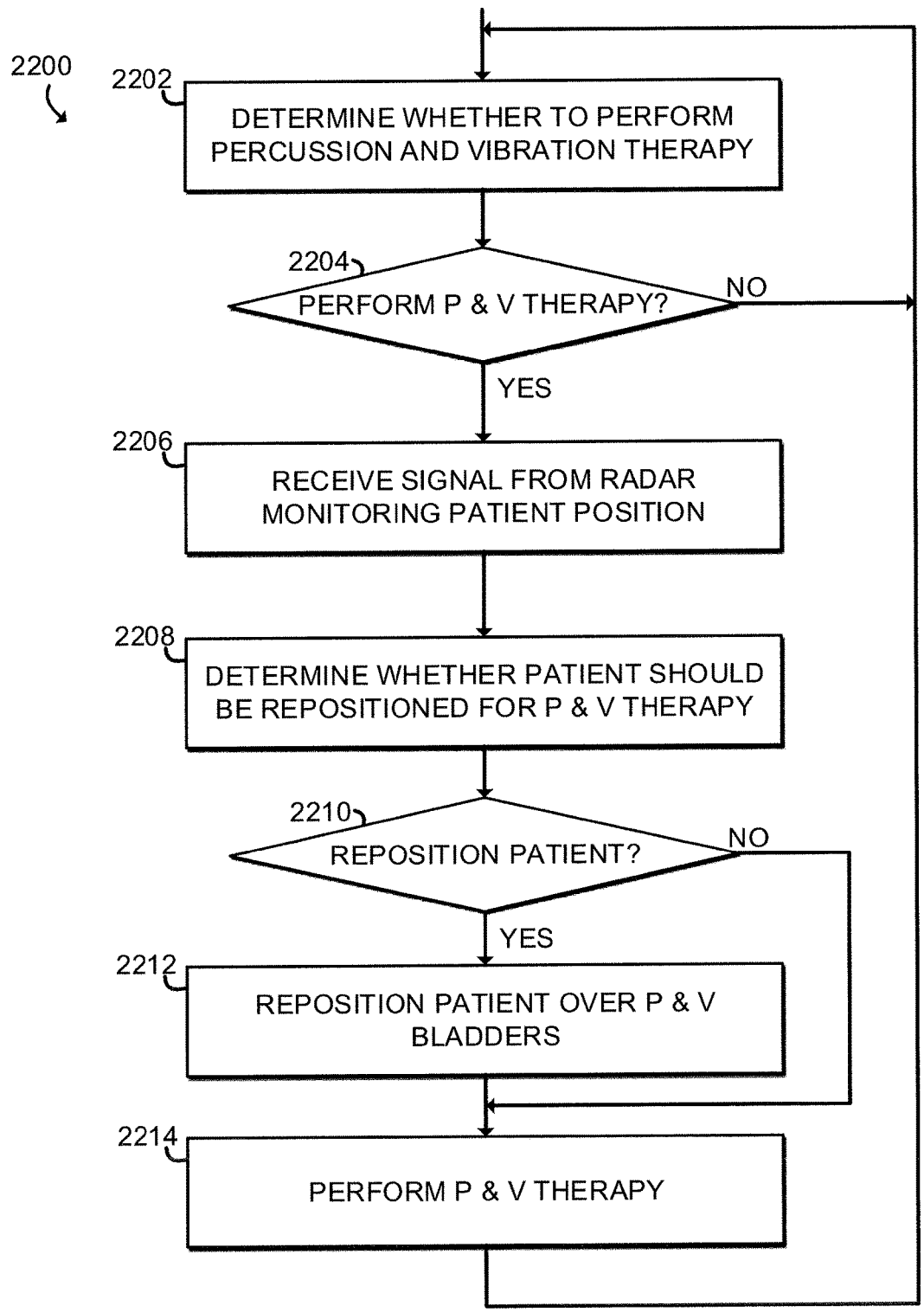
FIG. 22 is a flow chart of one embodiment of a method to perform P & V therapy on a patient in the system of FIG. 19.

Referring now to FIG. 22, in use, a method 2200 for performing P & V therapy on a patient may be performed. In some embodiments, some or all of the method 2200 may be performed by the control circuitry 1606. Additionally or alternatively, in some embodiments, certain portions of the method 2200 may be performed a person, such as a caregiver of the patient. For example, a caregiver may determine that P & V therapy should be performed, and the caregiver may then instruct the control circuitry 1606 to perform P & V therapy. The method 2200 begins in block 2202, in which the control circuitry 1606 determines whether to perform P & V therapy. The control circuitry 1606 may determine whether P & V therapy is to be performed by determining that the patient has not had P & V therapy for an amount of time that is past a threshold amount of time. The threshold may be any suitable value, such as any time between 30 minutes and 24 hours. In the illustrative embodiment, the threshold is 2 hours. In some embodiments, the threshold may be determined based on a patient's symptoms. In some embodiments, P & V therapy may be determined to be necessary based on the symptoms of the patient. The P & V therapy may be initiated based on the patient's symptoms and/or the threshold time for performing P & V therapy may be set based on the symptoms of the patient.

In block 2204, if P & V therapy is not to be performed, the method 2200 loops back to block 2202 to determine whether P & V therapy should be performed. If P & V therapy is to be performed, the method 2200 continues to block 2206, in which the control circuitry 1606 receives a signal from a radar sensor monitoring a position of the patient. In block 2208, the control circuitry 1606 determines whether the patient should be repositioned for P & V therapy. For example, the control circuitry 1606 may determine that the patient should be positioned over the P & V bladders 1626 prior to beginning the P & V therapy.

In block 2210, if the patient is to be repositioned, the method proceeds to block 2212 to reposition the patient over the P & V bladders 1626. In the illustrative embodiment, other bladders such as the rotation bladders 1014 may be used to reposition the patient.

After the patient is repositioned, or if no repositioning is required, the method 2200 proceeds to block 2214, where the control circuitry 1606 performs P & V therapy. The control circuitry 1606 performs P & V therapy by rapidly inflating and deflating the P & V bladders 1626. In some embodiments, the control circuitry 1606 may monitor the amplitude of the vibrations of the patient, such as by using radar sensors. The amplitude of the inflation and deflation of the P & V bladders 1626 may be controlled based on the measured amplitude of the vibrations of the patient, forming a "closed loop" for the P & V therapy. After the P & V therapy is performed, the method loops back to block 2202 to determine whether further P & V therapy is needed.

Figure 23:
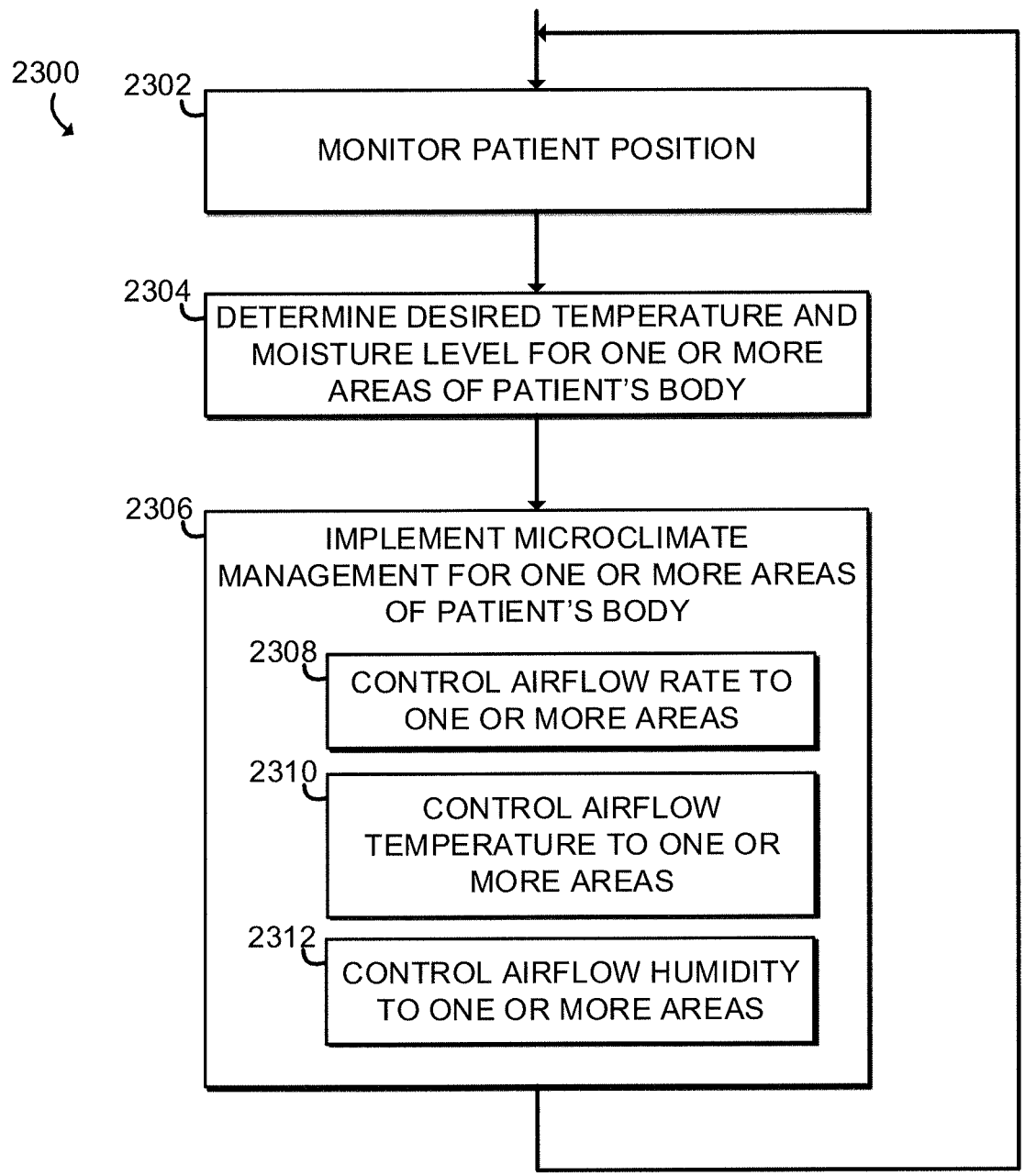
FIG. 23 is a flow chart of one embodiment of a method to perform microclimate management in the system of FIG. 19.

Referring now to FIG. 23, in use, a method 2300 for microclimate management may be performed. In some embodiments, some or all of the method 2300 may be performed by the control circuitry 1606. Additionally or alternatively, in some embodiments, certain portions of the method 2300 may be performed a person, such as a caregiver of the patient. For example, a caregiver may determine that a moisture level on the sacrum of the patient should be reduced, and the caregiver may then instruct the control circuitry 1606 to control airflow to reduce moisture at the sacrum of the patient. The method 2300 begins in block 2302, in which the control circuitry 1606 monitors a position of the patient, such as the position of the heels, sacrum, and back of the patient. In some embodiments, the control circuitry 1606 may also monitor a temperature, humidity, and/or moisture level of certain areas of the patient, such as the heels, sacrum, and back of the patient.

In block 2304, the control circuitry 1606 determines a desired temperature and moisture level for one or more areas of the patient's body. The control circuitry 1606 may make the determination based on any suitable factor, such as duration of time an area of the patient's body has been in contact with the surface of the patient bed 1602, a temperature of the room, a previous measurement or observation of a moisture level of a patient, an indicated desire of a patient, an input from a caregiver, etc.

In block 2306, the control circuitry 1606 implements microclimate management for one or more areas of the patient's body. In block 2308, the control circuitry 1606 controls an airflow rate to one or more areas of the patient's body. In block 2310, the control circuitry 1606 controls a temperature of the airflow to one or more areas of the patient's body. In block 2312, the control circuitry 1606 controls a humidity level of airflow to one or more areas of the patient's body. The method 2300 then loops back to block 2302.

Referring now to FIGS. 24-29, in one embodiment, a patient bed 2402 includes one or more radar sensors 2404 connected to control circuitry 2406. In the illustrative example, radar support mount 2408 is used to support the one or more radar sensors 2404 and control circuitry 2406. Mount 610 was discussed above in connection with FIG. 6 and the discussion is equally applicable to the use of mount 2408 with bed 2402 of FIGS. 24-28.

Figure 24:
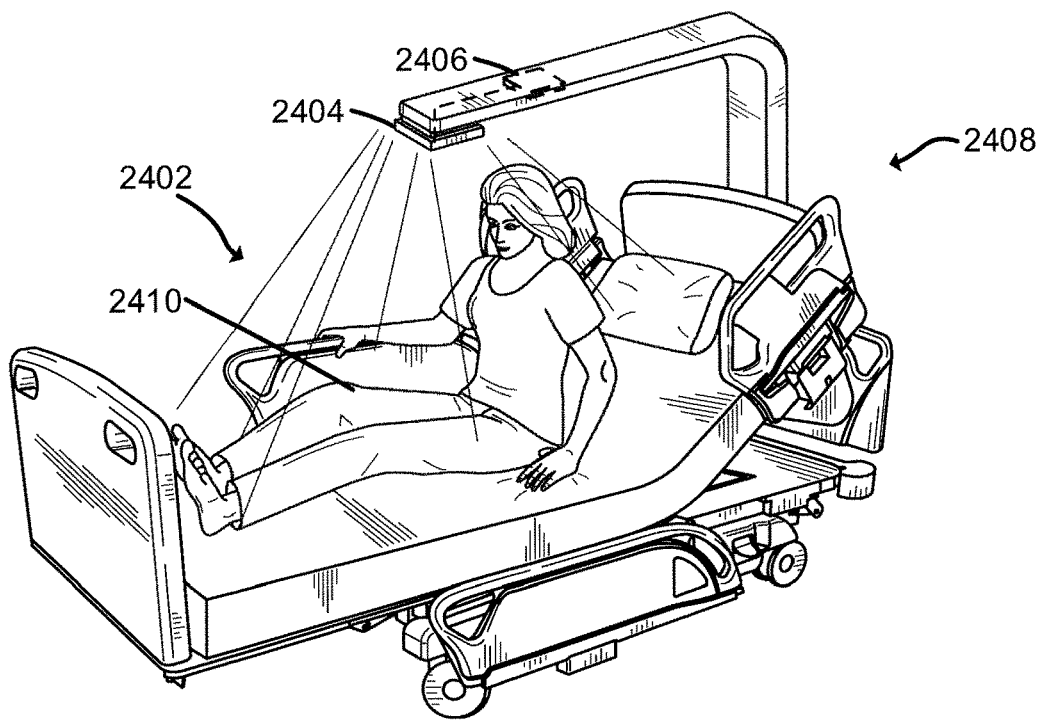
FIG. 24 is a perspective view of a system for monitoring a patient in a hospital bed using one or more radar sensors.
Figure 25:
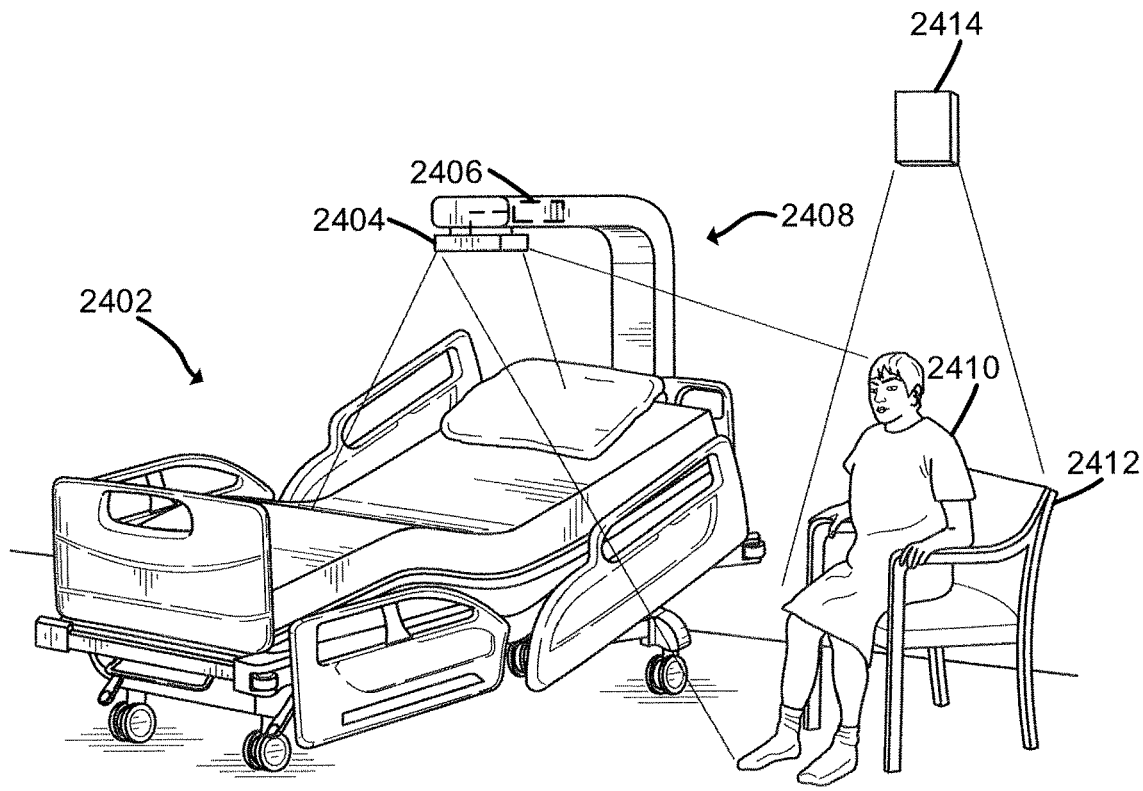
FIG. 25 is a perspective view of a system for monitoring a patient sitting in a room using one or more radar sensors.

In use, the control circuitry 2406 may be configured to monitor a position of the patient using the radar sensor 2404 and, in particular, may monitor a location of the patient in the room that the patient bed 2402 is located in. For example, the control circuitry 2406 may monitor a position of the patient in the patient bed 2402 (such as lying down or sitting up, as shown in FIG. 24), or the control circuitry 2406 may monitor a position of the patient near the patient bed 2402 (such as sitting in a chair 2412 as shown in FIG. 25). In some embodiments, one or more radar sensors may be positioned near the patient bed 2402, such as a radar sensor 2414 on a wall nearby the patient bed 2402.

Figure 26:
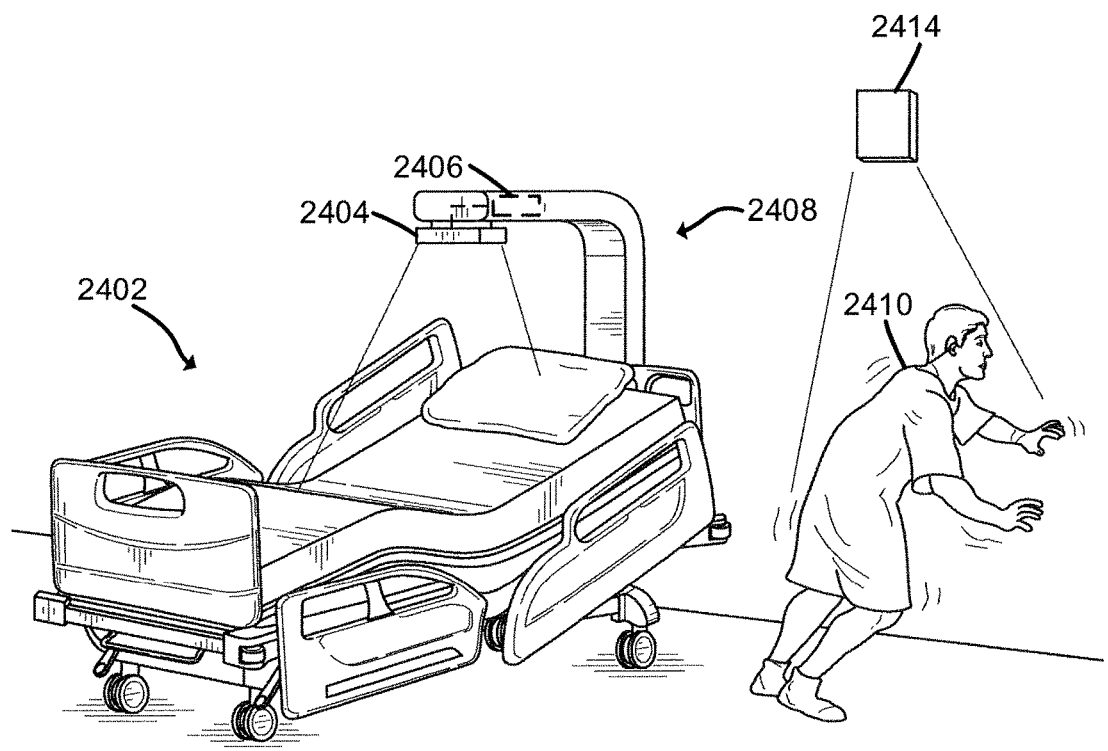
FIG. 26 is a perspective view of a system for monitoring a patient walking in a room using one or more radar sensors.
Figure 27:
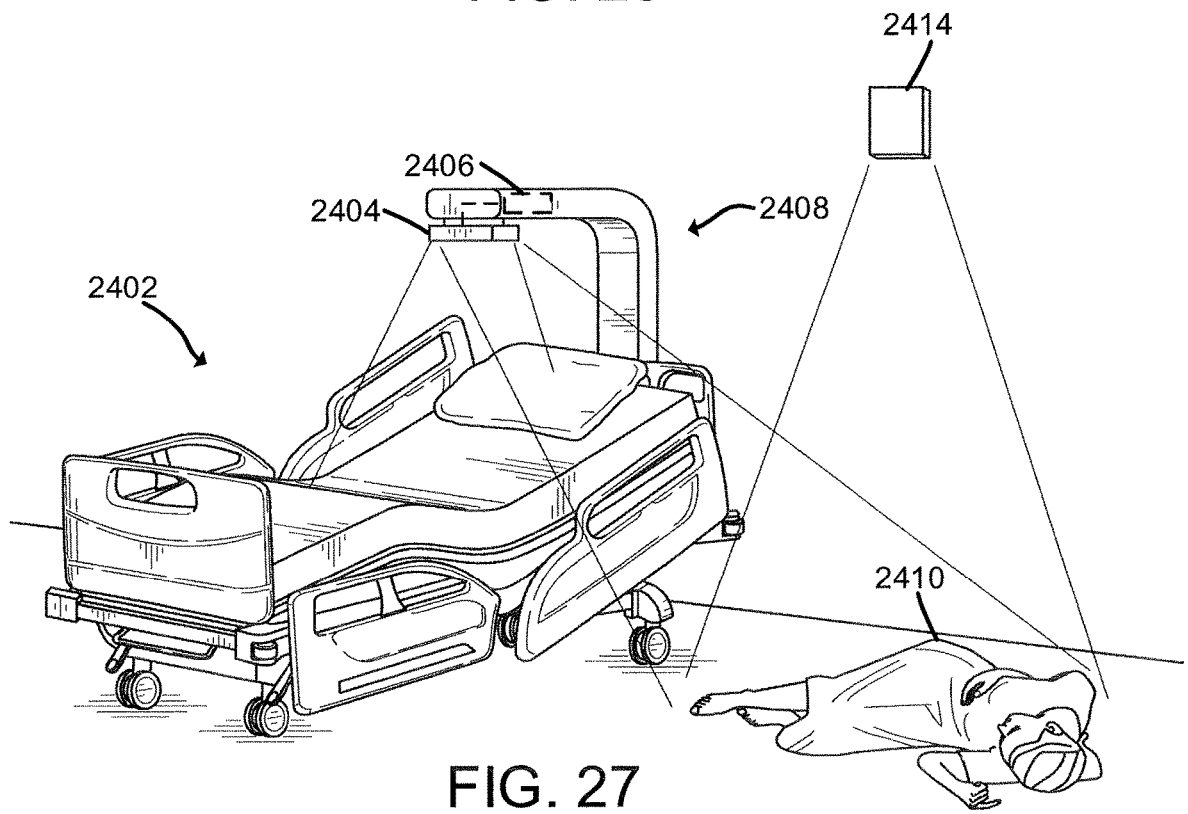
FIG. 27 is a perspective view of a system for monitoring a patient on the floor of a room using one or more radar sensors.
Figure 28:
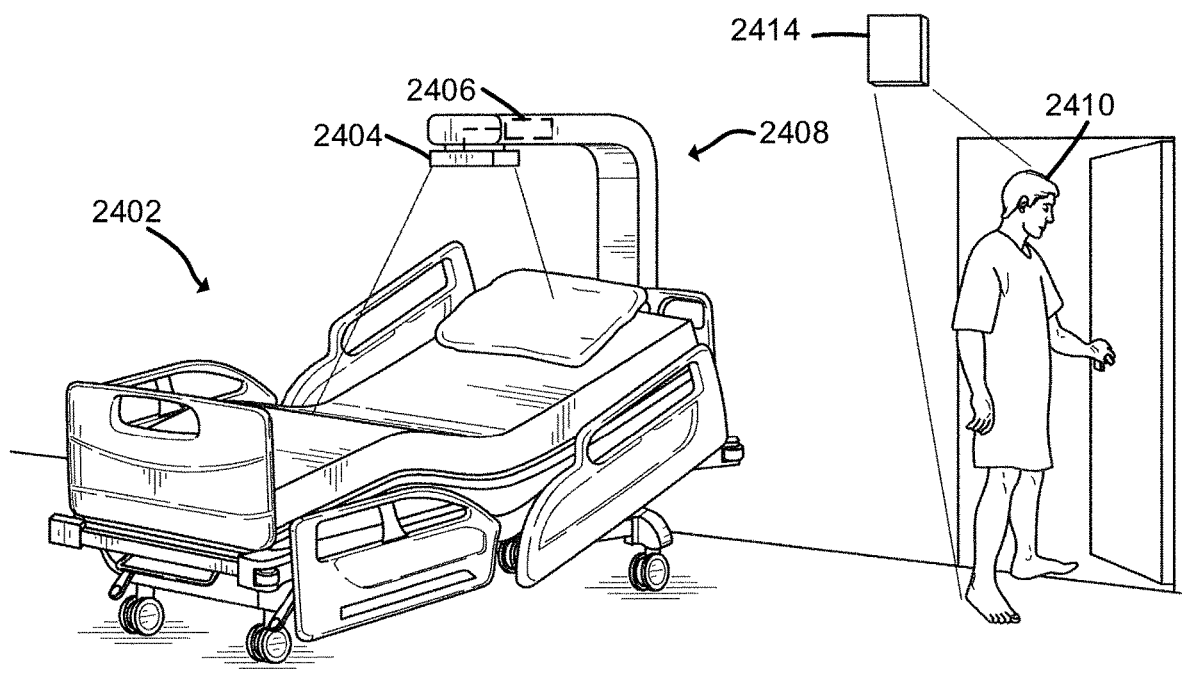
FIG. 28 is a perspective view of a system for monitoring a patient leaving a room one or more radar sensors.

The control circuitry 2406 may monitor the patient 2410 in several potentially dangerous activities or situations. For example, as shown in FIG. 26, the control circuitry 2406 may determine that a patient 2410 walking around the room has an unsteady gait and requires assistance. As shown in FIG. 27, the control circuitry 2406 may detect a patient 2410 that has fallen on the ground and alert caregivers. As shown in FIG. 28, the control circuitry 2406 may detect a patient that is leaving the room and alert caregivers accordingly.

Figure 29:
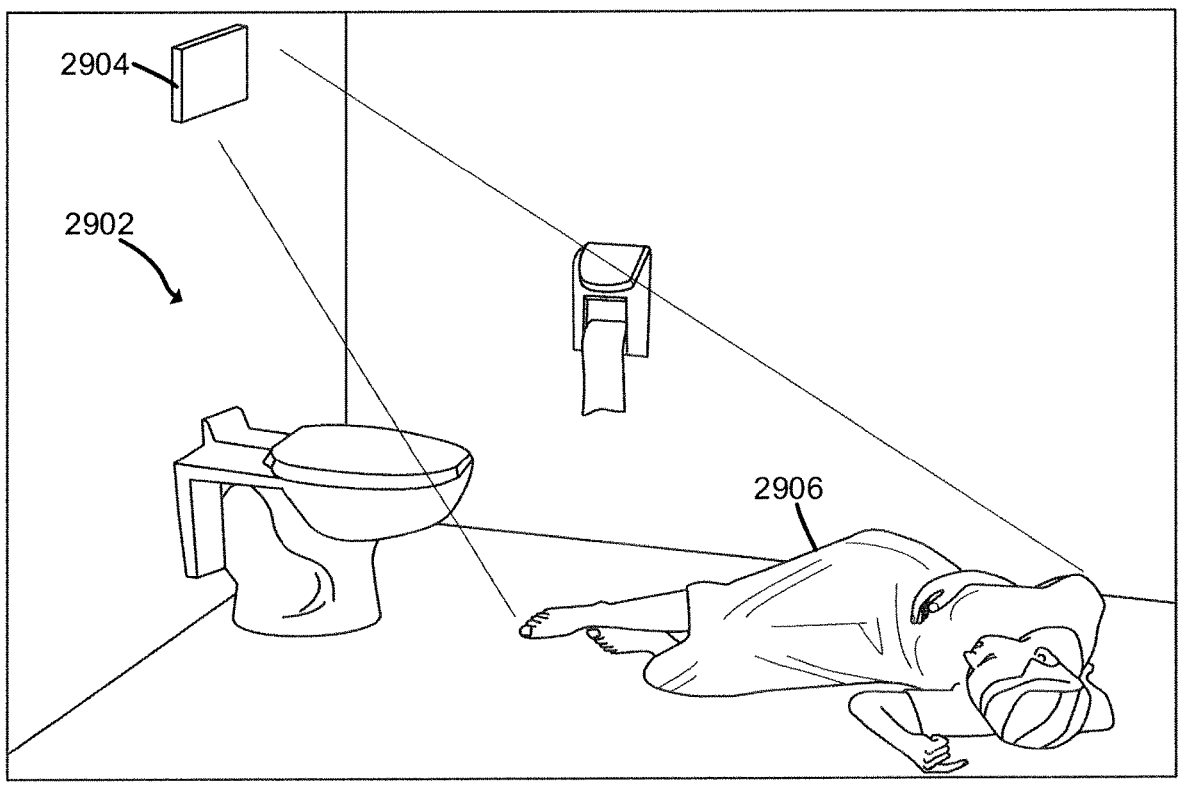
FIG. 29 is a perspective view of a system for monitoring a patient on the floor of a bathroom using one or more radar sensors.

Referring now to FIG. 29, in some embodiments, a bathroom 2902 may include one or more radar sensors 2904 connected to control circuitry 2406. The radar sensors 2904 may be used to monitor a patient 2906 for a fall in the bathroom 2902. In some embodiments, radar sensors 2404 in the patient bed 2402 or other radar sensors 2412 outside of the bathroom 2902 may be used to monitor the patient in the bathroom 2902, as certain frequencies used by the radar sensors 2404, 2412 may pass through the walls of the bathroom 2902.

Figure 30:
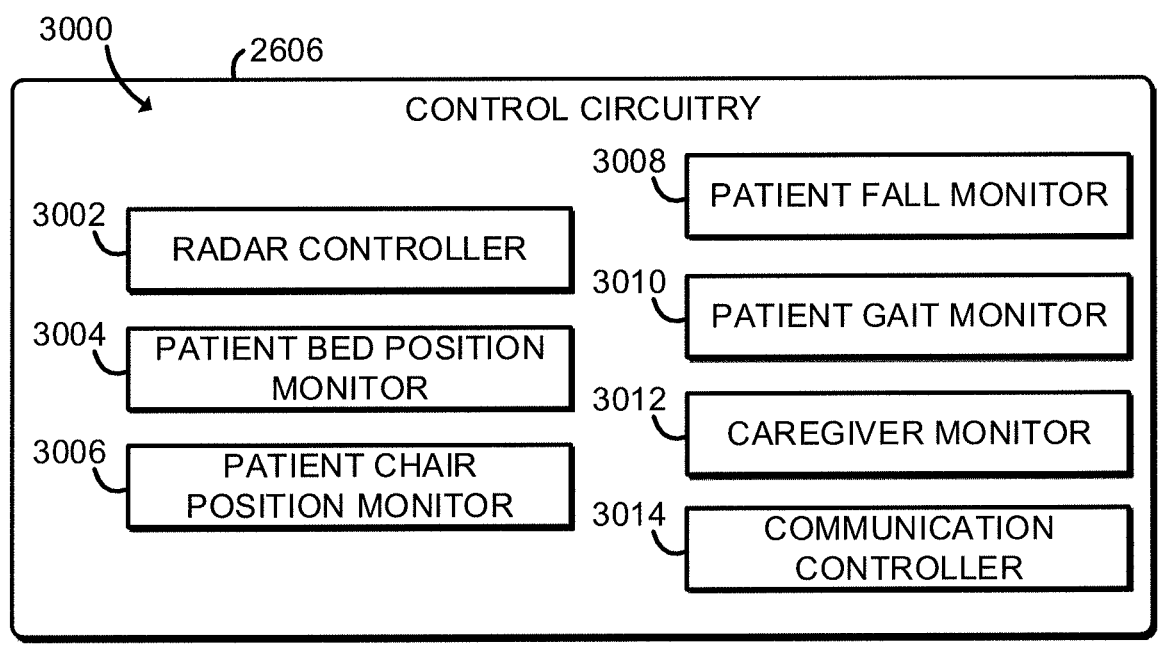
FIG. 30 is a block diagram of an environment that may be established by some or all of the circuitry of FIGS. 24-29.

Referring now to FIG. 30, in an illustrative embodiment, control circuitry 2406 establishes an environment 3000 during operation. The illustrative environment 3000 includes a radar controller 3002, a patient bed position monitor 3004, a patient char position monitor 3006, a patient fall monitor 3008, a patient gait monitor 3010, and a caregiver monitor 3012. The various modules of the environment 3000 may be embodied as hardware, software, firmware, or a combination thereof. For example, the various modules, logic, and other components of the environment 3000 may form a portion of, or otherwise be established by, a processor, memory, or other hardware components of the control circuitry 2406. As such, in some embodiments, one or more of the modules of the environment 3000 may be embodied as circuitry or collection of electrical devices (e.g., radar controller circuitry 3002, patient bed position monitor circuitry 3004, patient chair position monitor circuitry 3006, etc.). It should be appreciated that, in such embodiments, one or more of the circuits (e.g., the radar controller circuitry 3002, the patient bed position monitor circuitry 3004, the patient chair position monitor circuitry 3006, etc.) may form a portion of one or more of the processor, the memory, the data storage, and/or other components of the control circuitry 2406. Additionally, in some embodiments, one or more of the illustrative modules may form a portion of another module and/or one or more of the illustrative modules may be independent of one another. Further, in some embodiments, one or more of the modules of the environment 3000 may be embodied as virtualized hardware components or emulated architecture, which may be established and maintained by the processor or other components of the control circuitry 2406.

The radar controller 3002, which may be embodied as hardware, firmware, software, virtualized hardware, emulated architecture, and/or a combination thereof as discussed above, is configured to interface with the radar sensor 2404, 2414. The radar controller 2002 may send commands to the radar sensor 2404, 2414, configure the radar sensor 2404, 2414, and receive data from the radar sensor 2404, 2414. In the illustrative embodiment, the radar controller 3002 receives indications of the signals received by the radar sensor 2404, 2414 such as the intensity, phase, electric field, etc., received at each receiver of the radar sensor 2404, 2412. In some embodiments, the radar sensor 2404, 2414 may perform some pre-processing before sending data to the radar controller 3002, such as by processing data received to provide an indication of the position or movement of the patient.

The patient bed position monitor 3004, which may be embodied as hardware, firmware, software, virtualized hardware, emulated architecture, and/or a combination thereof as discussed above, is configured to monitor a position of the patient in the bed. The patient bed position monitor 3004 may determine whether a patient is lying down, sitting up, or in some other position.

The patient char position monitor 3006, which may be embodied as hardware, firmware, software, virtualized hardware, emulated architecture, and/or a combination thereof as discussed above, is configured to monitor a position or presence of a patient in a chair 2412. The patient char position monitor 3006 may monitor a patient in the process of sitting down, while the patient is sitting down, and while the patient is in the process of standing up.

The patient fall monitor 3008, which may be embodied as hardware, firmware, software, virtualized hardware, emulated architecture, and/or a combination thereof as discussed above, is configured to monitor the patient for a fall. The patient fall monitor 3008 may monitor a patient in the same room as the patient bed 2402 for a fall and/or may monitor a patient in a different room as the patient bed 2402 for a fall, such as a bathroom.

The patient gait monitor 3010, which may be embodied as hardware, firmware, software, virtualized hardware, emulated architecture, and/or a combination thereof as discussed above, is configured to monitor a patient's gait. If the patient gait monitor 3010 determines that a patient's gait is unsteady, the patient gait monitor 3010 may send an alert to a caregiver that the patient may require some support.

The caregiver monitor 3012, which may be embodied as hardware, firmware, software, virtualized hardware, emulated architecture, and/or a combination thereof as discussed above, is configured to monitor caregivers or other people in the same room as the patient bed 2402. The caregiver monitor 3012 may monitor contact between the patient and caregiver, monitor whether the caregiver or other person washes their hands, how long the caregiver or other person is in the room, how long the caregiver reviews medical charts, etc.

The communication controller 3014 is configured to communicate with other devices, such as the electronic medical records server 206 or the nurse call system 208. The communication controller 3014 may communicate with other devices directly or indirectly through, for example, Ethernet, Bluetooth®, Wi-Fi®, WiMAX, near field communication (NFC), etc. The communication controller 3014 may transmit data indicating the patient's position (such as in bed, in chair, walking, etc.). The communication controller 3014 may send an alert or notification to, e.g., the electronic medical records server 206 or the nurse call system 208 that a patient has fallen, has an unsteady gait, or is leaving the room.

Figure 31:
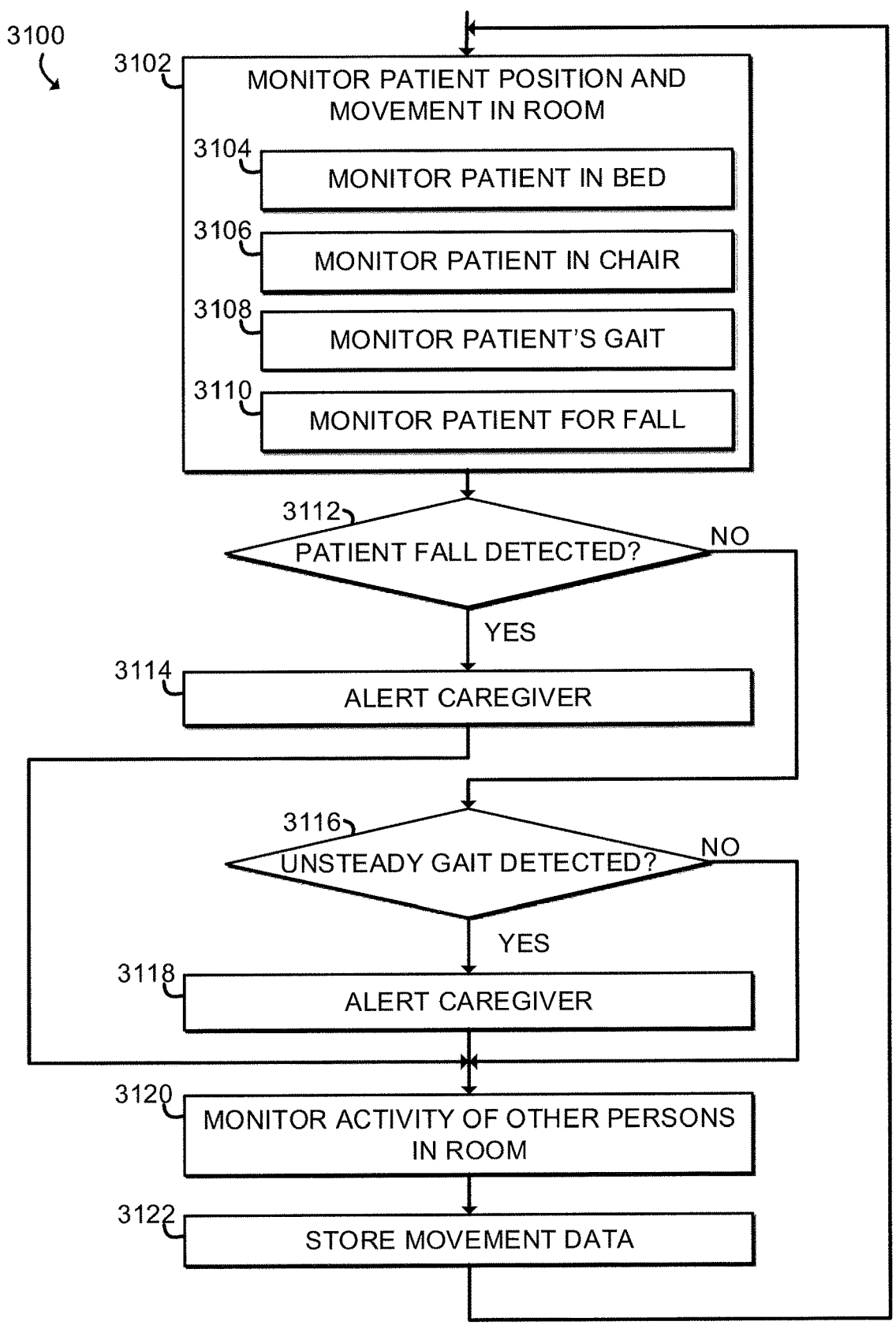
FIG. 31 is a flow chart of one embodiment of a method to monitor patient movement in the system of FIGS. 24-29.
Figure 32:
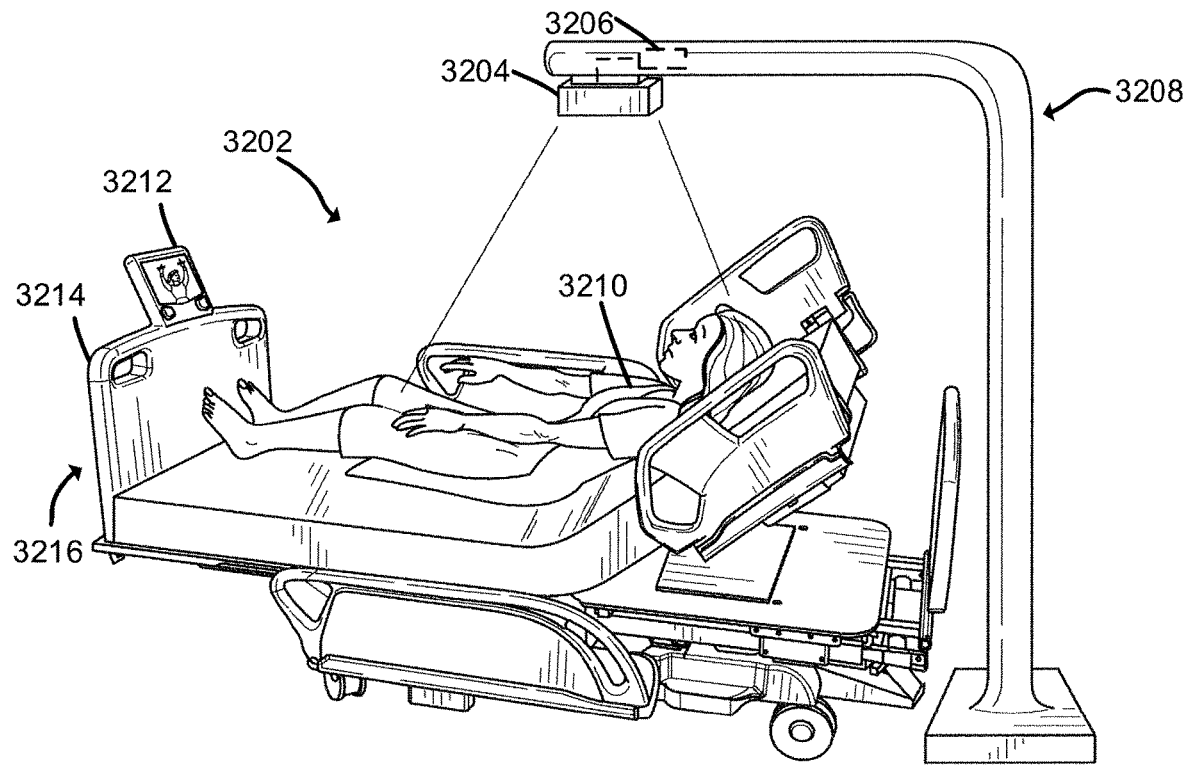
FIG. 32 is a perspective view of a system for monitoring a patient in a bed performing physical therapy using one or more radar sensors.
Figure 33:
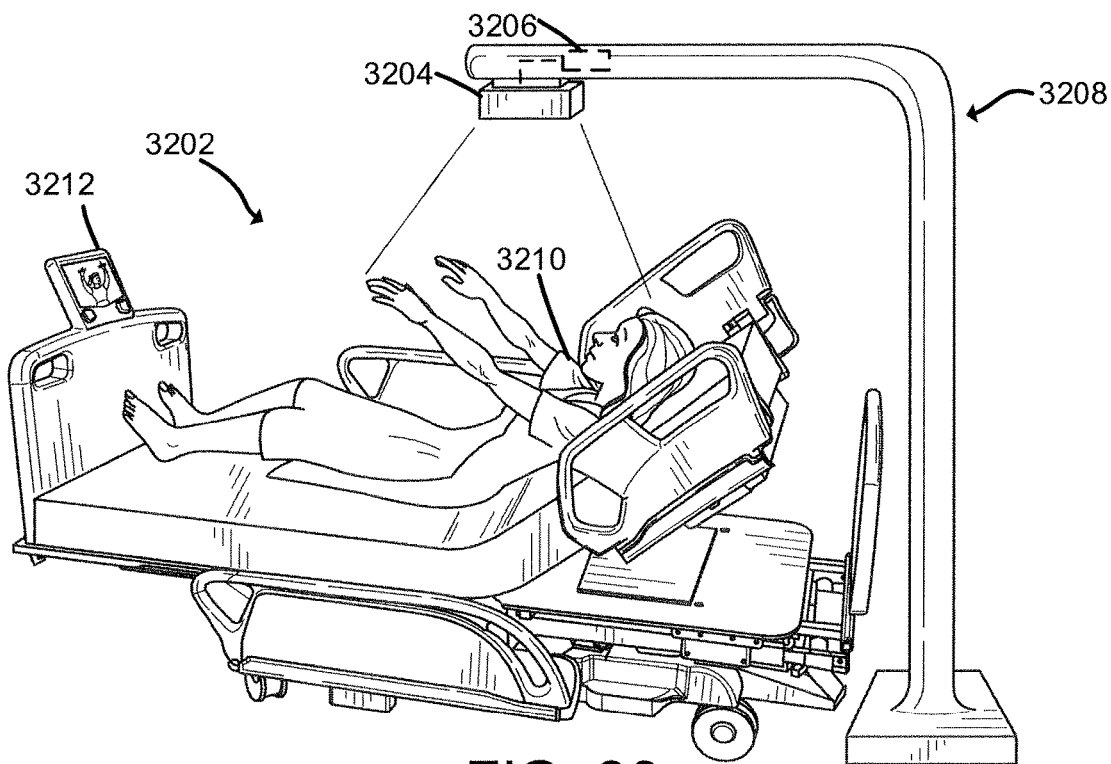
FIG. 33 is a perspective view of a system for monitoring a patient in a bed performing physical therapy using one or more radar sensors.

Referring now to FIG. 31, in use, a method 3100 for monitoring a patient in a room may be performed. In some embodiments, some or all of the method 3100 may be performed by the control circuitry 2406. Additionally or alternatively, in some embodiments, certain portions of the method 3100 may be performed a person, such as a caregiver of the patient. The method 3100 begins in block 312, in which the control circuitry 2406 monitors a position and movement of the patient. The control circuitry 2406 may monitor a position of a patient in the patient bed 2402 in block 3104, such as by monitoring whether the patient is lying down, sitting up, etc. The control circuitry 2406 may monitor a position of a patient in a chair in block 3106. The control circuitry 2406 may monitor a patient in the process of sitting down, while the patient is sitting down, and while the patient is in the process of standing up. In block 3108, the control circuitry 2406 may monitor a patient's gait. In block 3110, the control circuitry 2406 monitors the patient for a fall. The control circuitry 2406 may monitor a patient in the same room as the patient bed 2402 for a fall and/or may monitor a patient in a different room as the patient bed 2402 for a fall, such as a bathroom.

In block 3112, if a patient fall is not detected, the method 3100 jumps forward to block 3116 to determine if an unsteady gait is detected. If a patient fall is detected, the method proceeds to block 3114, in which the control circuitry 2406 alerts a caregiver, such as by sending a message to the nurse call system 208. The method 3100 then jumps to block 3120 to monitor the activity of other persons in the room.

Referring back to block 3112, if a patient fall is not detected, the method 3100 jumps forward to block 3116. In block 3116, if an unsteady gait is not detected, the method 3100 jumps forward to block 3120 to monitor activity of other persons in the room. If an unsteady gait is detected, the method 3100 proceeds to block 3118, in which the control circuitry 2406 alerts a caregiver that a patient may require assistance, such as by sending a message to the nurse call system 208.

The method 3100 then proceeds to block 3120 to monitor the activity of other persons in the room. The control circuitry 2406 may monitor caregivers or other people in the same room as the patient bed 2402. The control circuitry 2406 may monitor contact between the patient and caregiver, monitor whether the caregiver or other person washes their hands, how long the caregiver or other person is in the room, how long the caregiver reviews medical charts, etc.

In block 3122, the control circuitry 2406 stores data related to patient movement as well as data related to movement of other persons such as caregivers. The method 3100 then loops back to block 3102 to continue monitoring the position and movement of the patient in the room.

Referring now to FIGS. 32-35, in one embodiment, a patient bed 3202 includes one or more radar sensors 3204 connected to control circuitry 3206. In the illustrative example, radar support mount 3208 is used to support the one or more radar sensors 3204 and control circuitry 3206. Mount 610 was discussed above in connection with FIG. 6 and the discussion is equally applicable to the use of mount 3208 with bed 3202 of FIGS. 32 & 33. The patient bed 3202 also has a display 3212 positioned on footboard 3214 at the foot end 3216 of the bed 3202, visible to the patient 3210.

In use, the control circuitry 3206 executes a program for helping the patient perform physical therapy, such as by presenting on the display 3206 physical therapy exercises for the patient to perform. The physical therapy may be any suitable exercises for a patient to perform in bed, such as exercises for stretching arms, lifting legs, etc. For example, in one embodiment, the display 3212 may display an instruction for the patient to lift her arms from a first position shown in FIG. 32 to a second position shown in FIG. 33. The movement of the patient can be monitored using the radar sensor 3204, allowing for feedback that can be provided to the control circuitry 3206. In some embodiments, the physical therapy exercises can be "gamified," such as by allowing a user to earn points or achievements based on time spent performing exercises or results obtained. The physical therapy exercises may be done while the patient is supine, siting up, or in any other suitable position.

Figure 34:
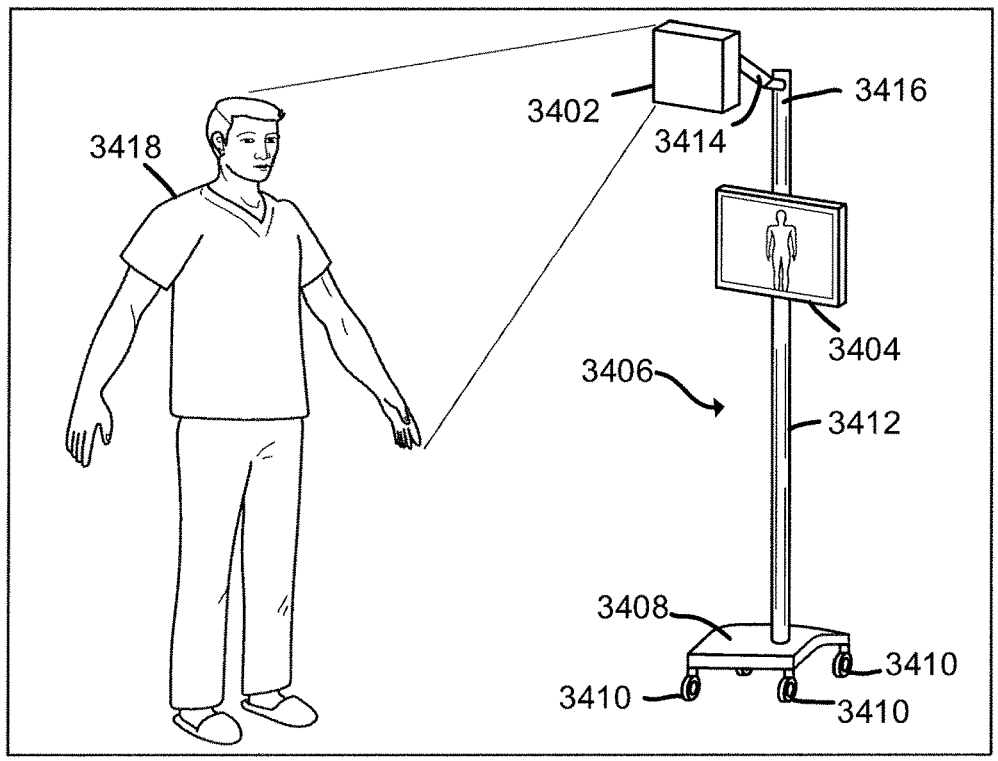
FIG. 34 is a perspective view of a system for monitoring a patient performing physical therapy using one or more radar sensors.

It should be appreciated that use of radar sensors as feedback in performing physical therapy exercises is not limited to patients that are in a patient bed. For example, as shown in FIG. 34, in one embodiment, a radar sensor 3402 and a display 3404 are mounted on a mobile physical therapy device 3406, allowing for a patient to perform physical therapy exercises while standing up, sitting, etc., in any suitable location. Mobile physical therapy device 3406 includes a wheeled base 3408 having casters 3410 coupled thereto. Mobile physical therapy device 3406 further includes a generally vertically oriented pole or mast 3412 extending upwardly from base 3408. A pivotable arm 3414 extends from an upper region 3416 of pole 3412 and radar sensor 3402 is mounted to a distal end of arm 3414 in spaced relation with pole 3412. Arm 3414 is pivotable upwardly and downwardly relative to pole 3412 to adjust a height at which radar sensor 3402 is supported above the floor.

In some embodiments, arm 3414 is movable vertically along pole 3412 to provide further adjustment of the vertical position of radar sensor 3402 relative to the floor. For example, a lockable and releasable collar may be coupled to pole 3412 and arm 3414 may extend from the collar. When released, the collar is movable upwardly and downwardly along pole 3412 and then lockable in the desired position. A clamp, lock, thumb screw, or similar releasable locking device is provided in some embodiments for locking the collar relative to pole 3412.

Figure 35:
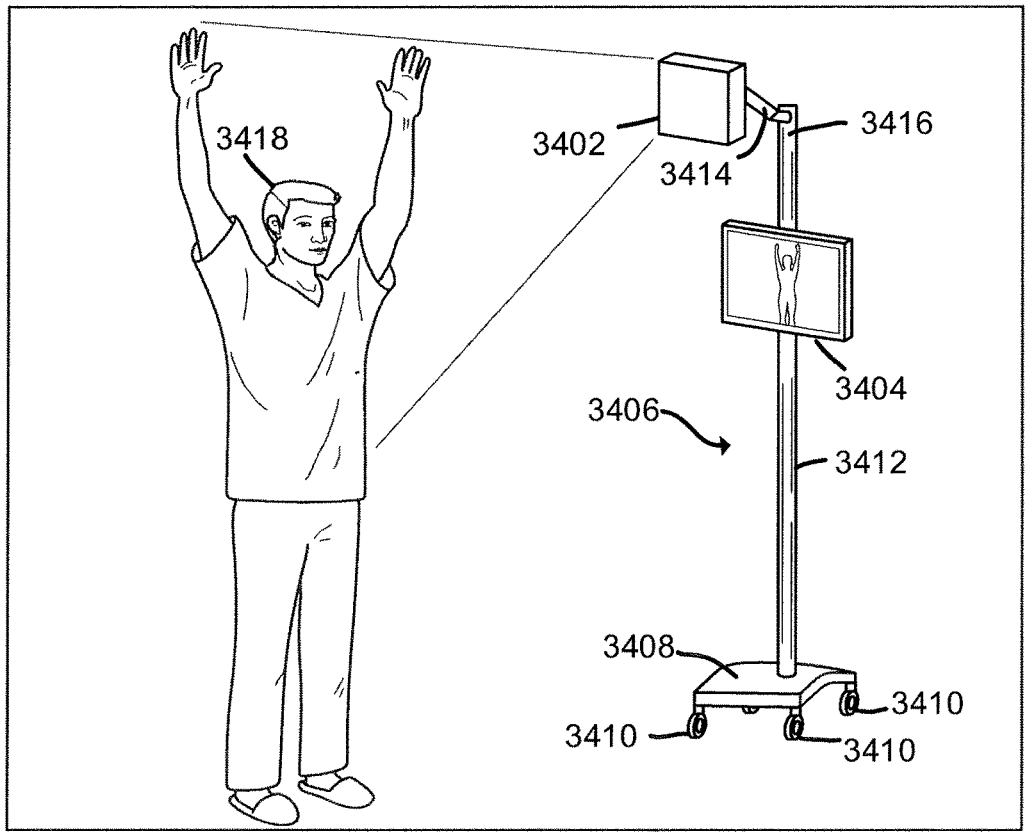
FIG. 35 is a perspective view of a system for monitoring a patient performing physical therapy using one or more radar sensors.

In use, the mobile physical therapy device 3406 may be used to instruct a patient 3418 to perform physical therapy in a similar manner as discussed above in regard to FIGS. 32 & 33. For example, the mobile physical therapy device 3406 may instruct a patient 3418 to have his arms by his side, as shown in FIG. 34, and then instruct the patient 3418 to raise his arms, as shown in FIG. 35. Of course, it should be appreciated that certain exercises may not be possible in a patient bed 3202 that may be possible while standing up, such as a walking exercise.

Figure 36:
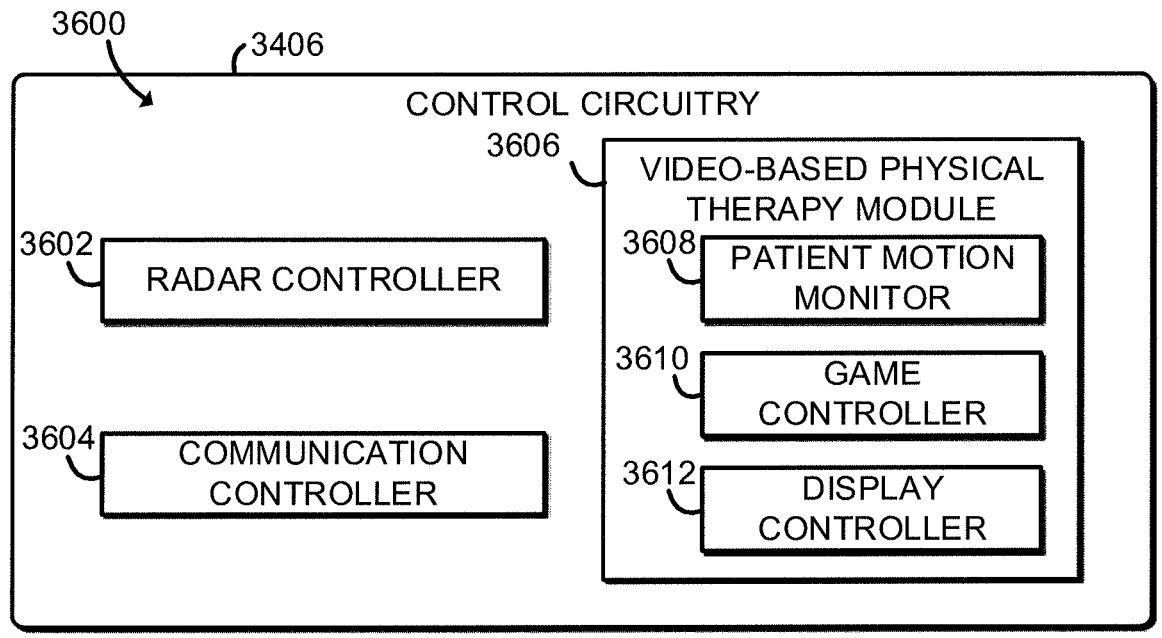
FIG. 36 is a block diagram of an environment that may be established by some or all of the circuitry of FIGS. 32-35.

Referring now to FIG. 36, in an illustrative embodiment, control circuitry 3206 establishes an environment 3600 during operation. The illustrative environment 3600 includes a radar controller 3602, a communication controller 3604, and a video-based physical therapy module 3606. The various modules of the environment 3600 may be embodied as hardware, software, firmware, or a combination thereof. For example, the various modules, logic, and other components of the environment 3600 may form a portion of, or otherwise be established by, a processor, memory, or other hardware components of the control circuitry 3206. As such, in some embodiments, one or more of the modules of the environment 3600 may be embodied as circuitry or collection of electrical devices (e.g., radar controller circuitry 3602, communication controller circuitry 3604, video-based physical therapy circuitry 3606, etc.). It should be appreciated that, in such embodiments, one or more of the circuits (e.g., the radar controller circuitry 3602, the communication controller circuitry 3604, the video-based physical therapy circuitry 3606, etc.) may form a portion of one or more of the processor, the memory, the data storage, and/or other components of the control circuitry 3206. Additionally, in some embodiments, one or more of the illustrative modules may form a portion of another module and/or one or more of the illustrative modules may be independent of one another. Further, in some embodiments, one or more of the modules of the environment 3600 may be embodied as virtualized hardware components or emulated architecture, which may be established and maintained by the processor or other components of the control circuitry 3206.

The radar controller 3602, which may be embodied as hardware, firmware, software, virtualized hardware, emulated architecture, and/or a combination thereof as discussed above, is configured to interface with the radar sensor 3204, 3402. The radar controller 3602 may send commands to the radar sensor 3204, 3402, configure the radar sensor 3204, 3402, and receive data from the radar sensor 3204, 3402. In the illustrative embodiment, the radar controller 3602 receives indications of the signals received by the radar sensor 3204, 3402 such as the intensity, phase, electric field, etc., received at each receiver of the radar sensor 3204, 3402. In some embodiments, the radar sensor 3204, 3402 may perform some pre-processing before sending data to the radar controller 3602, such as by processing data received to provide an indication of the position or movement of the patient.

The communication controller 3604 is configured to communicate with other devices, such as the electronic medical records server 206 or the nurse call system 208. The communication controller 3604 may communicate with other devices directly or indirectly through, for example, Ethernet, Bluetooth®, Wi-Fi®, WiMAX, near field communication (NFC), etc. The communication controller 3604 may transmit and data related to physical therapy exercises, such as previous patient performance data, instructions physical therapy to be performed, and current patient performance data.

The video-based physical therapy module 3606, which may be embodied as hardware, firmware, software, virtualized hardware, emulated architecture, and/or a combination thereof as discussed above, is configured to provide video instructions for physical therapy exercises to a patient. The physical therapy exercises may be any suitable exercises, such as range-of-motion exercises, muscle-strengthening exercises, coordination and balance exercises, walking exercises, general conditioning exercises, etc. The video-based physical therapy module 3606 may monitor the patient's motion during the physical therapy exercises. The video-based physical therapy module 3606 may track movement of patient's limbs, torso, or other body parts. The video-based physical therapy module 3606 may compare the motions of the patient to the motions instructed by the video-based physical therapy module 3606. In some embodiments, the physical therapy exercises can be "gamified," such as by allowing a user to earn points or achievements based on time spent performing exercises or results obtained. The physical therapy exercises may be done while the patient is supine, siting up, or in any other suitable position. The video-based physical therapy module 3606 may select physical therapy exercises for the patient based on, e.g., an exercise selected by a patient or caregiver, previous performance data of the patient, a pre-determined physical therapy routine, etc.

Figure 37:
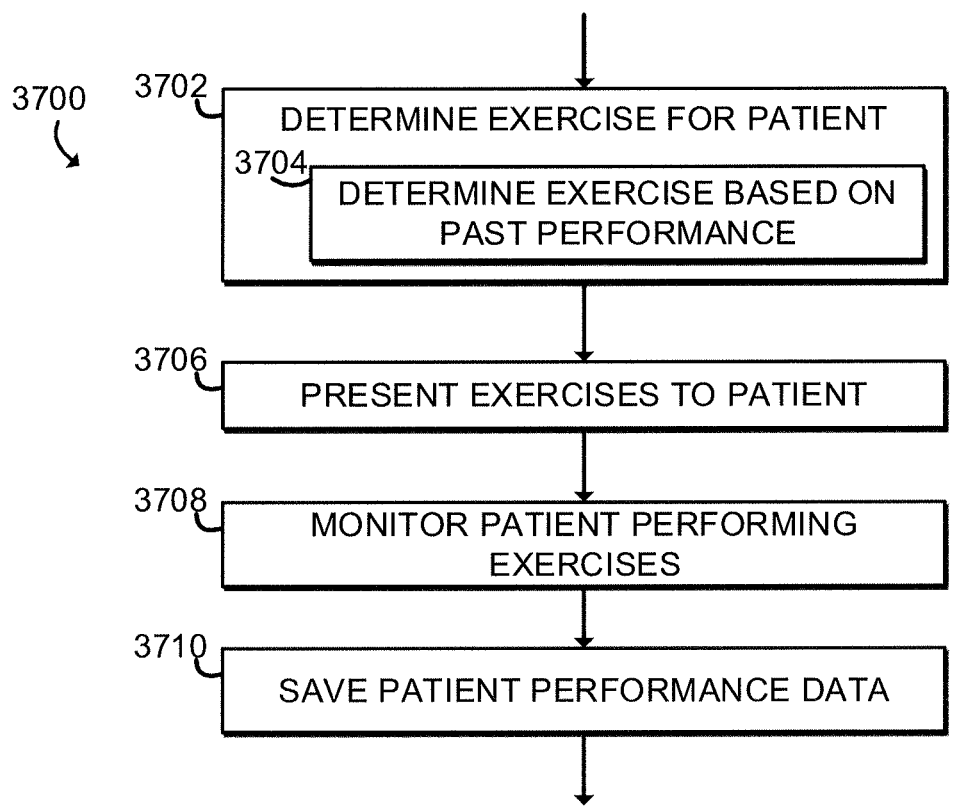
FIG. 37 is a flow chart of one embodiment of a method to monitor a patient performing physical therapy in the system of FIGS. 32-35.

Referring now to FIG. 37, in use, a method 3700 for facilitating monitored physical therapy exercises by a patient may be performed. In some embodiments, some or all of the method 3700 may be performed by the control circuitry 3206. Additionally or alternatively, in some embodiments, certain portions of the method 3700 may be performed by a person, such as a caregiver of the patient. For example, a caregiver may determine what physical therapy exercises should be done and configure the control circuitry 3206 to instruct the patient to perform those physical therapy exercises. The method 3700 begins in block 3702, in which the control circuitry 3206 determines a physical therapy exercises for a patient. The control circuitry 3206 may determine the physical therapy exercises in any suitable way, such as based on a medical condition of the patient, a configuration of a caregiver, etc. In some embodiments, in block 3704, the control circuitry 3206 may determine an exercise based on past performance of the patient. For example, if the patient successfully completed 10 minutes of physical therapy exercises previously, the control circuitry 3206 may determine that 12 minutes of physical therapy exercises should be done.

In block 3706, the control circuitry 3206 presents one or more instructions of the exercise to the patient. For example, a video of a person or avatar may be presented on a display, such as display 3212 or display 3404, and the user may be instructed to follow along with moving arms up, moving arms, down, etc. In block 3708, the control circuitry 3206 monitors the patient performing the physical therapy exercises based on data acquired by radar sensor 3204 or radar sensor 3402, for example. It should be appreciated that, in the illustrative embodiment, the control circuitry 3206 provides the patient's performance as feedback. For example, if a patient is not raising his arms high enough, the control circuitry 3206 may notify the patient and instruct the patient on how to correctly perform the physical therapy exercise. Such a notification appears on display 3212 or display 3404 in some embodiments.

In block 3710, the control circuitry 3206 saves the patient performance data for the physical therapy exercises. The patient performance data may be used to monitor a patient's progress, to develop a treatment plan, to determine future physical therapy exercises, etc.

Figure 38:
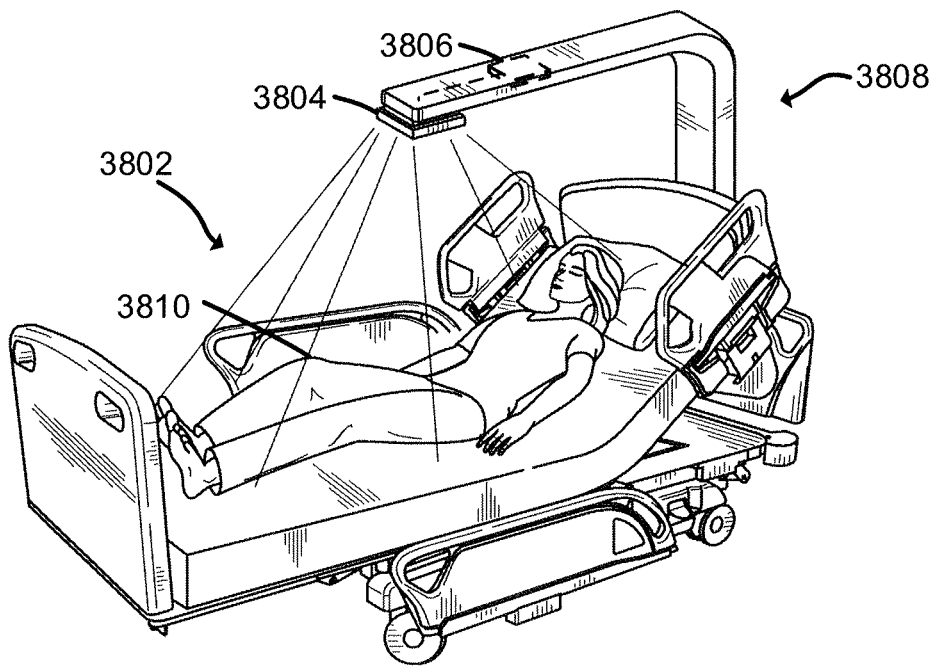
FIG. 38 is a perspective view of a system for monitoring a patient sleeping in a bed using one or more radar sensors.
Figure 39:
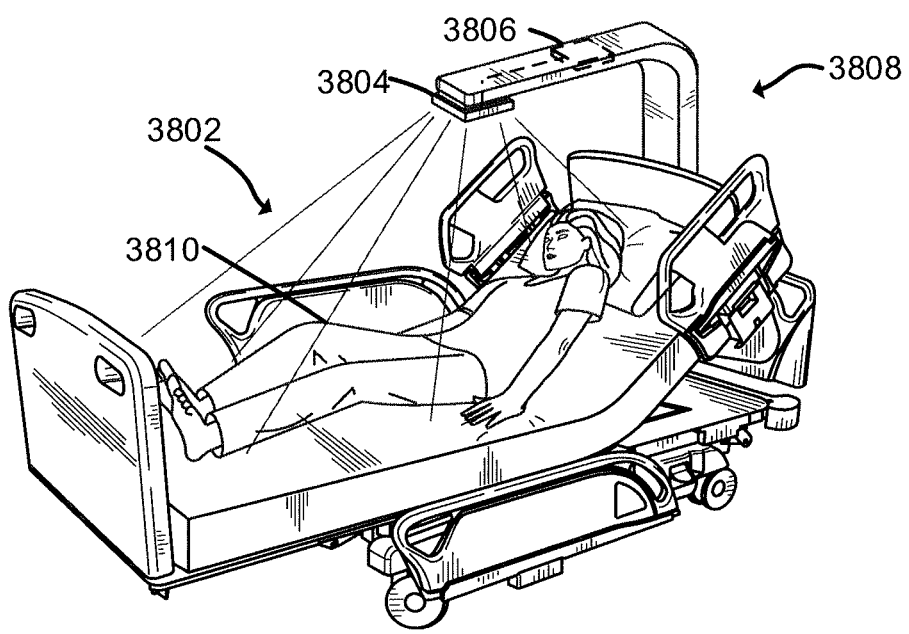
FIG. 39 is a perspective view of a system for monitoring a patient sleeping in a bed using one or more radar sensors.

Referring now to FIGS. 38 & 39, in one embodiment, a patient bed 3802 includes one or more radar sensors 3804 connected to control circuitry 3806. In the illustrative example, radar support mount 3808 is used to support the one or more radar sensors 3804 and control circuitry 3806. Mount 610 was discussed above in connection with FIG. 6 and the discussion is equally applicable to the use of mount 3808 with bed 3802 of FIGS. 38 & 39.

In use, the control circuitry 3806 monitors a patient 3810 that is sleeping or resting. The control circuitry 3806 monitors certain actions of the patient 3810 indicating a comfort level of the patient, such as whether the patient is pushing up in bed, as shown in FIG. 39. The control circuitry 3806 may control certain parameters of the bed in response to movements of the patient in order to increase the comfort level of the patient. In the illustrative embodiment, the control circuitry 3806 may change the pressure in one or more air bladders of the surface of the patient bed 3802, such as an air bladder supporting the upper body of the patient, an air bladder supporting the sacrum of the patient, and/or an air bladder supporting the legs of the patient. Additionally or alternatively, the control circuitry 3806 may change a ratio of the pressures of two or more of the air bladders. In some embodiments, data from multiple patients in multiple patient beds is aggregated and analyzed to determine appropriate pressure settings for different patients.

Figure 40:
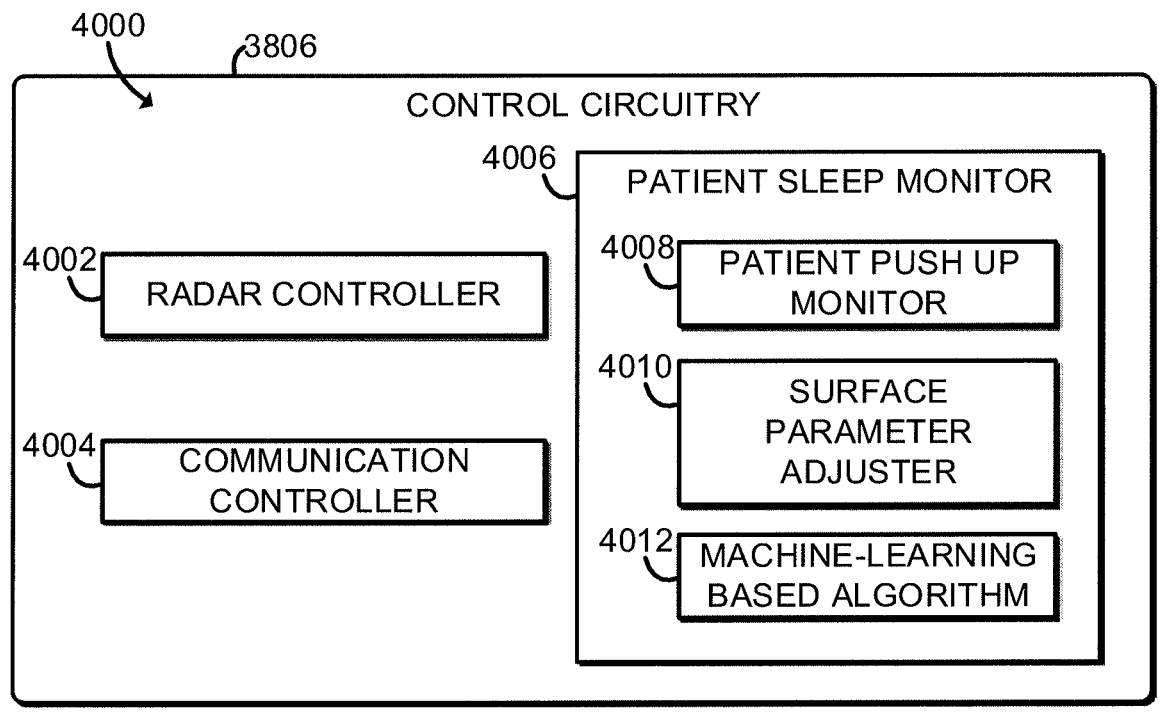
FIG. 40 is a block diagram of an environment that may be established by some or all of the circuitry of FIGS. 38 and 39.

Referring now to FIG. 40 in an illustrative embodiment, control circuitry 3806 establishes an environment 4000 during operation. The illustrative environment 4000 includes a radar controller 4002, a communication controller 4004, and a patient sleep monitor 4006. The various modules of the environment 4000 may be embodied as hardware, software, firmware, or a combination thereof. For example, the various modules, logic, and other components of the environment 4000 may form a portion of, or otherwise be established by, a processor, memory, or other hardware components of the control circuitry 3806. As such, in some embodiments, one or more of the modules of the environment 4000 may be embodied as circuitry or collection of electrical devices (e.g., radar controller circuitry 4002, communication controller circuitry 4004, patient sleep monitor circuitry 4006, etc.). It should be appreciated that, in such embodiments, one or more of the circuits (e.g., the radar controller circuitry 4002, the communication controller circuitry 4004, the patient sleep monitor circuitry 4006, etc.) may form a portion of one or more of the processor, the memory, the data storage, and/or other components of the control circuitry 3806. Additionally, in some embodiments, one or more of the illustrative modules may form a portion of another module and/or one or more of the illustrative modules may be independent of one another. Further, in some embodiments, one or more of the modules of the environment 4000 may be embodied as virtualized hardware components or emulated architecture, which may be established and maintained by the processor or other components of the control circuitry 3806.

The radar controller 4002, which may be embodied as hardware, firmware, software, virtualized hardware, emulated architecture, and/or a combination thereof as discussed above, is configured to interface with the radar sensor 3806. The radar controller 4002 may send commands to the radar sensor 3806, configure the radar sensor 3806, and receive data from the radar sensor 3806. In the illustrative embodiment, the radar controller 4002 receives indications of the signals received by the radar sensor 3806, such as the intensity, phase, electric field, etc., received at each receiver of the radar sensor 3806. In some embodiments, the radar sensor 3806 may perform some pre-processing before sending data to the radar controller 4002, such as by processing data received to provide an indication of the position or movement of the patient.

The communication controller 4004 is configured to communicate with other devices, such as the electronic medical records server 206 or the nurse call system 208. The communication controller 4004 may communicate with other devices directly or indirectly through, for example, Ethernet, Bluetooth®, Wi-Fi®, WiMAX, near field communication (NFC), etc. The communication controller 4004 may transmit and data related to patient's movement while sleeping, such as when the patient pushes up in bed.

The patient sleep monitor 4006, which may be embodied as hardware, firmware, software, virtualized hardware, emulated architecture, and/or a combination thereof as discussed above, is configured to monitor the patient while the patient is sleeping. The patient sleep monitor 4006 includes a patient push-up monitor 4008, a surface parameter adjuster 4010, and a machine-learning-based algorithm in block 4012.

The patient push-up monitor 4008 is configured to monitor for a patient pushing up in bed. A patient pushing up in bed may be an indication that the parameters of the surface such as air pressure bladder can be improved to provide the patient a more comfortable experience.

The surface parameter adjuster 4010 is configured to adjust a parameter of the surface to improve the comfort of the patient. For example, the surface parameter adjuster 4010 may change the pressure in one or more air bladders of the surface of the patient bed 3802, such as an air bladder supporting the upper body of the patient, an air bladder supporting the sacrum of the patient, and/or an air bladder supporting the legs of the patient. Additionally or alternatively, the surface parameter adjuster 4010 may change a ratio of the pressures of two or more of the air bladders.

The machine-learning-based algorithm 4012 is configured to use a machine-learning-based algorithm to determine parameters for the patient bed 3802. The machine-learning-based algorithm 4012 may take as an input parameters of the patient, such as patient movement, patient position, patient weight, patient height, etc. The machine-learning-based algorithm 4012 provides as an output an appropriate pressure setting for one or more air bladders. It should be appreciated that, in some embodiments, parameters of the patient, including movement data corresponding to various air bladder pressures, may be aggregated and used as training data to improve the machine-learning-based algorithm 4012.

Figure 41:
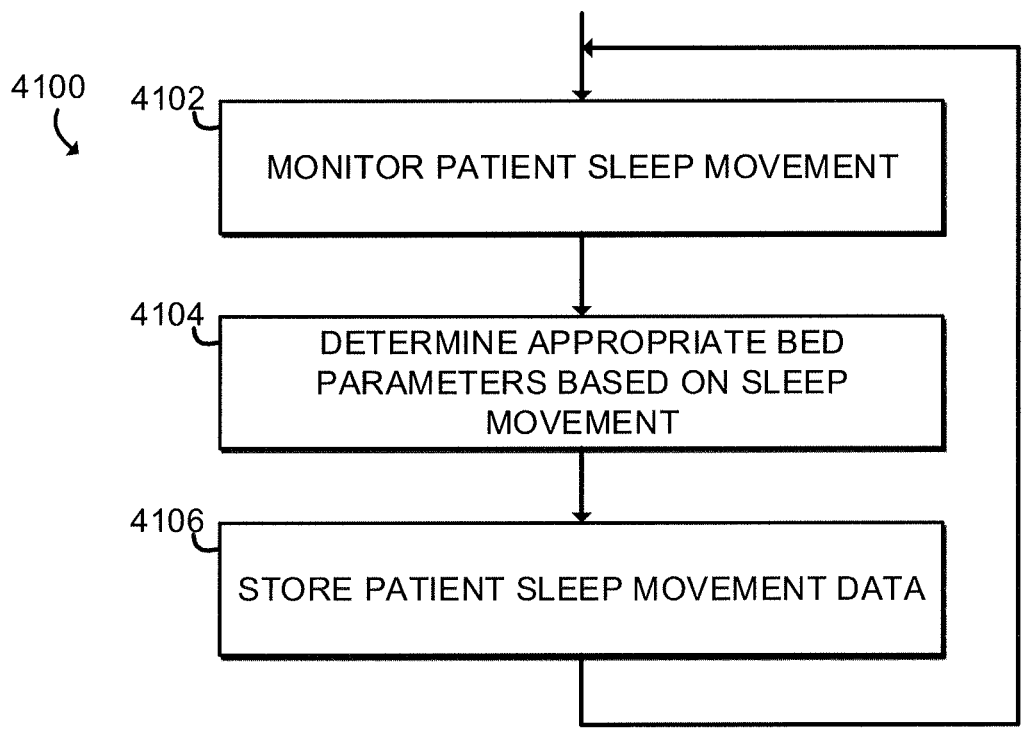
FIG. 41 is a flow chart of one embodiment of a method to monitor a patient sleeping in the system of FIGS. 38 and 39.

Referring now to FIG. 41, in use, a method 4100 for monitoring sleep movement of a patient may be performed. In some embodiments, some or all of the method 4100 may be performed by the control circuitry 3806. Additionally or alternatively, in some embodiments, certain portions of the method 4100 may be performed by a person, such as a caregiver of the patient. The method 4100 begins in block 4102, in which the control circuitry 3806 monitors a patient's sleep movement, such as how frequently the patient pushes up in bed.

In block 4104, the control circuitry 3806 determines appropriate bed parameters based on the sleep movement of the patient. For example, the control circuitry 3806 may change the pressure in one or more air bladders of the surface of the patient bed 3802, such as an air bladder supporting the upper body of the patient, an air bladder supporting the sacrum of the patient, and/or an air bladder supporting the legs of the patient. Additionally or alternatively, the control circuitry 3806 may change a ratio of the pressures of two or more of the air bladders. In some embodiments, the control circuitry 3806 may employ a machine-learning-based algorithm to determine appropriate bed parameters based on the sleep movement of the patient. After determining appropriate bed parameters, the control circuitry 3806 then applies those parameters.

In block 4106, the control circuitry 3806 stores the patient sleep movement data. It should be appreciated that, in some embodiments, patient sleep movement data may be aggregated and used as training data for a machine-learning-based algorithm or may be analyzed to determine appropriate baseline bed parameters for a new patient.

Figure 42:
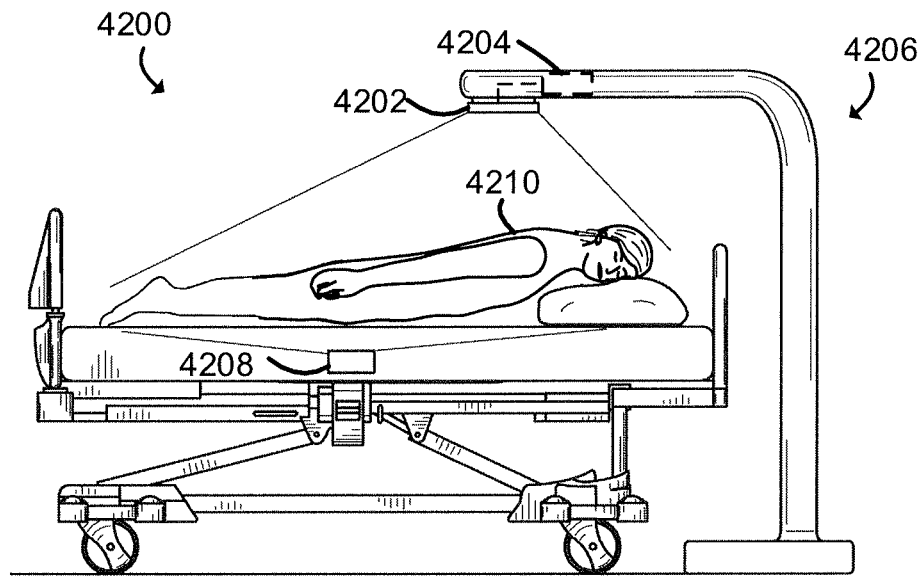
FIG. 42 is a perspective view of a system for monitoring a patient in a prone position using one or more radar sensors.
Figure 43:
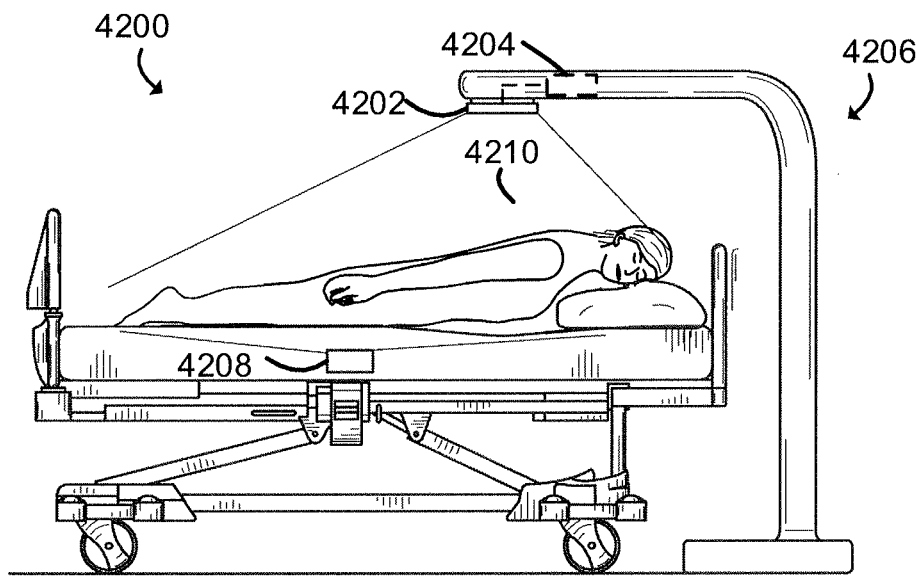
FIG. 43 is a perspective view of a system for monitoring a patient in a prone position using one or more radar sensors.

Referring now to FIGS. 42 & 43, in one embodiment, a patient bed 4200 includes one or more radar sensors 4202 connected to control circuitry 4204. In the illustrative example, radar support mount 4206 is used to support the one or more radar sensors 4202 and control circuitry 4204. Mount 610 was discussed above in connection with FIG. 6 and the discussion is equally applicable to the use of mount 4206 with bed 4200 of FIGS. 42 & 43. In the illustrative embodiment, one or more additional radar sensors 4208 may be located in a side rail or beneath the patient 4210.

In use, the control circuitry 4204 monitors the breathing of a patient 4210 that is lying in a prone position. In particular, the control circuitry 4204 monitors whether the surface of the patient bed 4200 is restricting the breathing of the patient. If there is a gap between the sternum of the patient and the surface of the patient bed 4200 while the patient 4210 breathes in, then the surface of the patient bed 4200 is not restricting the breathing of the patient. The control circuitry 4204 may monitor a gap between the sternum of the patient and the surface of the patient bed 4200 in any suitable way. For example, in one embodiment, the control circuitry 4204 may directly monitor the gap using the radar sensor 4208. Additionally or alternatively, in some embodiments, the control circuitry 4204 may deflate an air bladder below the sternum as the patient breathes in, as shown in FIG. 43. If there is still not a gap between the sternum of the patient and the surface of the patient bed 4200, then the air bladder should be deflated more.

Figure 44:
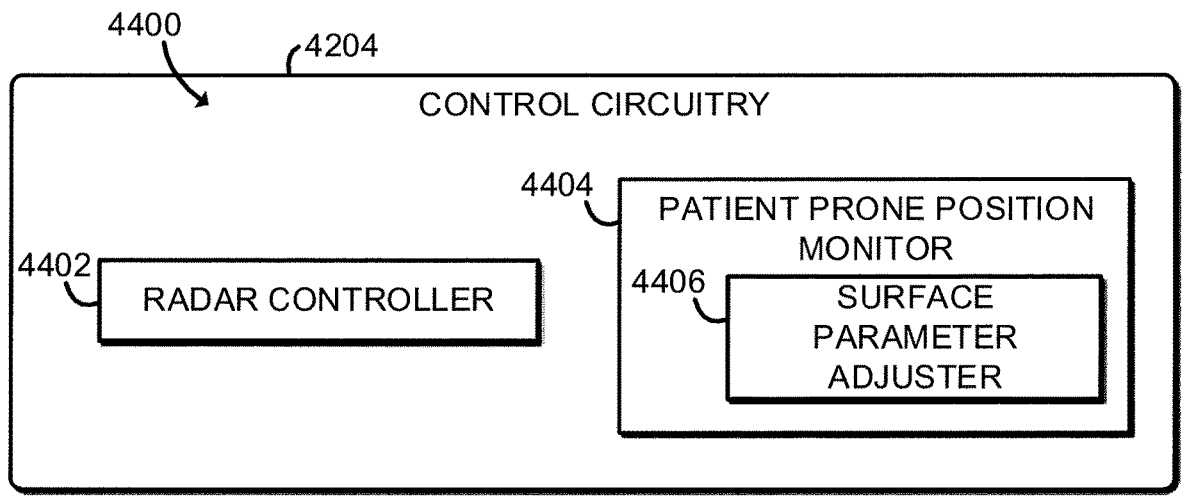
FIG. 44 is a block diagram of an environment that may be established by some or all of the circuitry of FIGS. 42 and 43.

Referring now to FIG. 44 in an illustrative embodiment, control circuitry 4204 establishes an environment 4400 during operation. The illustrative environment 4400 includes a radar controller 4402 and a patient prone position monitor 4404. The various modules of the environment 4400 may be embodied as hardware, software, firmware, or a combination thereof. For example, the various modules, logic, and other components of the environment 4400 may form a portion of, or otherwise be established by, a processor, memory, or other hardware components of the control circuitry 4204. As such, in some embodiments, one or more of the modules of the environment 4400 may be embodied as circuitry or collection of electrical devices (e.g., radar controller circuitry 4402, patient prone position monitor circuitry 4404, etc.). It should be appreciated that, in such embodiments, one or more of the circuits (e.g., the radar controller circuitry 4402, the patient prone position monitor circuitry 4404, etc.) may form a portion of one or more of the processor, the memory, the data storage, and/or other components of the control circuitry 4204. Additionally, in some embodiments, one or more of the illustrative modules may form a portion of another module and/or one or more of the illustrative modules may be independent of one another. Further, in some embodiments, one or more of the modules of the environment 4400 may be embodied as virtualized hardware components or emulated architecture, which may be established and maintained by the processor or other components of the control circuitry 4204.

The radar controller 4402, which may be embodied as hardware, firmware, software, virtualized hardware, emulated architecture, and/or a combination thereof as discussed above, is configured to interface with the radar sensor 4202, 4208. The radar controller 4402 may send commands to the radar sensor 4202, 4208, configure the radar sensor 4202, 4208, and receive data from the radar sensor 4202, 4208. In the illustrative embodiment, the radar controller 4402 receives indications of the signals received by the radar sensor 4202, 4208, such as the intensity, phase, electric field, etc., received at each receiver of the radar sensor 4202, 4208. In some embodiments, the radar sensor 4202, 4208 may perform some pre-processing before sending data to the radar controller 4402, such as by processing data received to provide an indication of the position or movement of the patient.

The patient prone position monitor 4404, which may be embodied as hardware, firmware, software, virtualized hardware, emulated architecture, and/or a combination thereof as discussed above, is configured to monitor the patient while sleeping. In particular, the patient prone position monitor 4404 monitors whether the surface of the patient bed 4200 is restricting the breathing of the patient. If there is a gap between the sternum of the patient and the surface of the patient bed 4200 while the patient 4210 breathes in, then the surface of the patient bed 4200 is not restricting the breathing of the patient. The patient prone position monitor 4404 may monitor a gap between the sternum of the patient and the surface of the patient bed 4200 in any suitable way. For example, in one embodiment, the patient prone position monitor 4404 may directly monitor the gap using the radar sensor 4208. Additionally or alternatively, in some embodiments, the patient prone position monitor 4404 may deflate an air bladder below the sternum as the patient breathes in. If there is still not a gap between the sternum of the patient and the surface of the patient bed 4200, then the air bladder should be deflated more. A surface parameter adjuster 4406 of the patient prone position monitor 4404 is configured to adjust parameters of the surface to allow the patient the necessary room to breathe, such as by deflating an air bladder under the sternum of the patient. In some embodiments, if there is too large of a gap between the sternum of the patient and the surface of the patient bed 4200, the surface parameter adjuster 4406 may inflate the air bladder under the sternum of the patient.

Figure 45:
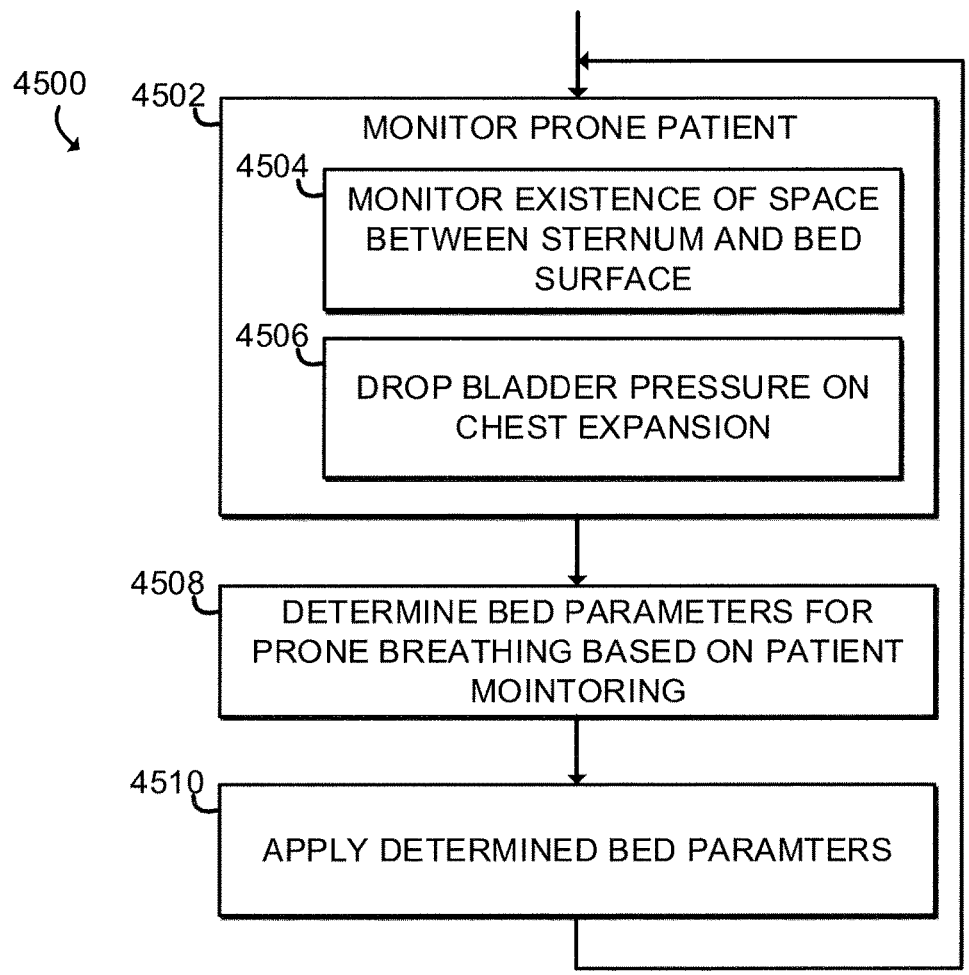
FIG. 45 is a flow chart of one embodiment of a method to monitor a patient in a prone position in the system of FIGS. 42 and 43.

Referring now to FIG. 45, in use, a method 4500 for monitoring a patient in a prone position may be performed.

In some embodiments, some or all of the method 4500 may be performed by the control circuitry 4204. Additionally or alternatively, in some embodiments, certain portions of the method 4500 may be performed by a person, such as a caregiver of the patient. The method 4500 begins in block 4502, in which the control circuitry 4204 monitors patient lying in the prone position. The control circuitry 4204 may monitor the existence of a gap between the sternum of the patient and the surface of the patient bed 4200 in block 4504. Additionally or alternatively, the control circuitry 4204 may drop the bladder pressure below the sternum as the patient breaths in in block 4506 to monitor for the presence of a gap in block 4506.

In block 4508, the control circuitry 4204 determines bed parameters for the patient in the prone position based on the patient monitoring. For example, if there is not a gap between the sternum of the patient and the surface of the patient bed 4200, then the control circuitry 4204 may determine that the pressure of the air bladder below the patient's sternum should be dropped. If there is too large of a gap, the control circuitry 4204 may determine that the pressure of the air bladder below the patient's sternum should be increased.

In block 4510, the control circuitry 4204 applies the bed parameters, such as by inflating or deflating one or more air bladders. The method 4500 then loops back to block 4502 to continue monitoring the patient in the prone position.

Figure 46:
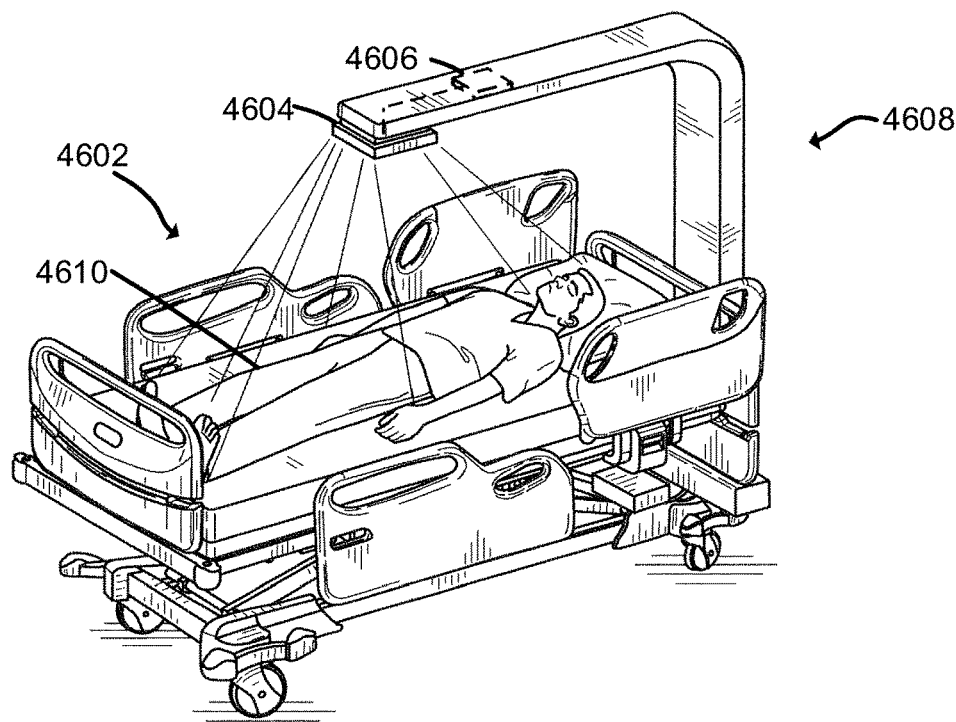
FIG. 46 is a perspective view of a system for determining a patient's weight using one or more radar sensors.

Referring now to FIG. 46, in one embodiment, a patient bed 4602 includes one or more radar sensors 4604 connected to control circuitry 4606. In the illustrative example, radar support mount 4608 is used to support the one or more radar sensors 4604 and control circuitry 4606. Mount 610 was discussed above in connection with FIG. 6 and the discussion is equally applicable to the use of support mount 4608 with bed 4600 of FIG. 46. In some embodiment, one or more additional radar sensors may be located in a side rail or beneath the patient 4610.

In use, the control circuitry 4608 estimates a weight of the patient 4610 based at least in part of data from one or more radar sensors 4604. For example, the control circuitry 4608 may measure a contour of the patient and/or perform a 3D scan of the patient. The control circuitry 4608 may then determine a volume of the patient, estimate an average density of the patient, and then estimate a weight of the patient.

Figure 47:
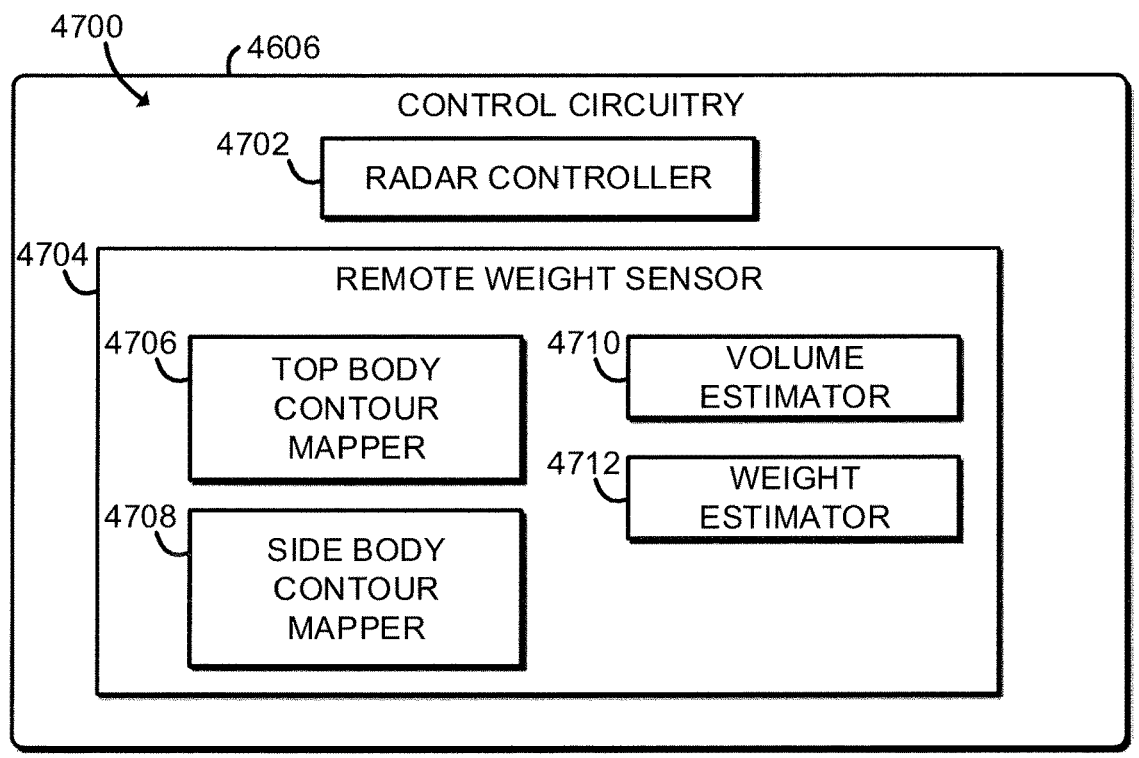
FIG. 47 is a block diagram of an environment that may be established by some or all of the circuitry of FIG. 46.

Referring now to FIG. 47 in an illustrative embodiment, control circuitry 4606 establishes an environment 4700 during operation. The illustrative environment 4700 includes a radar controller 4702 and a remote weight sensor 4704. The various modules of the environment 4700 may be embodied as hardware, software, firmware, or a combination thereof. For example, the various modules, logic, and other components of the environment 4700 may form a portion of, or otherwise be established by, a processor, memory, or other hardware components of the control circuitry 4606. As such, in some embodiments, one or more of the modules of the environment 4700 may be embodied as circuitry or collection of electrical devices (e.g., radar controller circuitry 4702, remote weight sensor circuitry 4704, etc.). It should be appreciated that, in such embodiments, one or more of the circuits (e.g., the radar controller circuitry 4702, the remote weight sensor circuitry 4704, etc.) may form a portion of one or more of the processor, the memory, the data storage, and/or other components of the control circuitry 4606. Additionally, in some embodiments, one or more of the illustrative modules may form a portion of another module and/or one or more of the illustrative modules may be independent of one another. Further, in some embodiments, one or more of the modules of the environment 4700 may be embodied as virtualized hardware components or emulated architecture, which may be established and maintained by the processor or other components of the control circuitry 4606.

The radar controller 4702, which may be embodied as hardware, firmware, software, virtualized hardware, emulated architecture, and/or a combination thereof as discussed above, is configured to interface with the radar sensor 4604. The radar controller 4702 may send commands to the radar sensor 4604, configure the radar sensor 4604, and receive data from the radar sensor 4604. In the illustrative embodiment, the radar controller 4702 receives indications of the signals received by the radar sensor 4604, such as the intensity, phase, electric field, etc., received at each receiver of the radar sensor 4604. In some embodiments, the radar sensor 4604 may perform some pre-processing before sending data to the radar controller 4702, such as by processing data received to provide an indication of the position or movement of the patient.

The remote weight sensor 4704, which may be embodied as hardware, firmware, software, virtualized hardware, emulated architecture, and/or a combination thereof as discussed above, is configured to estimate a weight of the patient in the patient bed 4602. The remote weight sensor 4704 includes a top body contour mapper 4706, a side body contour mapper 4708, a volume estimator 4710, and a weight estimator 4712.

The top body contour mapper 4706 is configured to map a contour or 3D surface of the patient using a radar sensor positioned above the patient 4610. The side body contour mapper 4708 is configured to map a contour or 3D surface of the patient using a radar sensor positioned to the side of the patient 4610. It should be appreciated that, in some embodiments, the radar signal may penetrate clothing, blankets, and sheets, allowing for an estimate of patient weight to be determined even when the patient is covered.

The volume estimator 4710 is configured to estimate a volume of the patient. The volume estimator 4710 may use the top and/or side contour mapping to estimate a volume of the patient.

The weight estimator 4712 is configured to estimate a weight of the patient 4610 based on the estimated volume of the patient. The weight estimator 4712 may estimate a density of the patient or may use an input from a caregiver, such as a measured body fat percentage.

Figure 48:
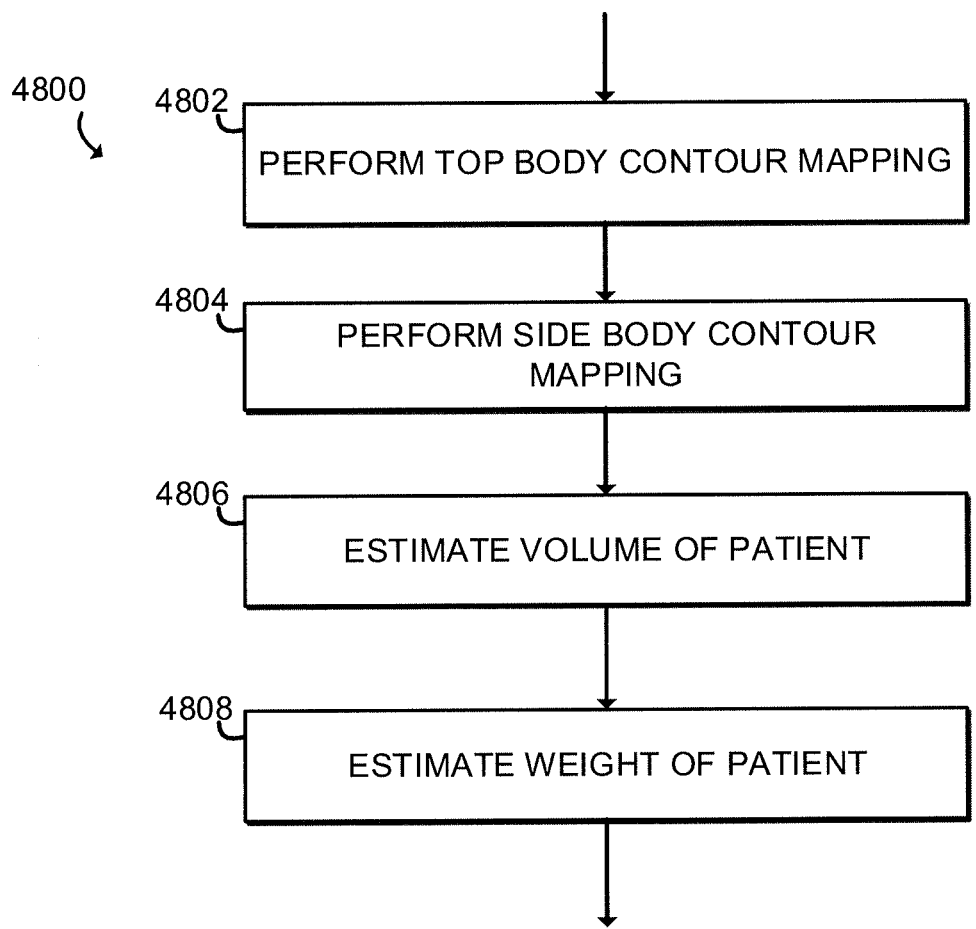
FIG. 48 is a flow chart of one embodiment of a method to determine a patient's weight in the system of FIG. 46.

Referring now to FIG. 48, in use, a method 4800 for estimating a weight of a patient may be performed. In some embodiments, some or all of the method 4800 may be performed by the control circuitry 4606. Additionally or alternatively, in some embodiments, certain portions of the method 4800 may be performed by a person, such as a caregiver of the patient. The method 4800 begins in block 4802, in which the control circuitry 4606 performs a top body contour mapping. In block 4804, the control circuitry 4606 performs a side body contour mapping.

In block 4806, the control circuitry 4606 estimates a volume of the patient. The control circuitry 4606 may use the top and/or side contour mapping to estimate a volume of the patient. In block 4808, control circuitry 4606 estimates a weight of the patient 4610 based on the estimated volume of the patient. The control circuitry 4606 may estimate a density of the patient or may use an input from a caregiver, such as a measured body fat percentage.

The discussion of bed 102 of FIG. 1 and its various component parts, including the radar sensors 106, 108, 110 and control circuitry 112, is equally applicable to beds 300, 602, 1002, 1602, 2402, 3202, 3802, 4200, 4602 of FIGS. 3, 6, 10, 16, 24, 32, 38, 42, and 46, respectively, unless specifically noted otherwise.

Although certain illustrative embodiments have been described in detail above, variations and modifications exist within the scope and spirit of this disclosure as described and as defined in the following claims.

The invention claimed is:

1. A system for monitoring movement of a patient, the system comprising:
a plurality of radar sensors coupled to a patient bed and situated above a patient supported on the patient bed, each of the plurality of radar sensors configured to:
transmit a radar signal towards the patient on the patient bed; and
receive a reflection of the radar signal from the patient, and
circuitry configured to:
receive data from the plurality of radar sensors indicative of the reflection of the radar signal from the patient; and
determine, based on the data from the plurality of radar sensors, a position parameter of the patient, wherein the position parameter is indicative of a location or orientation of the patient on the patient bed;
wherein the patient bed includes a base, an upper frame assembly, and a lift system coupling the upper frame assembly to the base,
wherein the patient bed includes a mast having a lower end coupled to the upper frame assembly, a first arm extending from an upper end of the mast along a longitudinal dimension of the patient bed, and right and left arms that each extend in a cantilevered manner from right and left sides, respectively, of the first arm, wherein the plurality of radar sensors comprise a first radar sensor coupled to the first arm, a second radar sensor coupled to the right arm, and a third radar sensor coupled to the left arm.

2. The system of claim 1, wherein the circuitry is further configured to:
determine whether the patient should be rotated based on the position parameter of the patient.

3. The system of claim 2, wherein to determine whether the patient should be rotated comprises to determine whether the patient should be rotated to prevent a pressure ulcer.

4. The system of claim 2, wherein to determine whether the patient should be rotated comprises to determine whether the patient should be rotated to prevent laryngopharyngeal reflux.

5. The system of claim 2, wherein to determine whether the patient should be rotated comprises to determine whether the patient should be rotated to elevate a lung of the patient.

6. The system of claim 2, wherein to determine whether the patient should be rotated comprises to determine that the patient has not been rotated for at least a threshold amount of time.

7. The system of claim 1, wherein the circuitry is further configured to:
determine, based on the position parameter, a subset of a plurality of rotation bladders of the patient bed to inflate in order to rotate the patient; and
send a signal to inflate the subset of the plurality of rotation bladders.

8. The system of claim 1, wherein the circuitry is further configured to:
determine, based on the position parameter, a subset of a plurality of rotation bladders of the patient bed to inflate in order to move the patient towards a center of the patient bed; and
send a signal to inflate the subset of the plurality of rotation bladders.

9. The system of claim 1, wherein the circuitry is further configured to:
determine, based on the position parameter, a subset of a plurality of percussion and vibration (P & V) bladders of the patient bed to inflate in order to perform P & V therapy on the patient, wherein the subset of the plurality of P & V bladders are P &V bladders under a current position of the patient; and
send a signal to inflate the subset of the plurality of P & V bladders.

10. The system of claim 9, wherein the circuitry is further configured to:
transmit, by one or more of the first, second, and third radar sensors, an additional radar signal towards the patient during the P & V therapy;
receive, by the one or more of the first, second, and third radar sensors, a reflection of the additional radar signal from the patient;
receive additional data from the one or more of the first, second, and third radar sensors indicative of the reflection of the additional radar signal from the patient;
determine, based on the additional data from the one or more of the first, second, and third radar sensors, an amplitude of vibration of the patient caused by the P & V therapy; and
adjust a signal sent to inflate the subset of the plurality of P & V bladders based on the amplitude of vibration of the patient.

11. The system of claim 9, wherein the circuitry is further configured to:
determine, based on the position parameter, a subset of a plurality of rotation bladders of the patient bed to inflate in order to move the patient towards a center of the patient bed; and
send a signal to inflate the subset of the plurality of rotation bladders to move the patient towards the center of the patient bed prior to sending the signal to inflate the subset of the plurality of P & V bladders.

12. A method for monitoring movement of a patient, the method comprising:
transmitting, by each of a plurality of radar sensors coupled to a patient bed and situated above a patient supported on the patient bed, a radar signal towards the patient on the patient bed;
receiving, by each of the plurality of radar sensors, a reflection of the respective radar signal from the patient;
receiving, by circuitry, data from each of the plurality of radar sensors indicative of the reflection of the respective radar signal from the patient; and
determining, by the circuitry and based on the data from the plurality of radar sensors, a position parameter of the patient, wherein the position parameter is indicative of a location or orientation of the patient on the patient bed;
wherein the patient bed includes a base, an upper frame assembly, and a lift system coupling the upper frame assembly to the base, wherein the patient bed includes a mast having a lower end coupled to the upper frame assembly, a first arm extending from an upper end of the mast along a longitudinal dimension of the patient bed, and right and left arms that each extend in a cantilevered manner from right and left sides, respectively, of the first arm, wherein the plurality of radar sensors comprise a first radar sensor coupled to the first arm, a second radar sensor coupled to the right arm, and a third radar sensor coupled to the left arm.

13. The method of claim 12, the method further comprising:
determining, by the circuitry, whether the patient should be rotated based on the position parameter of the patient.

14. The method of claim 13, wherein determining whether the patient should be rotated comprises determining whether the patient should be rotated to prevent a pressure ulcer.

15. The method of claim 13, wherein determining whether the patient should be rotated comprises determining whether the patient should be rotated to prevent laryngopharyngeal reflux.

16. The method of claim 13, wherein determining whether the patient should be rotated comprises determining whether the patient should be rotated to elevate a lung of the patient.

17. The method of claim 13, wherein determining whether the patient should be rotated comprises determining that the patient has not been rotated for at least a threshold amount of time.

18. The method of claim 12, further comprising:
determining, by the circuitry and based on the position parameter, a subset of a plurality of rotation bladders of the patient bed to inflate in order to rotate the patient; and
sending, by the circuitry, a signal to inflate the subset of the plurality of rotation bladders.

19. The method of claim 12, further comprising:
determining, by the circuitry and based on the position parameter, a subset of a plurality of rotation bladders of the patient bed to inflate in order to move the patient towards a center of the patient bed; and
sending, by the circuitry, a signal to inflate the subset of the plurality of rotation bladders.

20. The method of claim 12, further comprising:
determining, by the circuitry and based on the position parameter, a subset of a plurality of percussion and vibration (P & V) bladders of the patient bed to inflate in order to perform P & V therapy on the patient, wherein the subset of the plurality of P & V bladders are P &V bladders under a current position of the patient; and
sending, by the circuitry, a signal to inflate the subset of the plurality of P & V bladders.

21. The method of claim 20, further comprising:
transmitting, by one or more of the first, second, and third radar sensors, an additional radar signal towards the patient during the P & V therapy;
receiving, by the one or more of the first, second, and third radar sensors, a reflection of the additional radar signal from the patient;
receiving, by the circuitry, additional data from the one or more of the first, second, and third radar sensors indicative of the reflection of the additional radar signal from the patient;
determining, by the circuitry and based on the additional data from the one or more of the first, second, and third radar sensors, an amplitude of vibration of the patient caused by the P & V therapy; and
adjusting, by the circuitry, a signal sent to inflate the subset of the plurality of P & V bladders based on the amplitude of vibration of the patient.

22. The method of claim 20, further comprising:
determining, by the circuitry and based on the position parameter, a subset of a plurality of rotation bladders of the patient bed to inflate in order to move the patient towards a center of the patient bed; and
sending, by the circuitry, a signal to inflate the subset of the plurality of rotation bladders to move the patient towards the center of the patient bed prior to sending the signal to inflate the subset of the plurality of P & V bladders.

* * * * *